United States Patent [19]
Mattheakis et al.

[11] Patent Number: 5,922,545
[45] Date of Patent: Jul. 13, 1999

[54] IN VITRO PEPTIDE AND ANTIBODY DISPLAY LIBRARIES

[75] Inventors: Larry C. Mattheakis, Cupertino; William J. Dower, Menlo Park, both of Calif.

[73] Assignee: Affymax Technologies N.V., Greenford, United Kingdom

[21] Appl. No.: 08/902,623

[22] Filed: Jul. 29, 1997

Related U.S. Application Data

[63] Continuation of application No. 08/586,176, Jan. 17, 1996, abandoned, which is a continuation-in-part of application No. PCT/US94/12206, Oct. 25, 1994, abandoned, which is a continuation-in-part of application No. 08/300,262, Sep. 2, 1994, abandoned, which is a continuation-in-part of application No. 08/144,775, Oct. 29, 1993, abandoned.

[51] Int. Cl.$^6$ .............................. C12Q 1/68; C12Q 1/70; G01N 33/53
[52] U.S. Cl. .................................. 435/6; 435/5; 435/7.1; 436/518
[58] Field of Search .......................... 435/6, 5, 7.1, 69.3; 436/518, 531, 534

[56] References Cited

U.S. PATENT DOCUMENTS

| | | | |
|---|---|---|---|
| 4,631,211 | 12/1986 | Houghten | 428/35 |
| 4,683,202 | 7/1987 | Mullis . | |
| 4,965,188 | 10/1990 | Mullis et al. . | |
| 5,223,409 | 6/1993 | Ladner et al. . | |
| 5,270,170 | 12/1993 | Schatz et al. . | |
| 5,510,240 | 4/1996 | Lam et al. | 435/7.1 |

FOREIGN PATENT DOCUMENTS

| | | |
|---|---|---|
| WO84/03564 | 9/1984 | WIPO . |
| WO90/05785 | 5/1990 | WIPO . |
| WO90/15070 | 12/1990 | WIPO . |
| WO91/05058 | 4/1991 | WIPO . |
| WO91/17271 | 11/1991 | WIPO . |
| WO91/18980 | 12/1991 | WIPO . |
| WO91/19818 | 12/1991 | WIPO . |
| WO92/00091 | 1/1992 | WIPO . |
| WO92/02536 | 2/1992 | WIPO . |
| WO92/05258 | 4/1992 | WIPO . |
| WO92/10092 | 6/1992 | WIPO . |
| WO92/14843 | 9/1992 | WIPO . |
| WO93/06121 | 4/1993 | WIPO . |
| WO93/08278 | 4/1993 | WIPO . |

OTHER PUBLICATIONS

Barbas et al. (1991), "Assembly of combinatorial antibodies libraries on phage surfaces: The gene III site,"Proc. Natl. Acad. Sci. USA 88:7978–7982.
Beaudry and Joyce (1992), "Directed evolution of an RNA enzyme," Science 257:635–641.
Dower and Fodor (1991), "The search for molecular diversity (II): Recombinant and synthetic randomized peptide libraries," Ann. Rep. Med. Chem. 26:271–280.
Eckert and Kunkel (1991), "DNA polymerase fidelity and the polymerase chain reaction," in PCR methods and applications, pp. 17–24.
Ellington and Szostak (1990), "In vitro selection of RNA molecules that bind specific ligands," Nature 346: 818–822.
Fodor et al. (1991), "Light–directed spatially addressable parallel chemical synthesis," Science 767–773.
Harlow et al. (1988), "Antibodies, A Laboratory Manual," Cold Spring Harbor, NY, pp. 496–497.
Mattila et al. (1991), "Fidelity of DNA synthesis by the *Thermococcus litoralis* DNA polymerase—an extremely heat stable enzyme with proofreading activity," Nucleic Acids Res. 19:4967–4973.
Nicholls et al. (1993), "An improved method for generating single–chain antibodies from hybridomas," J. Immunol. Methods 165:81–91.
Spirin et al. (1988), "A continuous cell–free translation system capable of producing polypeptides in high yields," Science 242:1162–1164.
Thiesen and Bach (1990), "Target detection assay (TDA):a versatile procedure to determine DNA binding sites as demonstrated on SP1 protein," Nucleic Acids Res. 18:3203–3209.
Tuerk and Gold (1990), Systematic evolution of ligands by exponential enrichment:RNA ligands to bacteriophage T4 DNA polymerase, Science 249:505–510.

*Primary Examiner*—Donna C. Wortman
*Attorney, Agent, or Firm*—Lauren L. Stevens; Tracy J. Dunn

[57] ABSTRACT

Improved methods and novel compositions for identifying peptides and single-chain antibodies that bind to predetermined receptors or epitopes. Such peptides and antibodies are identified by improved and novel methods for affinity screening of polysomes displaying nascent peptides.

4 Claims, 8 Drawing Sheets

```
       NdeI                          EcoRI
     CATATGGCTCGTCAGTTCAAAGTTGTTACCGAATTCTCCGGCAGCGGTTC  50
   1   M  A  R  Q  F  K  V  V  T  E  F  S  G  S  G  S

CGGCAGCGGTTCCGGCAGCGGTTCCGGCAGCGGTTCCGGCAGCGGTTCCG  100
  17   G  S  G  S  G  S  G  S  G  S  G  S  G  S  G  S
                             BamHI
     GCAGCGGTTCCGGCAGCGGTGGATCCTCGGCAGCGGTTCCGGCAGCGGTT  150
  34   S  G  S  G  S  G  G  S  S  A  A  V  P  A  A  V

CCGGCAGCGGTTCCGGCAGCGGTTCCGGCAGCGGTTCCGGCAGCGGTTCC  200
  50  P  A  A  V  P  A  A  V  P  A  A  V  P  A  A  V  P
           SalI
     GGCAGCGGTGTCGACAGAAGAAGGAGAAGGAGAAGGAGAAGGAGAAGGAC  250
  67   A  A  V  S  T  E  E  G  E  G  E  G  E  G  E  G  R
                                HindIII
     GACAGGCGACACGCAGGCAGCAGGCGCCAAGCTT                 284
  84   Q  A  T  R  R  Q  Q  A  P  S
```

FIG. 1.

```
DNA POOL
              M  A  S    X10        G  T  Q  G  V  G
    ...GGAGATATACATATGGCTAGC(NNK)10GGTACCCAGGGCGTTGGA...
                        NheI          KpnI
    PILL PROCESSING SITE
                        ↓
    S  H  S  M  A  S                   G  T  G  G  G  G  S
    TCTCACTCCATGGCTAGCTAATAGTGGCCAGGATAGGTACCGGCGGTGGCGGCAGT
              NheI           MscI        KpnI
```

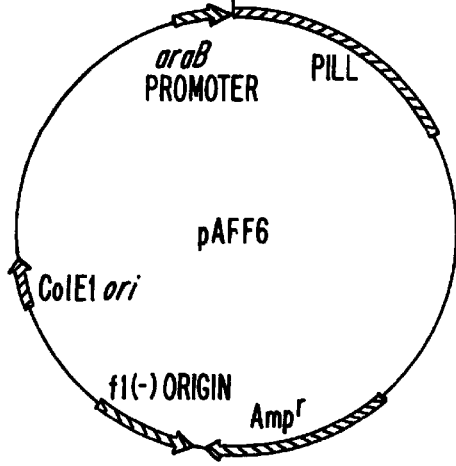

FIG. 4.

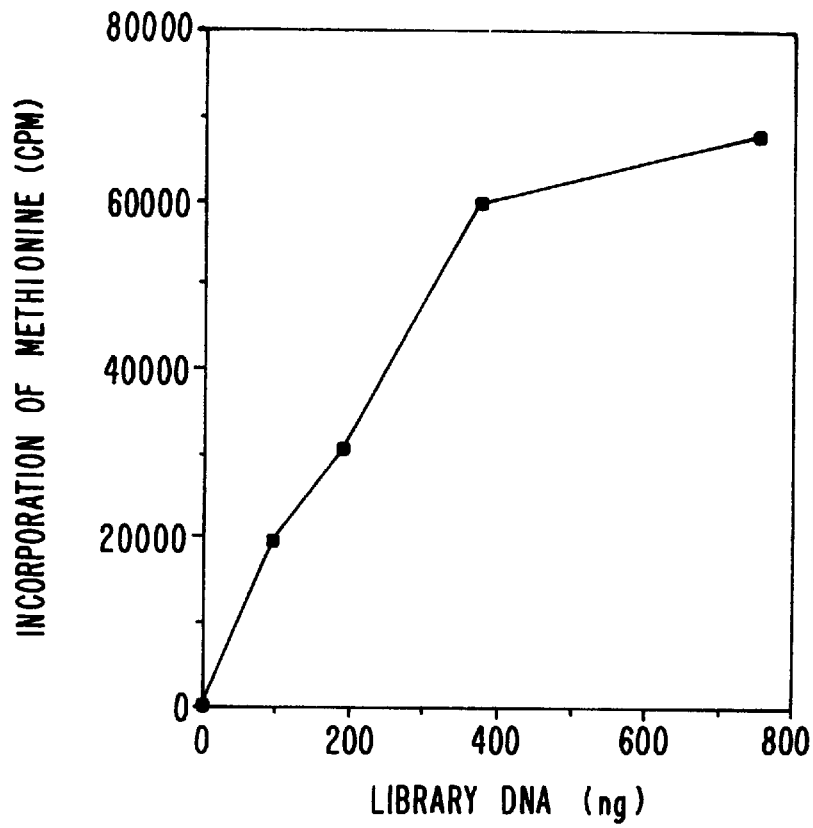
FIG. 5.
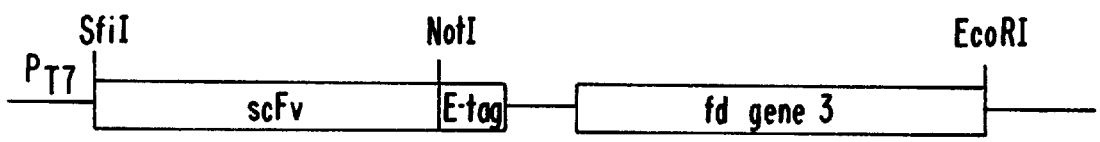
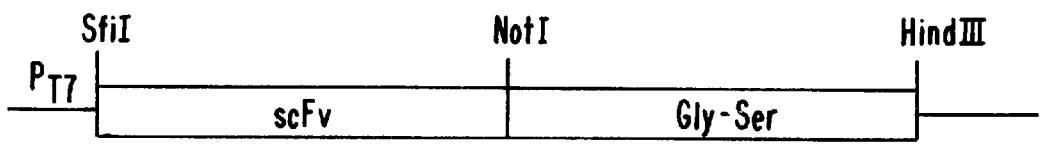
FIG. 7.

|  |  |  |  |  |  |  |  |  |  |  |  |  |  |  | IC$_{50}$ (nM) |
|---|---|---|---|---|---|---|---|---|---|---|---|---|---|---|---|
| DYNORPHIN B |  |  | Y | G | G | F | L | R | R Q F K U U | T |  |  |  |  | 0.29 ± 0.05 |

ROUND FREQUENCY

Round 2:
- 1: K S L W | R P F A Q U |
- 1:   W Q T | R R F S U A | S

Round 3:
- 1:     L | R E F R C V | M Y M    100 ± 39
- 3[a]: H N E G I | R M F R V V | V
- 1:    Y L | R P F R V T | F V
- 1:   N H W | R P F K T V | I Round 4:
- 3[b]: P I M | R S F K V V | L      7.2 ± 0.75
- 1:    Y | R I F K I I | Q P T   19 ± 1.2
- 2[c]:   D | R Q L F S I C | T V D H   140 ± 41
- 1:   S V | R L P F Y K C V | V C P S
- 1:   T K | R L Y F R H V V G | Q P
- 1: G M Y D E | R R P F R H M U U G T
- 1:  M T L | R R L P F F U U T
- 1:   K Y | R R P Q F S S U T | R L
- 1:   T T | R R Q F S A U U | U A N
- 1:   D R C | R R L F F R Q I U | K
- 1:  D S S R | R R L H F Q R U U
- 1:  S Y P | R R H F   U
- 1[a]: H N E G I | R M F   U Round 5:
- 5[b]: P I M | R S F K U U | L      7.2 ± 0.75
- 1: K R S | R M F K L U | U      8.0 ± 0.22
- 1: F S E | R R F S U C C | W T    110 ± 40
- 1[c]: D F | R R Q F S A C A | T C D H   140 ± 41
- 1: E F | R M F A U A | Y

FIG. 6.

SEQUENCE LISTING (1) GENERAL INFORMATION:

(iii) NUMBER OF SEQUENCES: 75

(2) INFORMATION FOR SEQ ID NO:1:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1:

Gly Gly Gly Gly Ser Gly Gly Gly Gly Ser Gly Gly Gly Gly Ser
   1               5                   10                  15

(2) INFORMATION FOR SEQ ID NO:2:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Lys Gly Phe Gly Phe Val Xaa Phe
   1               5

(2) INFORMATION FOR SEQ ID NO:3:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Arg Gly Tyr Ala Phe Val Xaa Tyr
   1               5

(2) INFORMATION FOR SEQ ID NO:4:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Leu Phe Val Gly Asn Leu
   1               5

(2) INFORMATION FOR SEQ ID NO:5:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Ile Tyr Ile Lys Gly Met
   1               5

(2) INFORMATION FOR SEQ ID NO:6:

(i) SEQUENCE CHARACTERISTICS:
    (A) LENGTH: 16 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:6:

```
Thr Arg Gln Ala Arg Arg Asn Arg Arg Arg Trp Arg Glu Arg Gln
1               5                   10                  15
```

(2) INFORMATION FOR SEQ ID NO:7:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Ala Leu Gly Ile Ser Tyr Gly Arg Lys Lys Arg Arg Gln Arg Arg
1               5                   10                  15

Pro
```

(2) INFORMATION FOR SEQ ID NO:8:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Met Asp Ala Gln Thr Arg Arg Arg Glu Arg Arg Ala Glu Lys Gln Ala
1               5                   10                  15

Gln Trp
```

(2) INFORMATION FOR SEQ ID NO:9:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Gly Thr Ala Lys Ser Arg Tyr Lys Ala Arg Arg Ala Glu Leu Ile Ala
1               5                   10                  15

Glu Arg
```

(2) INFORMATION FOR SEQ ID NO:10:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
    Gly Asn Ala Lys Thr Arg Arg His Glu Arg Arg Arg Lys Leu Ala Ile
    1               5                   10                  15

Glu Arg (2) INFORMATION FOR SEQ ID NO:11:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Met Val Lys Thr Asp
    1               5

(2) INFORMATION FOR SEQ ID NO:12:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

Met Ser Thr Ser Lys Asn Ala Asp
    1               5

(2) INFORMATION FOR SEQ ID NO:13:

(i) SEQUENCE CHARACTERISTICS:
        (A) LENGTH: 35 base pairs
        (B) TYPE: nucleic acid
        (C) STRANDEDNESS: double
        (D) TOPOLOGY: linear (xi) SEQUENCE DESCRIPTION: SEQ ID NO:13:

CATATGGCTG TTTTCAAACG TACCGTTCAG GAATC                                      35

(2) INFORMATION FOR SEQ ID NO:14:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:14:

Arg Gln Phe Lys Val Val Thr
    1               5

(2) INFORMATION FOR SEQ ID NO:15:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:15:

Val Phe Lys Arg Thr Val Gln
    1               5
```

(2) INFORMATION FOR SEQ ID NO:16:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Gly Gly Gly Ser Gly Gly Gly Ser Gly Gly Gly Gly Ser Gly
    1               5                   10                  15

Gly Gly Gly Ser Ala Ala Val Pro
                20

(2) INFORMATION FOR SEQ ID NO:17:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (xi) SEQUENCE DESCRIPTION: SEQ ID NO:17:

AAATTTCCAA CGCCCTGGGT ACCMNNMNNM NMNNMNNMNN NMNNMNNMNN MNNGCTAGCC        60

ATATGTATAT CTCCTTCTT                                                     79

(2) INFORMATION FOR SEQ ID NO:18:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:18:

ACCTGGGCCA TGGCCGGCTG GGCCGCAT                                           28

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:19:

TCTCCGGGAG CTGCATGTGT C                                                  21

(2) INFORMATION FOR SEQ ID NO:20:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:20:

ATGCGGCCCA GCCGGCCATG GCCCAGGT                                           28

(2) INFORMATION FOR SEQ ID NO:21:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:21:

CAGTTTCTGC GGCCGCACGT TTGAT                                          25

(2) INFORMATION FOR SEQ ID NO:22:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:22:

ATCAAACGTG CGGCCGCAGA AACTGTTGAA TTC                                 33

(2) INFORMATION FOR SEQ ID NO:23:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:23:

AATTGGAGGA TCGTGCATGT GAC                                            23

(2) INFORMATION FOR SEQ ID NO:24:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (xi) SEQUENCE DESCRIPTION: SEQ ID NO:24:

ACTTCGAAAT TAATACGACT CACTATAGGG AGACCACAAC GGTTTCCCTC TAGAAATAAT    60

TTTGTTTAAC TTTAAGAAGG AGATATACAT                                    90

(2) INFORMATION FOR SEQ ID NO:25:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:25:

Arg Gln Phe Lys Val Val
  1               5

(2) INFORMATION FOR SEQ ID NO:26:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:26:

Met Ala Arg Gln Phe Lys Val Val Thr
  1               5

(2) INFORMATION FOR SEQ ID NO:27:

(i) SEQUENCE CHARACTERISTICS:
        (A) LENGTH: 9 amino acids
        (B) TYPE: amino acid (C) STRANDEDNESS: single
        (D) TOPOLOGY: linear (xi) SEQUENCE DESCRIPTION: SEQ ID NO:27:

Met Ala Val Phe Lys Arg Thr Val Gln
    1               5

(2) INFORMATION FOR SEQ ID NO:28:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (xi) SEQUENCE DESCRIPTION: SEQ ID NO:28:

CATATGGGTA CCCAGGGCGT TGGTGAATTC                                          30

(2) INFORMATION FOR SEQ ID NO:29:

(i) SEQUENCE CHARACTERISTICS:
        (A) LENGTH: 174 base pairs
        (B) TYPE: nucleic acid
        (C) STRANDEDNESS: double
        (D) TOPOLOGY: linear (xi) SEQUENCE DESCRIPTION: SEQ ID NO:29:

GGATCCCAGT CGGTTGAATG TCGCCCTTAT GTCTTTGGCG CTGGTAAACC ATATGAATTT          60

TCTATTGATT GTGACAAAAT AAACTTATTC CGTGGTGTCT TTGCGTTCTT TTATATGTTG         120

CCACCTTTAT GTATGTATTT TCGACGTTTC GACGTTTGCT AACATACTGT CGAC              174

(2) INFORMATION FOR SEQ ID NO:30:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:30:

TATGGGTACC CAGGGCGTTG GTG                                                 23

(2) INFORMATION FOR SEQ ID NO:31:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:31:

GGCGCCTGCT GCCTGCGTGT CGCCTGTCGT                                          30

(2) INFORMATION FOR SEQ ID NO:32:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:32:

GATTGTGGAA GCTTGGCGCC TGCT                                                24

(2) INFORMATION FOR SEQ ID NO:33:

(i) SEQUENCE CHARACTERISTICS:
    (A) LENGTH: 51 base pairs
    (B) TYPE: nucleic acid
    (C) STRANDEDNESS: single
    (D) TOPOLOGY: linear (xi) SEQUENCE DESCRIPTION: SEQ ID NO:33:

ACTTCGAAAT TAATACGACT CACTATAGGG AGACCACAAC GGTTTCCCTC T            51

(2) INFORMATION FOR SEQ ID NO:34:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:34:

GGCGCCTGCT GCCTGCGTGT CGCCTGTCGT                                    30

(2) INFORMATION FOR SEQ ID NO:35:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:35:

His Asn Glu Gly Ile Arg Met Phe Arg Val Val
    1               5                   10

(2) INFORMATION FOR SEQ ID NO:36:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:36:

Gly Met Tyr Glu Thr Arg Leu Phe His Val Gly
    1               5                   10

(2) INFORMATION FOR SEQ ID NO:37:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:37:

Phe Ser Glu Arg Arg Phe Ser Val Cys Trp
    1               5                   10

(2) INFORMATION FOR SEQ ID NO:38:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:38:

His Asn Glu Gly Ile Arg Met Phe Arg Val Val
    1               5                   10

(2) INFORMATION FOR SEQ ID NO:39:

(i) SEQUENCE CHARACTERISTICS:
        (A) LENGTH: 11 amino acids
        (B) TYPE: amino acid
        (C) STRANDEDNESS: double
        (D) TOPOLOGY: linear (xi) SEQUENCE DESCRIPTION: SEQ ID NO:39:

Gly Met Tyr Glu Thr Arg Leu Phe His Val Gly
    1             5               10

(2) INFORMATION FOR SEQ ID NO:40:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:40:

Phe Ser Glu Arg Arg Phe Ser Val Cys Trp
    1             5              10

(2) INFORMATION FOR SEQ ID NO:41:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:41:

Pro Ile Met Arg Ser Phe Lys Val Val Leu
    1             5              10

(2) INFORMATION FOR SEQ ID NO:42:

(i) SEQUENCE CHARACTERISTICS:
        (A) LENGTH: 284 base pairs
        (B) TYPE: nucleic acid
        (C) STRANDEDNESS: double
        (D) TOPOLOGY: linear (xi) SEQUENCE DESCRIPTION: SEQ ID NO:42:

```
CATATGGCTC GTCAGTTCAA AGTTGTTACC GAATTCTCCG GCAGCGGTTC CGGCAGCGGT    60

TCCGGCAGCG GTTCCGGCAG CGGTTCCGGC AGCGGTTCCG GCAGCGGTTC CGGCAGCGGT   120

GGATCCTCGG CAGCGGTTCC GGCAGCGGTT CCGGCAGCGG TTCCGGCAGC GGTTCCGGCA   180

GCGGTTCCGG CAGCGGTTCC GGCAGCGGTG TCGACAGAAG AAGGAGAAGG AGAAGGAGAA   240

GGAGAAGGAC GACAGGCGAC ACGCAGGCAG CAGGCGCCAA GCTT                    284
```

(2) INFORMATION FOR SEQ ID NO:43:

(i) SEQUENCE CHARACTERISTICS:
        (A) LENGTH: 93 amino acids
        (B) TYPE: amino acid
        (C) STRANDEDNESS: unknown
        (D) TOPOLOGY: unknown (xi) SEQUENCE DESCRIPTION: SEQ ID NO:43:

Met Ala Arg Gln Phe Lys Val Val Thr Glu Phe Ser Gly Ser Gly Ser
    1             5               10               15

Gly Ser Gly Ser Gly Ser Gly Ser Gly Ser Gly Ser Gly Ser Gly Ser
                    20                      25                   30

```
        Gly Ser Gly Ser Gly Gly Ser Ser Ala Ala Val Pro Ala Ala
             35              40              45

Val Pro Ala Ala Val Pro Ala Ala Val Pro Ala Ala Val Pro Ala Ala
         50                  55                  60

Val Pro Ala Ala Val Ser Thr Glu Glu Gly Glu Gly Glu Gly
         65                  70              75              80

Glu Gly Arg Gln Ala Thr Arg Arg Gln Gln Ala Pro Ser
                     85                  90
```

(2) INFORMATION FOR SEQ ID NO:44:

(i) SEQUENCE CHARACTERISTICS:
        (A) LENGTH: 146 base pairs
        (B) TYPE: nucleic acid
        (C) STRANDEDNESS: single
        (D) TOPOLOGY: linear (xi) SEQUENCE DESCRIPTION: SEQ ID NO:44:

```
ACTTCGAAAT TAATACGACT CACTATAGGG AGACCACAAC GGTTTCCCTC TAGAAATAAT      60

TTTGTTTAAC TTTAAGAAGG AGATATACAT ATGGCTAGCN NKNNKNNKNN KNNKNNKNNK     120

NNKNNKNNKG GTACCCAGGG CGTTGG                                         146
```

(2) INFORMATION FOR SEQ ID NO:45:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 13
        (D) OTHER INFORMATION: /note= ""N represents the Gly-Ser
            region shown in Fig. 3""

(xi) SEQUENCE DESCRIPTION: SEQ ID NO:45:

```
CCAGGGCGGT GGNCCACAAT CGTGG                                           25
```

(2) INFORMATION FOR SEQ ID NO:46:

(i) SEQUENCE CHARACTERISTICS:
        (A) LENGTH: 19 amino acids
        (B) TYPE: amino acid
        (C) STRANDEDNESS: unknown
        (D) TOPOLOGY: unknown (xi) SEQUENCE DESCRIPTION: SEQ ID NO:46:

```
    Met Ala Ser Xaa Xaa Xaa Xaa Xaa Xaa Xaa Xaa Xaa Xaa Gly Thr Gln
     1               5                  10                  15

Gly Val Gly
```

(2) INFORMATION FOR SEQ ID NO:47:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (xi) SEQUENCE DESCRIPTION: SEQ ID NO:47:

```
TCTCACTCCA TGGCTAGCTA ATAGTGGCCA GGATAGGTAC CGGCGGTGGC GGCAGT          56
```

(2) INFORMATION FOR SEQ ID NO:48:

(i) SEQUENCE CHARACTERISTICS:
        (A) LENGTH: 6 amino acids
        (B) TYPE: amino acid
        (C) STRANDEDNESS: unknown
        (D) TOPOLOGY: unknown (xi) SEQUENCE DESCRIPTION: SEQ ID NO:48:

```
Ser His Ser Met Ala Ser
1               5
```

(2) INFORMATION FOR SEQ ID NO:49:

(i) SEQUENCE CHARACTERISTICS:
        (A) LENGTH: 7 amino acids
        (B) TYPE: amino acid
        (C) STRANDEDNESS: unknown
        (D) TOPOLOGY: unknown (xi) SEQUENCE DESCRIPTION: SEQ ID NO:49:

```
Gly Thr Gly Gly Gly Gly Ser
1               5
```

(2) INFORMATION FOR SEQ ID NO:50:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:50:

```
Tyr Gly Gly Phe Leu Arg Arg Gln Phe Lys Val Val Thr
1               5                   10
```

(2) INFORMATION FOR SEQ ID NO:51:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:51:

```
Lys Ser Leu Trp Arg Pro Phe Ala Gln Val
1               5                   10
```

(2) INFORMATION FOR SEQ ID NO:52:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:52:

```
Trp Gln Thr Arg Arg Phe Ser Val Ala Ser
1               5                   10
```

(2) INFORMATION FOR SEQ ID NO:53:

(i) SEQUENCE CHARACTERISTICS:
        (A) LENGTH: 10 amino acids

```
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:53:

Leu Arg Glu Phe Arg Cys Val Met Tyr Met
    1               5                   10

(2) INFORMATION FOR SEQ ID NO:54:

(i) SEQUENCE CHARACTERISTICS:
        (A) LENGTH: 11 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:54:

His Asn Glu Gly Ile Arg Met Phe Arg Val Val
    1               5                   10

(2) INFORMATION FOR SEQ ID NO:55:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:55:

Tyr Leu Arg Pro Phe Arg Val Thr Phe Val
    1               5                   10

(2) INFORMATION FOR SEQ ID NO:56:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:56:

Asn His Trp Arg Pro Phe Lys Thr Val Ile
    1               5                   10

(2) INFORMATION FOR SEQ ID NO:57:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:57:

Pro Ile Met Arg Ser Phe Lys Val Val Leu
    1               5                   10

(2) INFORMATION FOR SEQ ID NO:58:

(i) SEQUENCE CHARACTERISTICS:
        (A) LENGTH: 10 amino acids
```

(B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:58:

Tyr Arg Ile Phe Lys Ile Ile Gln Pro Thr
    1               5                   10

(2) INFORMATION FOR SEQ ID NO:59:

(i) SEQUENCE CHARACTERISTICS:
            (A) LENGTH: 10 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:59:

Asp Arg Gln Phe Ser Ile Cys Thr Asp His
    1               5                   10

(2) INFORMATION FOR SEQ ID NO:60:

(i) SEQUENCE CHARACTERISTICS:
            (A) LENGTH: 10 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:60:

Ser Arg Leu Phe Lys Cys Val Val Cys Ser
    1               5                   10

(2) INFORMATION FOR SEQ ID NO:61:

(i) SEQUENCE CHARACTERISTICS:
            (A) LENGTH: 10 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:61:

Asp Val Arg Pro Tyr Arg Leu Val Gln Pro
    1               5                   10

(2) INFORMATION FOR SEQ ID NO:62:

(i) SEQUENCE CHARACTERISTICS:
            (A) LENGTH: 11 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:62:

Gly Met Tyr Glu Thr Arg Leu Phe His Val Gly
    1               5                   10

(2) INFORMATION FOR SEQ ID NO:63:

(i) SEQUENCE CHARACTERISTICS:
            (A) LENGTH: 10 amino acids

```
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:63:

Met Thr Leu Lys Arg Pro Phe Met Val Thr
    1               5                   10

(2) INFORMATION FOR SEQ ID NO:64:

(i) SEQUENCE CHARACTERISTICS:
            (A) LENGTH: 10 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:64:

Asp Tyr Arg Gln Phe Ser Val Thr Arg Leu
    1               5                   10

(2) INFORMATION FOR SEQ ID NO:65:

(i) SEQUENCE CHARACTERISTICS:
            (A) LENGTH: 10 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:65:

Arg Thr Arg Gln Phe Ser Val Val Val Asn
    1               5                   10

(2) INFORMATION FOR SEQ ID NO:66:

(i) SEQUENCE CHARACTERISTICS:
            (A) LENGTH: 10 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:66:

Ser Thr Arg Leu Phe Ala Gln Val Ala Lys
    1               5                   10

(2) INFORMATION FOR SEQ ID NO:67:

(i) SEQUENCE CHARACTERISTICS:
            (A) LENGTH: 10 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:67:

Asp Ser Ser Cys Arg Leu Phe Arg Ile Val
    1               5                   10

(2) INFORMATION FOR SEQ ID NO:68:

(i) SEQUENCE CHARACTERISTICS:
            (A) LENGTH: 10 amino acids
```

(B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:68:

Ser Tyr Pro Arg Arg His Phe Gln Ile Val
    1               5                   10

(2) INFORMATION FOR SEQ ID NO:69:

(i) SEQUENCE CHARACTERISTICS:
        (A) LENGTH: 11 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:69:

His Asn Glu Gly Ile Arg Met Phe Arg Val Val
    1               5                   10

(2) INFORMATION FOR SEQ ID NO:70:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:70:

Pro Ile Met Arg Ser Phe Lys Val Val Leu
    1               5                   10

(2) INFORMATION FOR SEQ ID NO:71:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:71:

Lys Arg Phe Arg Met Phe Lys Leu Val Val
    1               5                   10

(2) INFORMATION FOR SEQ ID NO:72:

(i) SEQUENCE CHARACTERISTICS:
        (A) LENGTH: 10 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:72:

Phe Ser Glu Arg Arg Phe Ser Val Cys Trp
    1               5                   10

(2) INFORMATION FOR SEQ ID NO:73:

(i) SEQUENCE CHARACTERISTICS:
        (A) LENGTH: 10 amino acids

```
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:73:

Asp Arg Gln Phe Ser Ile Cys Thr Asp His
      1               5                   10

(2) INFORMATION FOR SEQ ID NO:74:

(i) SEQUENCE CHARACTERISTICS:
            (A) LENGTH: 10 amino acids
            (B) TYPE: amino acid
            (C) STRANDEDNESS: unknown
            (D) TOPOLOGY: unknown (ii) MOLECULE TYPE: peptide (xi) SEQUENCE DESCRIPTION: SEQ ID NO:74:

Glu Phe Arg Met Phe Ala Val Ala Cys Tyr
      1               5                   10

(2) INFORMATION FOR SEQ ID NO:75:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:75:

Gly Gly Gly Gly Ser
      1               5
```

IN VITRO PEPTIDE AND ANTIBODY DISPLAY LIBRARIES

This application is a continuation of application Ser. No. 08/586,176, filed Jan. 17, 1996, now abandoned, which is a continuation-in-part of Application Number PCT/US94/12206, with an international filing date of Oct. 25, 1994, now abandoned, which is a continuation-in-part of application Ser. No. 08/300262, filed Sep. 2, 1994, now abandoned, which is a continuation-in-part of application Ser. No. 08/144775, filed Oct. 29, 1993, now abandoned.

FIELD OF THE INVENTION

The invention relates to methods and compositions for generating and screening combinatorial libraries of (1) displayed peptides and/or (2) displayed recombinant single-chain antibodies comprising variable region sequences encoded by natural or artificial variable region encoding sequences which are expressed on polysomes in an in vitro coupled transcription/translation system to facilitate screening.

BACKGROUND

Antibody Display and Screening Methods

Various molecular genetic approaches have been devised to capture the vast immunological repertoire represented by the extremely large number of distinct variable regions which can be present in immunoglobulin chains. The naturally-occurring germline immunoglobulin heavy chain locus is composed of separate tandem arrays of variable (V) segment genes located upstream of a tandem array of diversity (D) segment genes, which are themselves located upstream of a tandem array of joining (a) region genes, which are located upstream of the constant ($C_H$) region genes. During B lymphocyte development, V-D-J rearrangement occurs wherein a heavy chain variable region gene ($V_H$) is formed by rearrangement to form a fused D-J segment followed by rearrangement with a V segment to form a V-D-J joined product gene which, if productively rearranged, encodes a functional variable region ($V_H$) of a heavy chain. Similarly, light chain loci rearrange one of several V segments with one of several J segments to form a gene encoding the variable region ($V_L$) of a light chain.

The vast repertoire of variable regions possible in immunoglobulins derives in part from the numerous combinatorial possibilities of joining V and J segments (and, in the case of heavy chain loci, D segments) during rearrangement in B cell development. Additional sequence diversity in the heavy chain variable regions arises from non-uniform rearrangements of the D segments during V-D-J joining and from N region addition. Further, antigen-selection of specific B cell clones selects for higher affinity variants having nongermline mutations in one or both of the heavy and light chain variable regions; a phenomenon referred to as "affinity maturation" or "affinity sharpening". Typically, these "affinity sharpening" mutations cluster in specific areas of the variable region, most commonly in the complementarity-determining regions (CDRs).

In order to overcome many of the limitations in producing and identifying high-affinity immunoglobulins through antigen-stimulated B cell development (i.e., immunization), various prokaryotic expression systems have been developed that can be manipulated to produce combinatorial antibody libraries which may be screened for high-affinity antibodies to specific antigens. Recent advances in the expression of antibodies in *Escherichia coli* and bacteriophage systems (see, "Alternative Peptide Display Methods", infra) have raised the possibility that virtually any specificity can be obtained by either cloning antibody genes from characterized hybridomas or by de novo selection using antibody gene libraries (e.g., from Ig CDNA).

Combinatorial libraries of antibodies have been generated in bacteriophage lambda expression systems which may be screened as bacteriophage plaques or as colonies of lysogens (Huse et al. (1989) *Science* 246: 1275; Caton and Koprowski (1990) *Proc. Natl. Acad. Sci. (U.S.A.)* 87: 6450; Mullinax et al (1990) *Proc. Natl. Acad. Sci. (U.S.A.)* 87: 8095; Persson et al. (1991) *Proc. Natl. Acad. Sci. (U.S.A.* 88: 2432). Unfortunately, lambda-based combinatorial antibody expression libraries are not suited for screening of large numbers of library members (i.e., greater than $10^8$–$10^9$ members) nor are lambda-based combinatorial libraries suitable for selective enrichment by antigen affinity chromatography.

Recently, systems in which diverse peptide sequences are displayed on the surface of filamentous bacteriophage (Scott and Smith (1990) *Science* 249 : 386) have proven attractive for forming various combinations of heavy chain variable regions and light chain variable regions (and the polynucleotide sequences encoding them) for in vitro selection and enrichment by binding to specific antigen. Polynucleotide sequences encoding heavy and light chain variable regions are linked to gene fragments that encode signals that direct them to the periplasmic space of *E. coli* and the resultant "antibodies" are displayed on the surface of bacteriophage, typically as fusions to bacteriophage coat proteins (edg., pIII or pVIII). Variable region fragments of immunoglobulins (either Fv or Fab) can be displayed externally on phage capsids (phagebodies) and recombinant phage are selected for by binding to immobilized antigen.

Various embodiments of bacteriophage antibody display libraries and lambda phage expression libraries have been described (Kang et al. (1991) *Proc. Natl. Acad. Sci. (U.S.A.)* 88: 4363; Clackson et al. (1991) *Nature* 352: 624; McCafferty et al. (1990) *Nature* 348: 552; Burton et al. (1991) *Proc. Natl. Acad. Sci. (U.S.A.)* 88: 10134; Hoogenboom et al. (1991) *Nucleic Acids Res.* 19: 4133; Chang et al. (1991) *J. Immunol.* 147: 3610; Breitling et al. (1991) *Gene* 104: 147; Marks et al. (1991) *J. Mol. Biol.* 222: 581; Barbas et al. (1992) *Proc. Natl. Acad. Sci. (U.S.A.)* 89: 4457; Hawkins and Winter (1992) *J. Immunol.* 22: 867; Marks et al. (1992) *Biotechnology* 10: 779; Marks et al. (1992) *J. Biol. Chem.* 267: 16007; Lowman et al (1991) *Biochemistry* 30: 10832; Lerner et al. (1992) *Science* 258: 1313, incorporated herein by reference).

One particularly advantageous approach has been the use of so-called single-chain fragment variable (scFv) libraries (Marks et al. (1992) *Biotechnology* 10: 779; Winter G and Milstein C (1991) *Nature* 349: 293; Clackson et al. (1991) op.cit.; Harks et al. (1991) *J. Mol. Biol.* 222: 581; Chaudhary et al. (1990) *Proc. Natl. Acad. Sci. (USA)* 87: 1066; Chiswell et al. (1992) *TIBTECH* 10: 80; McCafferty et al. (1990) op.cit.; and Huston et al. (1988) *Proc. Natl. Acad. Sci. (USA)* 85:, 5879). Various embodiments of scFv libraries displayed on bacteriophage coat proteins have been described.

Beginning in 1988, single-chain analogues of Fv fragments and their fusion proteins have been reliably generated by antibody engineering methods. The first step generally involves obtaining the genes encoding $V_H$ and $V_L$ domains with desired binding properties; these V genes may be isolated from a specific hybridoma cell line, selected from a combinatorial V-gene library, or made by V gene synthesis. The single-chain Fv is formed by connecting the component V genes with an oligonucleotide that encodes an appropriately designed linker peptide, such as (Gly-Gly-Gly-Gly-Ser)$_3$ (SEQ ID NO:1) or equivalent linker peptide(s). The linker bridges the C-terminus of the first V region and N-terminus of the second, ordered as either $V_H$-linker-$V_L$ or $V_L$-linker-$V_H$. In principle, the scFv binding site can faithfully replicate both the affinity and specificity of its parent antibody combining site.

Thus, scFv fragments are comprised of $V_H$ and $V_L$ domains linked into a single polypeptide chain by a flexible linker peptide. After the scFv genes are assembled, they are cloned into a phagemid and expressed at the tip of the M13 phage (or similar filamentous bacteriophage) as fusion proteins with the bacteriophage pIII (gene 3) coat protein. Enriching for phage expressing an antibody of interest is accomplished by panning the recombinant phage displaying a population scFv for binding to a predetermined epitope (e.g., target antigen, receptor).

Various methods have been reported for increasing the combinatorial diversity of a scFv library to broaden the repertoire of binding species (idiotype spectrum). The use of PCR has permitted the variable regions to be rapidly cloned either from a specific hybridoma source or as a gene library from non-immunized cells, affording combinatorial diversity in the assortment of $V_H$ and $V_L$ cassettes which can be combined. Furthermore, the $V_H$ and $V_L$ cassettes can themselves be diversified, such as by random, pseudorandom, or directed mutagenesis. Typically, $V_H$ and $V_L$ cassettes are diversified in or near the complementarity-determining regions (CDRs), often the third CDR, CDR3. Enzymatic inverse PCR mutagenesis has been shown to be a simple and reliable method for constructing relatively large libraries of scFv site-directed mutants (Stemmer et al. (1993) *Biotechniques* 14: 256), as has error-prone PCR and chemical mutagenesis (Deng et al. (1994) *J. Biol. Chem.* 269: 9533). Riechmann et al. (1993) *Biochemistry* 32: 8848 showed semirational design of an antibody scFv fragment using site-directed randomization by degenerate oligonucleotide PCR and subsequent phage display of the resultant scFv mutants. Barbas et al. (1992) op. cit. attempted to circumvent the problem of limited repertoire sizes resulting from using biased variable region sequences by randomizing the sequence in a synthetic CDR region of a human tetanus toxoid-binding Fab.

CDR randomization has the potential to create approximately $1 \times 10^{20}$ CDRs for the heavy chain CDR3 alone, and a roughly similar number of variants of the heavy chain CDR1 and CDR2, and light chain CDR1–3 variants. Taken individually or together, the combinatorics of CDR randomization of heavy and/or light chains requires generating a prohibitive number of bacteriophage clones to produce a clone library representing all possible combinations, the vast majority of which will be non-binding. Generation of such large numbers of primary transformants is not feasible with current transformation technology and bacteriophage display systems. For example, Barbas et al. (1992) op. cit. only generated $5 \times 10^7$ transformants, which represents only a tiny fraction of the potential diversity of a library of thoroughly randomized CDRs.

A further limitation of present bacteriophage scFv display systems is produced by the constraints of the prokaryotic systems used to generate the bacteriophage libraries. For example, prokaryotic in vivo display systems often suffer from defective secretion, rapid proteolysis, and/or formation of insoluble inclusion bodies containing the "displayed" scFv due to various factors, including high level expression (Nallender WD and Voss EW (1994) *J. Biol. Chem.* 269: 199).

Despite these substantial limitations, bacteriophage display of scFv have already yielded a variety of useful antibodies and antibody fusion proteins. A bispecific single chain antibody has been shown to mediate efficient tumor cell lysis (Gruber et al. (1994) *J. Immunol.* 152: 5368). Intracellular expression of an anti-Rev scFv has been shown to inhibit HIV-1 virus replication in vitro (Duan et al. (1994) *Proc. Natl. Acad. Sci. (USA)* 91: 5075), and intracellular expression of an anti-p21ras scFv has been shown to inhibit meiotic maturation of Xenopus oocytes (Biocca et al. (1993) *Biochem. Biophys. Res. Commun.* 197: 422. Recombinant scFv which can be used to diagnose HIV infection have also been reported, demonstrating the diagnostic utility of scFv (Lilley et al. (1994) *J. Immunol. Meth.* 171: 211). Fusion proteins wherein an scFv is linked to a second polypeptide, such as a toxin or fibrinolytic activator protein, have also been reported (Holvost et al. (1992) *Eur. J. Biochem.* 210: 945; Nicholls et al. (1993) *J. Biol. Chem.* 268: 5302).

If it were possible to generate scFv libraries having broader antibody diversity and overcoming many of the limitations of a prokaryotic in vivo display system, the number and quality of scFv antibodies suitable for therapeutic and diagnostic use could be vastly improved.

Based on the foregoing, it is evident that there is a need in the art for methods to generate scFv antibody libraries which comprise a broader diversity and which are not limited by the fundamental constraints of in vivo display systems. The present invention fulfills this need and others.

Alternative Peptide Display Methods

An increasingly important aspect of biopharmaceutical drug development and molecular biology is the identification of peptide structures, including the primary amino acid sequences, of peptides or peptidomimetics that interact with biological macromolecules. One method of identifying peptides that possess a desired structure or functional property, such as binding to a predetermined biological macromolecule (e.g., a receptor), involves the screening of a large library or peptides for individual library members which possess the desired structure or functional property conferred by the amino acid sequence of the peptide.

Several approaches to generating and screening large libraries of random or pseudorandom peptide sequences suitable for screening, selection, and identification of desired individual library members have been proposed in the art. One category of peptide library is produced by direct chemical synthesis of the library members. One early method involves the synthesis of peptides on a set of pins or rods, such as is described in PCT patent publication Nos. 84/03564 and 84/03564. A similar method involving peptide synthesis on beads, which forms a peptide library in which each bead is an individual library member, is described in U.S. Pat. No. 4,631,211, and a related method is described in PCT patent publication No. 92/00091. A significant improvement of the bead-based methods involves tagging each bead with a unique identifier tag, such as an oligonucleotide, so as to facilitate identification of the amino acid sequence of each library member. These improved bead-based methods are described in PCT publication No. 93/06121.

Another chemical synthesis method involves the synthesis of arrays of peptides (or peptidomimetics) on a surface in a manner that places each distinct library member (e.g.

unique peptide sequence) at a discrete, predefined location in the array. The identity of each library member is determined by its spatial location in the array. The locations in the array where binding interactions between a predetermined molecule (erg, a receptor) and reactive library members occur is determined, thereby identifying the sequences of the reactive library members on the basis of spatial location. These methods are described in U.S. Pat. No. 5,143,854; PCT patent publication Nos. 90/15070 and 92/10092; Fodor et al. (1991) Science 251: 767; and Dower and Fodor (1991) Ann. Rep. Med. Chem. 26: 271.

In addition to the direct chemical synthesis methods for generating peptide libraries, several recombinant DNA methods also have been reported. One type involves the display of a peptide sequence, antibody, or other protein on the surface of a bacteriophage particle or cell. Generally, in these methods each bacteriophage particle or cell serves as an individual library member displaying a single species of displayed peptide in addition to the natural bacteriophage or cell protein sequences. Each bacteriophage or cell contains the nucleotide sequence information encoding the particular displayed peptide sequence; thus, the displayed peptide sequence can be ascertained by nucleotide sequence determination of an isolated library member.

A well-known peptide display method involves the presentation of a peptide sequence on the surface of a filamentous bacteriophage, typically as a fusion with a bacteriophage coat protein. The bacteriophage library can be incubated with an immobilized, predetermined macromolecule or small molecule (e.g., a receptor) so that bacteriophage particles which present a peptide sequence that binds to the immobilized macromolecule can be differentially partitioned from those that do not present peptide sequences that bind to the predetermined macromolecule. The bacteriophage particles (i.e., library members) which are bound to the immobilized macromolecule are then recovered and replicated to amplify the selected bacteriophage subpopulation for a subsequent round of affinity enrichment and phage replication. After several rounds of affinity enrichment and phage replication, the bacteriophage library members that are thus selected are isolated and the nucleotide sequence encoding the displayed peptide sequence is determined, thereby identifying the sequence(s) of peptides that bind to the predetermined macromolecule (e.g., receptor). Such methods are further described in PCT patent publication Nos. 91/17271, 91/18980, and 91/19818 and 93/08278.

The latter PCT publication describes a recombinant DNA method for the display of peptide ligands that involves the production of a library of fusion proteins with each fusion protein composed of a first polypeptide portion, typically comprising a variable sequence, that is available for potential binding to a predetermined macromolecule, and a second polypeptide portion that binds to DNA, such as the DNA vector encoding the individual fusion protein. When transformed host cells are cultured under conditions that allow for expression of the fusion protein, the fusion protein binds to the DNA vector encoding it. Upon lysis of the host cell, the fusion protein/vector DNA complexes can be screened against a predetermined macromolecule in much the same way as bacteriophage particles are screened in the phage-based display system, with the replication and sequencing of the DNA vectors in the selected fusion protein/vector DNA complexes serving as the basis for identification of the selected library peptide sequence(s).

Other systems for generating libraries of peptides and like polymers have aspects of both the recombinant and in vitro chemical synthesis methods. In these hybrid methods, cell-free enzymatic machinery is employed to accomplish the in vitro synthesis of the library members (i.e., peptides or polynucleotides). In one type of method, RNA molecules with the ability to bind a predetermined protein or a predetermined dye molecule were selected by alternate rounds of selection and PCR amplification (Tuerk and Gold (1990) Science 249: 505; Ellington and Szostak (1990) Nature 346: 818). A similar technique was used to identify DNA sequences which bind a predetermined human transcription factor (Thiesen and Bach (1990) Nucleic Acids Res. 18: 3203; Beaudry and Joyce (1992) Science 257; 635; PCT patent publication Nos. 92/05258 and 92/14843) In a similar fashion, the technique of in vitro translation has been used to synthesize proteins of interest and has been proposed as a method for generating large libraries of peptides. These methods which rely upon in vitro translation, generally comprising stabilized polysome complexes, are described further in PCT patent publication Nos. 88/08453, 90/05785, 90/07003, 91/02076, 91/05058, and 92/02536. Applicants have described methods in which library members comprise a fusion protein having a first polypeptide portion with DNA binding activity and a second polypeptide portion having the library member unique peptide sequence; such methods are suitable for use in cell-free in vitro selection formats, among others.

Although the various methods described above for generating and screening peptide libraries have been reported, there exists a need for additional methods for making peptide libraries, selecting desired library members, and identifying the peptide sequence(s) of said desired library members. Alternative methods which (1) increase the primary peptide library size, (2) facilitate rapid, efficient, and inexpensive library construction and screening, or (3) possess other advantageous features would meet a need in the art for improved peptide library methods. For instance, some of the in vitro translation-based methods suffer from the instability of the polysome complexes, which leads to poor recovery of the nucleic acids that encode the peptide sequence of interest. Additionally, polysomes are relatively large and the resultant slower diffusion in solvent leads to relatively inefficient capture of polysomes by immobilized ligand/receptor during screening. The recombinant methods described above can only be used to produce libraries of compounds composed of subunits and library members capable of being produced by the host cell, and thus for example are not suited for producing library members comprising non-naturally occurring amino acids and peptide sequences which adversely affect the host cell, among other sequences. The present invention meets the need for advanced methods for generating and screening such desirable peptide libraries, and in one aspect provides libraries of single-chain antibodies displayed on nascent polysomes.

All publications and patent applications herein are incorporated by reference to the same extent as if each individual publication or patent application was specifically and individually indicated to be incorporated by reference.

SUMMARY OF THE INVENTION

The present invention provides an improved method for generating libraries of polysomes displaying nascent peptides suitable for affinity interaction screening. The improvement comprises using an E. coli S30 translation system for high efficiency translation of mRNA. The displayed peptide sequences can be of varying lengths, typically from 3–5000 amino acids long or longer, frequently from 5–100 amino acids long, and often from about 8–15 amino acids long. A library can comprise library members having varying lengths of displayed peptide sequence, or may comprise library members having a fixed length of displayed peptide sequence. Portions or all of the displayed peptide sequence (s) can be random, pseudorandom, defined set kernel, fixed, or the like. The present display methods include methods for in vitro display of single-chain antibodies, such as nascent scFv, which enable large-scale screening of scFv libraries having broad diversity of variable region sequences and binding specificities.

The present invention also provides a method for affinity screening a library of polysomes displaying nascent peptides (including single-chain antibodies) for library members which bind to a predetermined receptor (e.g., a mammalian proteinaceous receptor such as, for example, a peptidergic hormone receptor, a cell surface receptor, an intracellular protein which binds to other protein(s) to form intracellular protein complexes such as heterodimers and the like) or epitope (e.g., an immobilized protein, glycoprotein, oligosaccharide, and the like). An improvement of this method comprises contacting a preblocking agent with the receptor or epitope (or immobilized epitope surface or immobilized receptor surface) prior to and/or concomitant with contacting the polysome library with the epitope or receptor (or immobilized epitope surface or receptor surface). Suitable preblocking agents include casein, nonfat milk, bovine serum albumin, gelatin, tRNA, and the like. Optionally, a non-ionic detergent (erg. TweenD NP-40) is included to reduce nonspecific binding.

The present invention also provides a method for generating libraries of polysomes displaying nascent single-chain antibodies. In an embodiment, the method comprises using a coupled in vitro transcription/translation system to generate the polysomes from a library of DNA templates. Each DNA template library member comprises a gene cassette encoding a $V_H$ domain in polypeptide linkage to a $V_L$ domain, typically linked via a flexible spacer, such as for example (Gly-Gly-Gly-Gly-Ser)$_3$ (SEQ ID NO:1) or the like, and may comprise additional terminal peptide sequences, such as epitope tags, fusion partner polypeptides, and the like.

The present invention also provides an improved method for generating libraries of polysomes displaying nascent peptides. The improvement comprises using a coupled in vitro transcription/translation system to generate polysomes from a library of DNA templates; the resultant library of polysomes represents a range of displayed peptide sequences.

The present invention further provides a method of screening a library of polysomes displaying (1) nascent peptides or (2) single-chain antibodies for species having high binding affinity for a predetermined receptor or epitope (antigen). An improvement of this method comprises the additional step of placing sequences encoding positively selected nascent peptides or single-chain antibodies obtained by screening a polysome library into a bacteriophage display system for further affinity screening, such as under screening conditions incompatible with retention of intact polysome structure. Stated generally, an improvement of the method comprises a sequential affinity screen process utilizing a plurality of expression systems, wherein (1) a first expression system (e.g., a library of in vitro translated polysomes displaying nascent peptides) is screened for library members which bind to a predetermined receptor(s) or epitope(s), thereby selecting library members having substantial binding affinity for the predetermined receptor(s) or epitope(s); (2) the displayed peptide sequence(s) in the selected library members are identified and/or isolated thereby constituting first-round selected peptide sequences; (3) a second expression system (e.g., bacteriophage coat protein peptide display or a second in vitro expression system) comprising a population of library members which is substantially enriched for the first-round selected peptide sequences is screened for library members which bind to the predetermined receptor(s) or epitope(s), thereby selecting library members having substantial binding affinity for the predetermined receptor(s) or epitope(s); (4) the displayed peptide sequence(s) in the selected library members are identified and/or isolated thereby constituting subsequent-round selected peptide sequences.

The present invention provides novel methods for generating and screening single-chain antibody (e.g., scFv) libraries by in vitro synthetic methods. The single-chain antibody libraries can be screened to select and identify individual library members having the ability to bind or otherwise interact (e.g, such as catalytic antibodies) with a predetermined macromolecule, such as for example a proteinaceous receptor, peptide, oligosaccharide, virion, or other predetermined compound or structure. The individual library members typically comprise peptides or single-chain antibodies composed of naturally-occurring amino acids, but in some embodiments may comprise alternative amino acids, imino acids, or other building blocks compatible with in vitro translation systems employing unnatural aminoacyl tRNA species (see, PCT publication No. W090/05785). The displayed peptides, antibodies, peptidomimetic antibodies, and variable region sequences that are identified from such libraries can be used for therapeutic, diagnostic, research, and related purposes (e.g., catalysts, solutes for increasing osmolarity of an aqueous solution, and the like).

In a method of the invention, a single-chain antibody library is generated by in vitro synthesis in a cell-free system, wherein individual library members comprise a nascent polypeptide comprising a $V_H$ domain in polypeptide linkage to a $V_L$ domain, and wherein the nascent polypeptide is linked to a polynucleotide encoding said nascent polypeptide (or a polynucleotide complementary to the encoding polynucleotide sequence), such linkage typically being accomplished by a ribosome bound on a stalled polysome.

In a method of the invention, a peptide library is generated by in vitro synthesis in a cell-free system, wherein individual library members comprise a nascent polypeptide comprising a first polypeptide portion consisting of a random, pseudorandom, defined kernel, or predetermined sequence (or combination(s) thereof), and wherein the nascent polypeptide is linked to a polynucleotide encoding said nascent polypeptide (or a polynucleotide complementary to the encoding polynucleotide sequence), such linkage typically being accomplished by a ribosome bound on a stalled polysome.

Alternatively, the nascent polypeptide may comprise a first polypeptide portion consisting of a random, pseudorandom, defined kernel, or predetermined sequence (or combination(s) thereof) or scFv in polypeptide linkage to a second polypeptide portion ("tether") linked to a polynucleotide encoding said nascent polypeptide (or to a polynucleotide complementary to the encoding polynucleotide sequence). The nascent peptide or antibody is synthesized as a fusion protein comprising: (1) a polynucleotide-binding portion, termed the "tether segment", comprising a polypeptide sequence which binds to the encoding mRNA molecule serving as the translation template for the synthesis of the nascent antibody, or to a bound DNA primer or cDNA copy of such encoding mRNA, either directly or through binding an intermediate molecule (biotin, digoxigenin, or the like)

that is linked directly to the encoding mRNA or cDNA copy thereof, and (2) a second polypeptide portion, termed (1) the "displayed peptide", comprising a random, pseudorandom, defined kernel, or predetermined sequence (or combination (s) thereof), or (2) "single-chain antibody", comprising a $V_H$ and $V_L$ each having one of a variety of possible amino acid sequence combinations represented in the library. The tether segment serves to link the displayed peptide or single-chain antibody of an individual library member to the polynucleotide comprising the sequence information encoding the amino acid sequence of the individual library member's displayed peptide or $V_H$ and $V_L$ domains. The linked polynucleotide of a library member provides the basis for replication of the library member after a screening or selection procedure, and also provides the basis for the determination, by nucleotide sequencing, of the identity of the displayed peptide sequence or $V_H$ and $V_L$ amino acid sequence. The displayed peptide(s) or single-chain antibody (e.g., scFv) and/or its $V_H$ and $V_L$ domains or their CDRs can be cloned and expressed in a suitable expression system. Often polynucleotides encoding the isolated $V_H$ and $V_L$ domains will be ligated to polynucleotides encoding constant regions ($C_H$ and $C_L$) to form polynucleotides encoding complete antibodies (e.g., chimeric or fully-human), antibody fragments, and the like. Often polynucleotides encoding the isolated CDRs will be grafted into polynucleotides encoding a suitable variable region framework (and optionally constant regions) to form polynucleotides encoding complete antibodies (e.g., humanized or fully-human), antibody fragments, and the like.

In one embodiment, the tether segment comprises a RNA-binding polypeptide sequence that binds to the mRNA serving as the translation template for the nascent polypeptide. Typically, the tether segment comprising an RNA-binding polypeptide sequence has a conserved RNA-binding domain structure noted in RNA-binding proteins, such as an RKP motif, an arginine-rich motif (ARM), an RGG box, a KE (hnRNP K homology) motif, a dsRNA-binding motif, a zinc finger/knuckle, a cold-shock domain, or combination(s) thereof (see, Burd CG and Dreyfuss G (1994) Science 265: 615). For example and not limitation, an RNA-binding tether segment can comprise: (1) an RNP1 and/or RNP 2 consensus sequence (e.g., substantially identical to KGFG-FVXF (SEQ ID NO:2), RGYAFVXY(SEQ ID NO:3), LFVGNL(SEQ ID NO:4), or IYIKGM(SEQ ID NO:5)), (2) an arginine-rich domain (e.g., TRQARRNRRRRWRERQ (SEQ ID NO:6), ALGISYGRKKRRQRRRP(SEQ ID NO:7), MDAQTRRRERRAEKQAQW(SEQ ID NO:8), GTAKSRYKRRAELIAER(SEQ ID NO:9), or GNAKTRRHERRRKLAIER)(SEQ ID NO:10), (3) an RGG box (e.g., typically at least 2, 3, 4, or 5 RGG sequences), (4) a KH motif, or (5) combination(s) thereof can be present in the tether. Other RNA-binding sequence motifs known in the art can be employed, and novel RNA-binding peptide motifs (such as obtained by directed evolution, screening libraries for RNA-binding species, and the like) can also be used.

In an alternative embodiment, the tether segment comprises an epitope bound by an immunoglobulin which is covalently linked either to the mRNA serving as the translation template for the nascent polypeptide or to a cDNA copy thereof.

In another embodiment, the tether segment comprises a biotinylation substrate sequence which can be post-translationally biotinylated forming a biotinylated nascent peptide; the biotinylated nascent antibody binds through a streptavidin molecule linked either to the MRNA serving as the translation template for the nascent single-chain antibody or to a CDNA copy thereof; the streptavidin is linked to the mRNA or cDEA by direct covalent linkage or through noncovalent binding to biotin moieties incorporated into the mRNA or CDNA. Various additional embodiments are described.

In one embodiment, no tether segment is used; the nascent single-chain antibody is coupled to the polynucleotide (e.g, mRNA) by the translating ribosome which links the nascent single-chain antibody to the polysome complex. In such embodiments, translation stalling sequences are often incorporated into the mRNA to produce slowing/stalling of translation to enhance the stability of polysomes.

In a variation, the nascent polypeptide is coupled to the polynucleotide (e.g, mRNA) by a portion of the nascent polypeptide which inhibits ribosome elongation, such as by inhibiting peptidyl transferase. In an embodiment of this variation, the nascent polypeptide comprises an amino acid sequence which is predetermined to inhibit peptidyl transferase; examples of such polypeptide sequences include, but are not limited to, —MKTD—(SEQ ID NO:11) and —MSTSKNAD—(SEQ ID NO:12)—. Typically, such elongation inhibitory polypeptide segments are present in the amino-terminal half of the nascent polypeptide, often within about 50 amino acids or less of the amino-terminus, or can be amino-terminal. A nascent polypeptide can comprise one or a plurality of elongation inhibitory polypeptide segments, which may comprise identical sequences or different sequences. In an embodiment, the elongation inhibitory polypeptide segment(s) are located within 5 residues amino-terminal of a Gly-Ser spacer region; typically immediately amino-terminal to the Gly-Ser spacer region. The variation applies to any suitable nascent polypeptide, including but not limited to nascent peptides and nascent single chain antibodies.

In one variation, the invention also provides a method of generating nascent peptide or single-chain antibody libraries comprising the steps of: (1) translating in vitro an mRNA population wherein individual MRNA molecules individually encode a nascent polypeptide comprising a tether segment and a variable peptide segment or single-chain antibody (e.g., scFv) segment, under translation conditions wherein said tether segment binds to the encoding template MRNA or a polynucleotide primer annealed thereto prior to dissociation of the nascent peptide from the translation complex, thus producing a library of nascent peptide or single-chain antibody library members, (2) synthesizing a first-strand CDNA copy of the encoding mRNA species by reverse transcription primed from an extendable polynucleotide primer annealed to the template mRNA 3' to the portion of the mRNA encoding the nascent peptide or single-chain antibody sequence, optionally hydrolyzing the mRNA templates, thus producing a library of cDNA-containing nascent peptide or single-chain antibody library members, (3) screening the library of nascent peptide or single-chain antibody library members by contacting the library to an immobilized macromolecular species under binding conditions and separating library members bound to the macromolecular species from unbound library members and selecting either bound or unbound members as the selected library members, (4) synthesizing second-strand DNA complementary to the first-strand CDNA of the nascent library members, (5) ligating a suitable promoter and translation start site, if necessary (e.g., may be contained in the extendable polynucleotide primer), to the CDNA in the appropriate orientation to drive transcription of an MRNA complementary to the first-strand eDNA forming a transcription template (i.e., DNA template library member), (6) transcribing mRNA complementary to the first-strand cDNA from the transcription template, (7) repeating steps (1) through (6) until the desired level of affinity enrichment for selected bound (or unbound) nascent peptide or single-chain antibody library members is attained, and (8) isolating individual cDNA from the selected library members and determining the nucleotide sequence(s) of the variable peptide segment(s) and/or single-chain antibody segment(s) and/or determining the variable peptide segment, $V_H$, $V_L$, and/or CDR nucleotide sequence distribution(s) in the selected population by collectively sequencing the collection of cDNAs represented in the population of selected library members. In some variations, steps 4, 5, 6, and/or 7 may be omitted. Generally, the mRNA population of step (1) is generated by in vitro transcription of a DNA template library, wherein each DNA template library member encodes a polypeptide comprising a tether sequence and a variable peptide sequence or a single-chain antibody sequence. Each DNA template library member also comprises an operably linked promoter, especially a promoter suitable for in vitro transcription and sequences required for in vitro translation of the transcription product (mIRNA), such as a ribosome binding site.

The method may also comprise the variation wherein the transcription template(s) formed in step (5) (or portion thereof encoding the variable segment) or selected library members obtained by affinity screening is/are cloned into a phagemid expression vector (e.g., pAFF6) so that the encoded variable peptide sequence or single-chain antibody polypeptide sequence is expressed as a fusion with a bacteriophage coat protein and displayed on bacteriophage virions. The phage particles displaying the selected variable region sequence or single-chain antibody polypeptide sequences may be used for one or more subsequent rounds of affinity selection.

In an alternative variation, selected library members can be cloned or otherwise amplified, followed by additional rounds of in vitro translation and selection, avoiding the requirement that selected library members encode polypeptide sequences which are compatible with bacteriophage coat protein function and/or which are compatible with functional expression in a prokaryotic host cell. In one embodiment, selected library members are cloned in a prokaryotic vector (e.g., plasmid, phagemid, or bacteriophage) wherein a collection of individual colonies (or plaques) representing discrete library members are produced. Individual selected library members can then be manipulated (e.g., by site-directed mutagenesis, cassette mutagenesis; chemical mutagenesisa PCR mutagenesis, and the like) to generate a collection of library members representing a kernel of sequence diversity based on the sequence of the selected library member. The sequence of an individual selected library member can be manipulated to incorporate random mutation, pseudorandom mutation, defined kernel mutation (i.e., comprising variant and invariant residue positions and/or comprising variant residue positions which can comprise a residue selected from a defined subset of amino acid residues), and the like, either segmentally or over the entire length of the individual selected library member sequence. In addition, these mutational strategies can be applied to pools of individual selected mmebers, or to selected pools or subpopulations of selected library members, which might not have been individually isolated.

In a variation, the method also comprises amplifying selected library members, either individually or as a selected pool, with at least one cycle of error-prone PCR. A round of amplification can comprise one or more cycles of error-prone PCR, often in combination with one or more cycles of conventional PCR. The method can comprise serial dilution and subsequent rounds of error-prone PCR amplification of error-prone PCR products, and may include the further variation of pooling aliquots from each serial dilution round to form a final mutated pool comprising mutated variants representing varying degrees of mutation. In this variation, a selected library member or a selected subpopulation of library members is subjected to a first error-prone amplification round comprising at least one cycle of error-prone PCR; an aliquot of the amplification product is removed and subjected to at least one subsequent error-prone amplification round comprising at least one cycle of error-prone PCR prior to selection. Amplification products from at least one, preferably all, error-prone amplification round(s) are pooled, typically in approximately equimolar ratios, forming a pool of mutated variants representating a spectrum of mutational frequencies. Following error-prone PCR amplification, alone or in combination with conventional amplification methods, the mutated amplification products are subjected to at least one round of selection according to the method of the invention.

In a variation of the invention, the method can be used in conjunction with a selection target which comprises or consists of a small molecule (e.g., an organic compound less than about 2,500 Daltons), such as a pharmacophore, enzyme substrate, receptor ligand, and the like. Typically, the small molecule is immobilized on a support, typically a solid support such as beads, affinity chromatography matrix, or other suitable substrate such that it retains selective binding affinity for polypeptides which are predetermined to bind to it. The immobilized small molecule, or collection thereof, is used to selectively enrich for library members which bind to the immobilized small molecule, thereby facilitating removal, typically by washing, of unbound library members and consequently producing selective enrichment for library members which are retained by binding to the immobilized small molecule(s).

The method may also comprise the variation that the individual library members may be directly sequenced individually (i.e., not collectively) by diluting the pool of affinity-selected library members such that about 1 library member cDNA is represented in each separate reaction vessel (e.g., microtitre well). Each CDNA is then amplified by PCR and sequenced.

The invention also provides compositions comprising individual library members that comprise a nascent polypeptide comprising a first polypeptide portion linked to a polynucleotide encoding said nascent polypeptide (or a polynucleotide complementary to the encoding polynucleotide sequence) and a second polypeptide portion comprising (1) a variable amino acid segment or (2) a single-chain antibody, in peptide linkage to said first polypeptide portion. In one aspect of the invention, the individual library members lack bound ribosomese for example lacking ribosomes bound to a mRNA in a translation complex (e.g. polysome).

The invention also provides compositions comprising a nascent single-chain antibody polysome library which consists of a population of library members wherein essentially each library member comprises a single-chain antibody bound as a nascent polypeptide in a polysome. Typically, such libraries substantially lack library members encoding nascent polypeptides that do not comprise at least 15 contiguous amino acids of a naturally-occurring immunoglobulin sequence, preferably a human immunoglobulin (e.g., human $V_H$ or $V_L$) sequence. Such library members may comprise a tether segment, a translation stall segment, both, or neither of these.

The invention also provides peptide libraries comprising a plurality of individual library members of the invention, wherein (1) each individual library member of said plurality comprises a tether segment sequence which is substantially identical to the tether segment sequences of the remainder of individual library members in said plurality, and (2) each individual library member comprises a variable peptide segment sequence or single-chain antibody segment sequence which is distinct from the variable peptide segment sequences or single-chain antibody sequences of other individual library members in said plurality (although some library members may be present in more than one copy per library due to uneven amplification, stochastic probability, or the like).

The invention also provides novel compositions comprising at least one library member, said library member comprising a RNA molecule, or CDNA copy thereof, linked with the nascent variable peptide segment or nascent single-chain antibody encoded by said mRNA, wherein the linkage of the mRNA or CDNA to the nascent peptide is by noncovalent binding to the tether segment of said nascent variable peptide segment or said nascent single-chain antibody. Typically, such library members substantially lack bound ribosomes.

The invention also provides a product-by-process, wherein antibodies having a predetermined binding specificity are formed by the process of (1) screening a nascent single-chain antibody polysome library against a predetermined epitope (e.g., antigen macromolecule) and identifying and/or enriching library members which bind to the predetermined epitope, and (2) expressing in a cell a single-chain antibody encoded by a library member (or copy thereof) which binds the predetermined epitope and has been thereby isolated and/or enriched from the library.

BRIEF DESCRIPTION OF THE DRAWINGS

FIG. 1. (SEQ ID NO. 42843) This figure shows information relating to construction of a synthetic gene for expressing the D32.39 epitope or control, non-binding, peptides in vitro. Partial restriction map of the bacteriophage T7 promoter expression plasmid, pT7-7. The figure shows the nucleotide sequence and predicted amino acid sequence of the D32.39 epitope fusion protein after linearizing plasmid pLM138 with HindIII. Nucleotides are numbered on the right; amino acids are numbered on the left. The gene was constructed by annealing synthetic oligonucleotides to their complementary strands to generate double stranded cassettes flanked by the indicated restriction sites. Individual cassettes were cleaved by the appropriate restriction enzymes and subcloned sequentially to pT7-7 starting with the SalI/HindIII cassette, and followed by the BamHI/SalI and EcoRI/BamHI cassettes. The NdeI/EcoRI cassettes were subcloned last and contained either the D32.39 epitope sequence shown or the control sequence, 5' CATATGGCT-GTTTTCAAACGTACCGTTCAGGAATC 3' (NdeI and EcoRI sites are underlined).

FIG. 4. (SEQ ID NO:46–49) Subcloning of the DWA pool to the phagemid vector, pAFF6, for sequencing and ELISA. Approximately 25 ng of DNA was cleaved with NheI/KpnI before and after each round of affinity selection and ligated to the same sites of pAFF6 resulting in translational fusions of library peptides to the pIII capsid protein of M13 (C. Wagstrom, personal communication). Individual clones were isolated after transforming E. coli strain ARI 293 (HfrC prIA8914 zhc::Tn10(tet$^s$, kan$^r$) thi recA::cat) and grown in the presence of VCSH13 helper phage to isolate recombinant phage as previously described (Δ).

FIG. 5. The effect of DNA library concentration on protein synthesis in vitro. The incorporation of [$^{35}$S] methionine into protein was measured as described in the Materials and Methods.

FIG. 6. (SEQ. ID NO: 50–74) Amino acid alignment of selected peptide sequences with dynorphin B. The six-residue D32.39 epitope sequence of dynorphin B and the peptide regions similar to it are shown in the box. A total of 6, 13, 19, and 9 independent clones were sequenced from rounds 2, 3, 4 and 5, respectively. The frequency indicates the number of times each sequence occurred among the clones isolated from each round, and the asterisks indicate identical sequences found in different rounds. Binding affinities for D32.39 were determined by chemically synthesizing the indicated peptide sequences and measuring the IC$_{50}$ as described in the Experimental Examples.

FIG. 7. Schematic maps of plasmids pLM169, pLM 166, and pLM 153.

DEFINITIONS

Figure 2A:
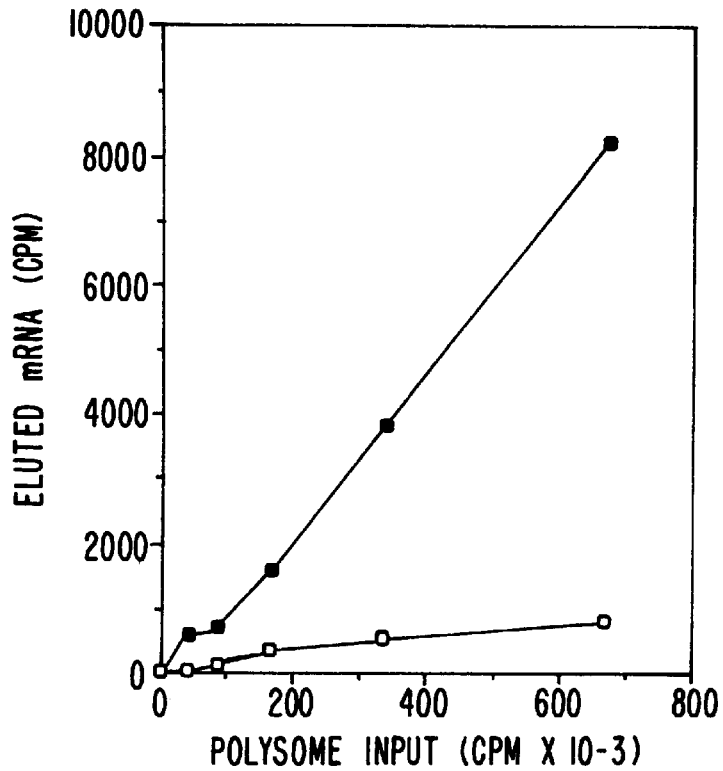
FIG. 2. Specific binding of polysomes to mAb D32.39. Radiolabelled polysomes were isolated from reactions programmed with 1.5 μg of HindIII-linearized plasmid pLM138 or pLM142 and bound to microtiter wells containing the immobilized mAb. The recovered mIRNA was quantitated by TCA precipitation. (Panel A) Binding of polysomes containing the D32.39 epitope (closed boxes) or control (open boxes) sequences. (Panel B) Competition binding assay. Microtiter wells were preincubated with polysome buffer in the absence or presence of 10 μH dynorphin B peptide for 1 hr at 4° C. prior to adding 131,000 cpm of polysomes containing the D32.39 epitope (RQFKVVT) (SEQ ID NO:18) or control (VFKRTVQ) (SEQ ID NO:15) sequences.

Unless defined otherwise, all technical and scientific terms used herein have the same meaning as commonly understood by one of ordinary skill in the art to which this invention belongs. Any methods and materials similar or equivalent to those described herein can be used in the practice or testing of the present invention, but the currently preferred methods and materials are described herein. For purposes of the present invention, the following terms are defined below.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

As used herein, the twenty conventional amino acids and their abbreviations follow conventional usage (*Biochemistry*, Third Edition (1988), Lubert Stryer, ed., W. H. Freeman and Company, N.Y., which is incorporated herein by reference). Stereoisomers (erg., D-amino acids) of the twenty conventional amino acids, unnatural amino acids such as α,α-disubstituted amino acids, N-alkyl amino acids, lactic acid, and other unconventional amino acids and analogs may also be suitable components for polypeptides of the present invention. Examples of unconventional amino acids include, 4-hydroxyproline, γ-carboxyglutamate, ε-NK N,N-trimethyllysine, ε-N-acetyllysine, O-phosphoserine, N-acetylserine, N-formylmethionine, 3-methylhistidine, 5-hydroxylysine, ω-N-methylarginine, and other similar amino acids and imino acids (e.g., 4-hydroxyproline). Unconventional and unnatural amino acids may be incorporated in vitro translation products if incorporated into an aminoacyl-tRNA that can participate in ribosome-mediated peptide elongation.

As used herein, the term "nascent peptide" refers to a polypeptide produced by ribosome-mediated translation of a template mRNA, and wherein the polypeptide is associated with the encoding template mRNA or a CDNA copy of the template MRNA. Nascent peptides may correspond to full-length translation products encoded by the entire open reading frame of the template mRNA but can also include partially translated or prematurely terminated products. A "nascent single-chain antibody" is a nascent polypeptide which comprises a single-chain antibody.

As used herein, the term "single-chain antibody" refers to a polypeptide comprising a V$_H$ domain and a V$_L$ domain in polypeptide linkage, generally linked via a spacer peptide (e.g., [Gly-Gly-Gly-Gly-Ser]$_x$), (SEQ ID. NO: 75) and which may comprise additional amino acid sequences at the amino- and/or carboxy-termini. For example, a single-chain antibody may comprise a tether segment for linking to the encoding polynucleotide. As an example, a scFv is a single-chain antibody. Single-chain antibodies are generally proteins consisting of one or more polypeptide segments of at least 10 contiguous amino acids substantially encoded by genes of the immunoglobulin superfamily (e.g., see *The Immunoglobulin Gene Superfamily*, A. F. Williams and A. N. Barclay, in *Immunoglobulin Genes,* T. Honjo, F. W. Alt, and T. H. Rabbitts, eds., (1989) Academic Press. San Diego, Calif., pp.361–387, which is incorporated herein by reference), most frequently encoded by a rodent, non-human primate, avian, porcine, bovine, ovine, goat, or human heavy chain or light chain gene sequence. A functional single-chain antibody generally contains a sufficient portion of an immunoglobulin superfamily gene product so as to retain the property of binding to a specific target molecule, typically a receptor or antigen (epitope).

As used herein, the term "complementarity-determining region" and "CDR" refer to the art-recognized term as exemplified by the Kabat and Chothia CDR definitions also generally known as hypervariable regions or hypervariable loops (Chothia and Lesk (1987) *J. Mol. Biol.* 196: 901; Chothia et al. (1989) *Nature* 342: 877; E. A. Kabat et al., Sequences of Proteins of Immunological Interest (National Institutes of Health, Bethesda, Md.) (1987); and Tramontano et al. (1990) *J. Mol. Biol.* 215: 175). Variable region domains typically comprise the amino-terminal approximately 105–115 amino acids of a naturally-occurring immunoglobulin chain (e.g., amino acids 1–110), although variable domains somewhat shorter or longer are also suitable for forming single-chain antibodies.

An immunoglobulin light or heavy chain variable region consists of a "framework" region interrupted by three hypervariable regions, also called CDR'S. The extent of the framework region and CDR's have been precisely defined (see, "Sequences of Proteins of Immunological Interest," E. Kabat et al, 4th Ed., U.S. Department of Health and Human Services, Bethesda, Md. (1987)). The sequences of the framework regions of different light or heavy chains are relatively conserved within a species. As used herein, a "human framework region" is a framework region that is substantially identical (about 85% or more, usually 90–95% or more) to the framework region of a naturally occurring human immunoglobulin. The framework region of an antibody, that is the combined framework regions of the constituent light and heavy chains, serves to position and align the CDR's. The CDR's are primarily responsible for binding to an epitope of an antigen.

As used herein, the term "tether segment" refers to a portion of a nascent peptide or nascent antibody which binds to the encoding mRNA molecule serving as the translation template for the synthesis of the nascent polypeptide, or to a cDNA copy of such encoding mRNA, either directly or through binding an intermediate molecule that is linked directly to the encoding mRNA or CDNA copy thereof.

As used herein, the term "variable segment" refers to a portion of a nascent peptide which comprises a random, pseudorandom, or defined kernel sequence. A variable segment can comprise both variant and invariant residue positions, and the degree of residue variation at a variant residue position may be limited; both options are selected at the discretion of the practitioner. Typically, variable segments are about 5 to 20 amino acid residues in length (e.g., 8 to 10), although variable segments may be longer and may comprise antibody portions or receptor proteins, such as an antibody fragment, a nucleic acid binding protein, a receptor protein, and the like.

As used herein, "random peptide sequence" refers to an amino acid sequence composed of two or more amino acid monomers and constructed by a stochastic or random process. A random peptide can include framework or scaffolding motifs, which may comprise invariant sequences.

As used herein "random peptide library" refers to a set of polynucleotide sequences that encodes a set of random peptides, and to the set of random peptides encoded by those polynucleotide sequences, as well as the fusion proteins containing those random peptides.

As used herein, the term "pseudorandom" refers to a set of sequences that have limited variability, so that for example the degree of residue variability at one position is different than the degree of residue variability at another position, but any pseudorandom position is allowed some degree of residue variation, however circumscribed.

As used herein, the term "defined sequence framework" refers to a set of defined sequences that are selected on a nonrandom basis, generally on the basis of experimental data or structural data; for example, a defined sequence framework may comprise a set of amino acid sequences that are predicted to form a β-sheet structure or may comprise a leucine zipper heptad repeat motif, a zinc-finger domain, among other variations. A "defined sequence kernel" is a set of sequences which encompass a limited scope of variability. Whereas (1) a completely random 10-mer sequence of the 20 conventional amino acids can be any of $(20)^{10}$ sequences, and (2) a pseudorandom 10-mer sequence of the 20 conventional amino acids can be any of $(20)^{10}$ sequences but will exhibit a bias for certain residues at certain positions and/or overall, (3) a defined sequence kernel is a subset of sequences which is less that the maximum number of potential sequences if each residue position was allowed to be any of the allowable 20 conventional amino acids (and/or allowable unconventional amino/imino acids). A defined sequence kernel generally comprises variant and invariant residue positions and/or comprises variant residue positions which can comprise a residue selected from a defined subset of amino acid residues), and the like, either segmentally or over the entire length of the individual selected library member sequence. Defined sequence kernels can refer to either amino acid sequences or polynucleotide sequences. For illustration and not limitation, the sequences $(NNK)_{10}$ and $(NNM)_{10}$ where N represents A, T, G, or C; K represents G or T; and M represents A or C, are defined sequence kernels.

As used herein "RNA binding protein" refers to a protein that specifically interacts with a polyribonucleotide strand or strands. Those of skill in the art will recognize that, for purposes of the present invention, the RNA binding protein must bind specifically to the template mRNA, for example the RNA binding protein may bind to a specific sequence of the mRNA which will suppress reinitiation of new translation from the template mRNA. In embodiments of the invention in which DNA binding polypeptides are used, DNA binding proteins are typically those proteins which bind to DNA, in a sequence-specific or sequence-insensitive manner (e.g., helix-loop-helix, zinc finger, homeodomain, histone, etc.).

In some embodiments, DNA-binding proteins can bind to DNA in a sequence-specific manner (e.g., bind to specific predetermined nucleotide sequences); in such embodiments, the nascent polypeptide library members comprise an encoding polynucleotide (or DNA primer bound thereto) which comprises a sequence bound by the sequence specific DNA-binding protein. As used herein, the term "polynucleotide-binding protein" encompasses RNA-binding proteins and DNA-binding proteins, whether sequence-specific or sequence-insensitive.

As used herein "epitope" refers to that portion of an antigen or other macromolecule capable of forming a binding interaction that interacts with the variable region binding pocket of an antibody. Typically, such binding interaction is manifested as an intermolecular contact with one or more amino acid residues of a CDR.

As used herein, "receptor" refers to a molecule that has an affinity for a given ligand. Receptors can be naturally occurring or synthetic molecules. Receptors can be employed in an unaltered state or as aggregates with other species.

Receptors can be attached, covalently or noncovalently, to a binding member, either directly or via a specific binding substance. Examples of receptors include, but are not limited to, antibodies, including monoclonal antibodies and antisera reactive with specific antigenic determinants (such as on viruses, cells, or other materials), cell membrane receptors, complex carbohydrates and glycoproteins, enzymes, and hormone receptors.

As used herein "ligand" refers to a molecule, such as a random peptide or variable segment sequence, that is recognized by a particular receptor. As one of skill in the art will recognize, a molecule (or macromolecular complex) can be both a receptor and a ligand. In general, the binding partner having a smaller molecular weight is referred to as the ligand and the binding partner having a greater molecular weight is referred to as a receptor.

As used herein, "linker" or "spacer" refers to a molecule or group of molecules that connects two molecules, such as a DNA binding protein and a random peptides and serves to place the two molecules in a preferred configuration, e.g., so that the random peptide can bind to a receptor with minimal steric hindrance from the DNA binding protein.

As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame.

As used herein, "glycosylating cell" is a cell capable of glycosylating proteins, particularly eukaryotic cells capable of adding an N-linked "core oligosaccharide" containing at least one mannose residue and/or capable of adding an O-linked sugar, to at least one glycosylation site sequence in at least one polypeptide expressed in said cell, particularly a secreted protein. Thus, a glycosylating cell contains at least one enzymatic activity that catalyzes the attachment of a sugar residue to a glycosylating site sequence in a protein or polypeptide, and the cell actually glycosylates at least one expressed polypeptide. For example but not for limitation, mammalian cells are typically glycosylating cells. Other eukaryotic cells, such as insect cells and yeast, may be glycosylating calls.

As used herein, "error-prone PCR" refers to a polynucleotide amplification process whereby amplification products comprise a frequency of mutation, typically in the form of nucleotide misincorporation (e.g., substitution), which is at least one standard deviation greater than would be produced in a parallel amplification reaction according to a standard conventional PCR protocol, such as U.S. Pat. Nos. 4,683, 202 and 4,965,188; for example but not limitation, a error-prone PCR reaction can be conducted by the method of Cadwell and Joyce (1992) *PCR Methods Appl.* 2: 28 or Bartel and Szostak (1993) *Science* 261: 1411 or other suitable error-prone amplification method as is known in the art and understood by the practitioner to serve as an amplification method yielding an enhanced frequency of mutation in amplification products.

DETAILED DESCRIPTION

Generally, the nomenclature used hereafter and many of the laboratory procedures in cell culture, molecular genetics, and nucleic acid chemistry and hybridization described below are those well known and commonly employed in the art. Standard techniques are used for recombinant nucleic acid methods, polynucleotide synthesis, in vitro polypeptide synthesis, and the like and microbial culture and transformation (e.g. electroporation). Generally enzymatic reactions and purification steps are performed according to the manufacturer's specifications. The techniques and procedures are generally performed according to conventional methods in the art and various general references (see, generally, Sambrook et al. Molecular Cloning: A Laboratory Manual, 2d ed. (1989) Cold Spring Harbor Laboratory Press, Cold Spring Harbor, N.Y.; and *Antibodies: A Laboratory Manual,* (1988) E. Harlow and D. Lane, Cold Spring Harbor Laboratory, Cold Spring Harbor, N.Y., each of which is incorporated herein by reference) which are provided throughout this document. The procedures therein are believed to be well known in the art and are provided for the convenience of the reader. All the information contained therein is incorporated herein by reference.

Oligonucleotides can be synthesized on an Applied Bio Systems oligonucleotide synthesizer according to specifications provided by the manufacturer Methods for PCR amplification are described in the art (*PCR Technology: Principles and Applications for DNA Amplification* ed. HA Erlich, Stockton Press, New York, N.Y. (1989); *PCR Protocols: A Guide to Methods and Applications,* eds. Innis, Gelfland, Snisky, and White, Academic Press, San Diego, Calif. (1990); Mattila et al. (1991) *Nucleic Acids Res.* 19: 4967; Eckert, K. A. and Kunkel, T. A. (1991) *PCR Methods and Applications* 1: 17; and U.S. Pat. Nos. 4,683,202 and 4,965,188, each of which are incorporated herein by reference) and exemplified hereinbelow.

Overview

The present invention provides novel compositions and methods for screening in vitro polysome libraries displaying nascent peptides comprising a random, pseudorandom, or defined sequence polypeptide framework. In an aspect of the invention, polysome libraries display single-chain antibodies comprising a $V_H$ domain, $V_L$ domain, and spacer peptide. In an aspect, polysome libraries display non-immunoglobulin peptide sequences which can be selectively enriched for library members having a binding affinity for a predetermined target molecule.

Generally, a single-chain expression polynucleotide is generated. This expression polynucleotide contains: (1) a single-chain antibody cassette consisting of a $V_H$ domain, spacer peptide, and $V_L$ domain operably linked to encode a single-chain antibody, (2) a promoter suitable for in vitro transcription (e.g., T7 promoter, SP6 promoter, and the like) operably linked to ensure in vitro transcription of the single-chain antibody cassette forming a mRNA encoding a single-chain antibody, and (3) a transcription termination sequence suitable for functioning in an in vitro transcription reaction. Optionally, the expression polynucleotide may also comprise an origin of replication and/or a selectable marker. An example of a suitable expression polynucleotide is pLM166 (see, EXAMPLE 2).

The $V_H$ and $V_L$ sequences can be conveniently obtained from a library of $V_H$ and $V_L$ sequences produced by PCR amplification using V gene family-specific primers or V gene-specific primers (Nicholls et al. (1993) *J. Immunol. Meth.* 165: 81; W093/12227) or are designed according to standard art-known methods based on available sequence information. Typically, mouse or human $V_H$ and $V_L$ sequences are isolated. The $V_H$ and $V_L$ sequences are then ligated, usually with an intervening spacer sequence (e.g., encoding an in-frame flexible peptide spacer), forming a cassette encoding a single-chain antibody. Often, a library comprising a plurality of $V_H$ and $V_L$ sequences are used (sometimes also with a plurality of spacer peptide species represented). Frequently, a library is constructed wherein one or more of the $V_H$ and $V_L$ sequences are mutated to increase sequence diversity particularly at CDR residues, sometimes at framework residues. V region sequences can be conveniently cloned as cDNAs or PCR amplification products for immunoglobulin-expressing cells. For example, cells from human hybridoma, or lymphoma, or other cell line that synthesizes either cell surface or secreted immunoglobulin are used for the isolation of polyA+ RNA. The RNA is then used for the synthesis of oligo dT primed cDNA using the enzyme reverse transcriptase (for general methods see, Goodspeed et al. (1989) *Gene* 76: 1; Dunn et al. (1989) *J. Biol. Chem.* 264: 13057). Once the V-region CDNA or PCR product is isolated, it is cloned into a vector to form a single-chain antibody cassette. For example and not limitation, the CANTAB vector system (sold commercially by Pharmacia Biotech, Alameda, Calif.) and its variants are suitable for cloning $V_H$ and $V_L$ sequences by PCR amplification. The phagemid pSEx (Dubel et al. (1993) *Gene* 128: 97) and similar vectors are suitable for surface display of scFv on bacteriophage.

In one aspect, the present invention provides an improved method, using an in vitro translation system for translating mRNA to form polysomes displaying nascent peptides, including nascent single-chain antibodies, which in one variation are scFv. This aspect of the invention comprises using an *E. coli* S30 translation system (Promega, Madison, Wisconsin) for efficient in vitro translation. The *E. coli* S30 translation system provides advantageous high efficiency translation of a variety of mRNA templates, as compared to other in vitro translation systems (e.g., wheat germ extract, rabbit reticulocyte lysate). Furthermore, the *E. coli* S30 system can provide a coupled transcription/translation system which is generally more convenient to use and efficient than an uncoupled system. In addition, the S30 system for in vitro translation is well characterized and quite amenable to the preparation of very large reaction mixtures, thus facilitating the construction of very large libraries by the methods of the invention. Thus, while the invention is typically practiced with reaction volumes of 50 microlitres to 5 mL, one can also prepare libraries in reaction volumes of 5 mL to 50 mL (or even larger) by the present methods. The S30 system is also amenable to the incorporation of unnatural amino acids using tRNA molecules charged with unnatural amino acids. See PCT patent publication No. 90/05785, incorporated herein by reference.

In another aspect, the present invention provides improved binding and/or washing conditions for screening polysome peptide-display libraries and single-chain antibody display libraries. In general, this improvement comprises: (1) isolating polysomes from an in vitro translation reaction by ultracentrifugation prior to screening the recovered polysomes for high-affinity binding to a receptor or epitope, and optionally the pellet containing the centrifugation-purified polysomes is resolubilized in a suitable buffer (i.e., does not disrupt intact polysomes) and centrifuged a second time to further purify the polysome population prior to affinity screening with receptor or epitope, and/or (2) reducing non-specific binding of nascent peptide-displaying polysomes or nascent single-chain antibody-displaying polysomes by contacting a preblocking agent (e.g., nonfat milk, casein, bovine serum albumin, gelatin, tRNA) to the immobilized receptor or epitope prior to affinity screening. A non-ionic detergent may optionally also be added.

In another aspect, the invention provides a method for generating nascent peptide-polysome libraries or nascent single-chain antibody-polysome libraries by coupled in vitro transcription/translation using an E. coli S30 system. This improvement avoids the bacteriophage-display method which requires replication and/or transcription of the DNA templates in a cell, which may reduce the diversity of the library and/or skew the distribution of the relative abundances of individual library members. Moreover, the coupled E. coli system is highly efficient and the library size is not limited by the transformation frequency of host cells or structural constraints of bacteriophage coat proteins.

In another aspect, the invention provides an improvement to the general method of screening nascent peptide-polysome libraries. This improvement can be used in conjunction with single-chain antibody polysome libraries. The improvement comprises the step of taking DNA sequences produced from positive nascent peptide-polysomes (or single-chain antibody polysomes) obtained after one or more rounds of affinity screening and performing one or more additional rounds of affinity screening by a different screening method, such as by expression of the selected DNA sequencers) in a bacteriophage coat protein display system, by expression as a soluble antibody in a prokaryotic or eukaryotic expression system, or by various methods for in vitro expression. For example, expression of scFv in eukaryotic expression systems, particularly in glycosylating cells, has the benefit of avoiding potential aggregation and misfolding of the scFv which may occur in some prokaryotic-based expression systems, as well as producing a glycosylated scFv, if said scFv contains suitable glycosylating site sequence(s).

For example, bacteriophage antibody display libraries can be created from selected sequences by subcloning the positive (ice., selected) DNA sequencers) into a phagemid vector (e.g., pAFF6) wherein the subcloned DNA is expressed as a fusion with a bacteriophage coat protein (e.g., pIII or pVIII) in the same reading frame as the nascent peptides (or single-chain antibodies) of the positive polysomes. The phagemid is propagated to produce bacteriophage particles displaying the nascent peptide sequence (or single-chain antibody) as a fusion with a phage coat protein. This improvement also relates to subcloning the nucleic acids encoding positive peptide-polysomes into other selection systems, such as the peptides on plasmids (using, e.g., lac as the DNA binding protein) or the maltose binding protein systems discussed above.

The peptide-displaying phage (or other, depending on the selection system chosen) particles are used for affinity screening by any suitable method, including panning, chromatography, and the like using an immobilized receptor or epitope (PCT Publication Nos. 91/17271, 91/18980, and 93/08278). Thus, in some embodiments, the phage (or phagemid) particle is used in an ELISA to determine the specificity of peptide binding. The availability of such assays and selection methods for the phage (or other) selection systems allows other advantages to be realized from the improved polysome display method of the present invention. In one embodiment, the variable region of nucleic acid that is expressed by the polysome and tested for receptor binding is a concatemer of short (i.e., 6 to 20 amino acids in length) peptide coding sequences optionally linked through nucleotides that are a restriction enzyme recognition site. After selection, the concatemer is cleaved with the restriction enzyme and the fragments (encoding the individual peptides) are cloned into the secondary selection system (i.e., the peptides on phage system), where a single panning cycle (binding of peptide to receptor and washing away unbound peptides) will serve to enrich the library with the peptide sequences from the concatemer that encode the ligands of interest. One could also use the process of concatemerization to combine and sequence together a number of individual peptide encoding sequences from a pool of positive peptide-polysomes.

In one embodiment, the single-chain antibody-encoding portion of the polynucleotide that is expressed by the polysome and tested for epitope binding encodes a $V_H$ and $V_L$ which are flanked by convenient restriction sites to facilitate the excision of the $V_H$ sequence, $V_L$ sequence, or both. After selection, the site(s) is/are cleaved with the restriction enzyme(s) and the fragments (encoding the individual domains or entire scFv) are cloned into a secondary selection system (e.g., antibody bacteriophage display system), where a single panning cycle (binding of single-chain antibody to epitope and washing away unbound single-chain antibodies) will serve to enrich the library for members that encode the single-chain antibodies of interest.

With regard to methods of generating peptide-polysomes and single-chain antibody-polysomes, it is desirable in some embodiments to employ a coupled in vitro transcription/translation system (e.g., E. coli S30) to produce a very large library of nascent peptide-polysomes (single-chain antibody-polysomes) which is initially screened for ligand-binding species, epitope-binding species, or receptor-binding species. In a coupled system, DNA encoding the library is added to the extract for performing transcription and translation. Of course, one can also use an uncoupled system, producing the RNA in one reaction and then adding that RNA to an in vitro translation system. After production, screening and selection, the positive isolates (e.g., enriched pools of positive isolates) are then transferred into a bacteriophage display system that may be screened further for receptor or epitope binding species using a variety of assays (such as the ELISA noted above) and screening conditions, including assays and selection steps that might not be compatible with intact polysomes. Moreover, once positive sequences have been inserted into a bacteriophage peptide-display vector (e.g., pAFF6), they may be conveniently mutagenized (e.g., with mutagenic PCR and/or site-directed oligonucleotide mutagenesis (e.g., in M13) and/or chemical mutagenesis for producing advantageous sequence variants. Thus, single-chain antibodies which are isolated after an initial round (or multiple rounds, which may include display on phage, expression as a soluble scFV in a prokaryotic or eukaryotic cell, or in vitro expression, in any order) of screening can be cloned into a bacteriophage antibody-display vector and can be mutagenized further, typically by limited sequence diversification in or near one or more of the CDRs, to effectively mirror the in vivo process known as "affinity sharpening". The diversified antibody library can then be screened according to conventional bacteriophage antibody-display methods. Alternatively, single-chain antibodies which are isolated after an initial round (or multiple rounds) of screening can be retained in a polysome-display vector and can be mutagenized further; the diversified single-chain antibody-polysome library can be screened according to the methods described herein and variations thereof.

The present invention also provides random, pseudorandom, and defined sequence framework peptide libraries and methods for generating and screening those libraries to identify useful compounds (e.g., peptides, including single-chain antibodies) that bind to receptor molecules or epitopes of interest or gene products that modify peptides or RNA in a desired fashion. The random, pseudorandom, and defined sequence framework peptides are produced from libraries of nascent peptide library members that comprise nascent peptides or nascent single-chain antibodies attached to an mRNA template from which the nascent peptide was synthesized by in vitro translation, or attached to a DNA primer hybridized to the mRNA or to a cDNA copy of the mRNA template. The mode of attachment may vary according to the specific embodiment of the invention selected.

A method of affinity enrichment allows a very large library of peptides and single-chain antibodies to be screened and the polynucleotide sequence encoding the desired peptide(s) or single-chain antibodies to be selected. The polynucleotide can then be isolated and sequenced to deduce the amino acid sequence of the selected peptide(s) or single-chain antibodies (or just $V_H$, $V_L$, or CDR portions thereof). Using these methods, one can identify a peptide or single-chain antibody as having a desired binding affinity for a molecule. The peptide or antibody can then be synthesized in bulk by conventional means.

A significant advantage of the present invention is that no prior information regarding an expected ligand structure is required to isolate peptide ligands or antibodies of interest. The peptide identified can have biological activity, which is meant to include at least specific binding affinity for a selected receptor molecule and, in some instances, will further include the ability to block the binding of other compounds, to stimulate or inhibit metabolic pathways, to act as a signal or messenger, to stimulate or inhibit cellular activity, and the like.

Improved Methods for Screening Nascent Peptide Libraries

A polysome library displaying nascent peptides can be generated by a variety of methods. Generally, an in vitro translation system is employed to generate polysomes from a population of added mRNA species. Often, the in vitro translation system used is a conventional eukaryotic translation system (e.g., rabbit reticulocyte lysate, wheat germ extract). However, an *E. coli* S30 system (Promega, Madison, Wis.) can be used to generate the polysome library from a population of added mRNA species or by coupled transcription/translation (infra). Suitable *E. coli* S30 systems may be produced by conventional methods or may be obtained from commercial sources (Promega, Madison, Wis.).

The *E. coli* S30 translation system is generally more efficient at producing polysomes suitable for affinity screening of displayed nascent peptides, and the like. Moreover, a prokaryotic translation system, such as the *E. coli* S30 system, has the further advantage that a variety of drugs which block prokaryotic translation (e.g., inhibitors of ribosome function), such as rifampicin or chloramphenicol, can be added at a suitable concentration and/or timepoint to stall translation and produce a population of stalled polysomes, suitable for affinity screening against a predetermined receptor or epitope (e.g., a G protein-linked receptor protein).

In general, the improved method comprises the steps of (1) introducing a population of mRNA species into a prokaryotic in vitro translation system (e.g., *E. coli* S30) under conditions suitable for translation to form a pool of polysomes displaying nascent peptides or nascent single-chain antibodies (e.g., stalled polysomes), so-called polysome-forming conditions; (2) contacting the polysomes with a predetermined receptor or epitope under suitable binding conditions (i.e., for specific binding to the receptor/epitope and for preserving intact polysome structure); (3) selecting polysomes which are specifically bound to the receptor or epitope (e.g., by removing unbound polysomes by washing with a solution); and (4) determining the polynucleotide sequence(s) of the selected polysomes (e.g., by synthesizing cDNA or reverse transcriptase PCR amplification product, and sequencing said cDNA or amplification product). Often, the receptor or epitope used for screening is immobilized, such as by being bound to a solid support.

In a variation of the improved method, the population of mRNA molecules is introduced into the in vitro translation system by de novo synthesis of the mRNA from a DNA template. In this improvement, a population of DNA templates capable of being transcribed in vitro (e.g., having an operably linked T7 or SP6 or other suitable promoter) are introduced into a coupled in vitro transcription/translation system (e.g., an *E. coli* S30 system) under conditions suitable for in vitro transcription and translation of the transcribed product. Generally, using a coupled in vitro transcription/translation system is highly efficient for producing polysomes displaying nascent peptides and single-chain antibodies suitable for affinity screening, of course, and as noted above, uncoupled systems may also be used, i.e., by adding mRNA to an in vitro translation extract.

A further improvement to the general methods of screening nascent peptide-displaying polysomes and single-chain antibody-displaying polysomes comprises the additional step of adding a preblocking agent (e.g., nonfat milk, serum albumin, tRNA, and/or gelatin) prior to or concomitant with the step of contacting the nascent peptide-displaying polysomes with an immobilized receptor or the nascent single-chain antibody-displaying polysomes with an immobilized epitope. The additional step of adding a preblocking agent reduces the amount of polysomes which bind nonspecifically to the receptor or epitope and/or to the immobilization surface (e.g., microtitre well), thereby enhancing the specificity of selection for polysomes displaying peptides that specifically bind to the receptors(s) or antibodies which specifically bind the predetermined epitope(s). Although the preblocking agent can be selected from a broad group of suitable compositions, the group of preblocking agents comprising: nonfat milk/nonfat milk solids, casein, bovine serum albumin, transfer RNA, and gelatin are preferred, with nonfat milk being especially preferable. Other suitable preblocking agents can be used. Preblocking agents that do not substantially interfere with specific binding (i.e., non-interfering) are suitable.

A further improvement to the general methods of screening nascent peptide-displaying polysomes comprises the additional step of isolating polysomes from an in vitro translation reaction (or a coupled in vitro transcription/translation reaction) prior to the step of contacting the nascent peptide-displaying polysomes with immobilized receptor. Generally, the polysomes are isolated from a translation reaction by high speed centrifugation to pellet the polysomes, so that the polysome pellet is recovered and the supernatant containing contaminants is discarded. The polysome pellet is resolubilized in a suitable solution to retain intact polysomes. The resolubilized polysomes may be recentrifuged at lower speed (i.e., which does not pellet polysomes) so that the insoluble contaminants pellet and are discarded and the supernatant containing soluble polysomes is recovered, and the supernatant used for affinity screening. Alternatively, the resolubilized polysomes may be used for affinity screening directly (i.e., without low speed centrifugation). Furthermore, the order of centrifugation may be reversed, so that low speed centrifugation is performed prior to high speed centrifugation; the low speed centrifugation supernatant is then centrifuged at high speed and the pelleted polysomes are resolubilized and used for affinity screening. Multiple rounds of high speed and/or low speed centrifugation may be used to increasingly purify the polysomes prior to contacting the polysomes with the immobilized selection receptor(s) or epitope(s).

Another improvement to the general methods of affinity screening of nascent peptide-displaying polysomes comprises adding a non-ionic detergent to the binding and/or wash buffers. Non-ionic detergent (e.g., Triton X-100l NP-40, Tween, etc.) is added in the binding buffer (i.e., the aqueous solution present during the step of contacting the polysomes with the immobilized receptor) and/or the wash buffer (i.e., the aqueous solution used to wash the bound polysomes (i.e., bound to the immobilized receptor). Generally, the non-ionic detergent is added to a final concentration of about between 0.01 to 0.5% (v/v), with 0.1% being typical.

Another improvement to the general methods of affinity screening of nascent peptide libraries is generating the DNA template library (from which the mRNA population is transcribed) in vitro without cloning the library in host cells. Cloning libraries in host cells frequently diminishes the diversity of the library and may skew the distribution of the relative abundance of library members. In vitro library construction generally comprises ligating each member of a population of polynucleotides encoding library members to a polynucleotide sequence comprising a promoter suitable for in vitro transcription (e.g., T7 promoter and leader). The resultant population of DNA templates may optionally be purified by gel electrophoresis. The population of DNA templates is then transcribed and translated in vitro, such as by a coupled transcription/translation system (e.g., $E.$ $coli$ S30).

A further improvement to the general methods of affinity screening comprises the added step of combining affinity screening of a nascent peptide-displaying polysome library with screening of a bacteriophage peptide display library (or other, i.e., peptides on plasmids, expression as secreted soluble antibody in host cells, in vitro expression). In this improvement, polysomes are isolated by affinity screening of a nascent peptide-display library. The isolated polysomes are dissociated, and cDNA is made from the mRMA sequences that encoded nascent peptides that specifically bound to the receptor(s). The cDNA sequences encoding the nascent peptide binding regions (i.e., the portions which formed binding contacts to the receptor(s); variable segment sequences) are cloned into a suitable bacteriophage peptide display vector (e.g., pAFF6 or other suitable vector). The resultant bacteriophage vectors are introduced into a host cell to produce a library of bacteriophage particles. Each of the phage clones express on their virion surface the polysome-derived peptide sequences as fusions to a coat protein (e.g., as an N-terminal fusion to the pIII coat protein). By incorporating the in vitro-enriched peptide sequences from the polysome screening into a bacteriophage display system, it is possible to continue affinity selection for additional rounds. It is also advantageous, because the resultant bacteriophage display libraries can be screened and tested under conditions that might not have been appropriate for the intact polysomes. For example, although the monovalent display that can be achieved with the polysome system has advantages in isolating high affinity ligands (depending on conditions, a multivalent ligand composed of several copies of a low affinity ligand can have a very high affinity), there may be other circumstances where multivalent display (which can be achieved with the phage system) is desirable for binding to the receptor(s) under binding conditions that may be incompatible with intact polysomes. The same combined polysome/bacteriophage screening sequence can be used for single-chain antibodies. In one aspect of the invention a bacterial host cell is transformed or infected with a bacteriophage expression vector, which vector comprises a DNA library member which encodes a fusion protein composed of a $V_H$ and a $V_L$ in peptide linkage to the amino-terminus of a filamentous bacteriophage coat protein sequence, typically a pIII or pVIII sequence.

Another improvement to the methods of affinity screening is the control of display valency (i.e., the average number of functional scFv displayed per polysome or per phage particle), and the capacity to vary display valency in different rounds of affinity screening. Typically, a high display valency permits many binding contacts between the polysome (or phage particle) and epitope, thus affording stable binding for polysomes (or phage particles) which encode scFv species which have relatively weak binding. Hence, a high display valency system allows screening to identify a broader diversity range of scFv species, since even lower affinity scFv can be selected. Frequently, such low-to-medium affinity scFv can be superior candidates for generating very high affinity scFv, by selecting high affinity scFv from a pool of mutagenized low-to-medium affinity scFv clones. Thus, affinity sharpening by mutagenesis and subsequent rounds of affinity selection can be used in conjunction with a broader pool of initially selected scFv sequences if a high display valency method is used. Alternate rounds of high display valency screening and low display valency screening can be performed, in any order, starting from either a high or low valency system, for as many affinity screening rounds as desired, with intervening mutagenesis (directed, random, pseudorandom, CDR-clustered, etc.) and scFv sequence diversity broadening, if desired. Alternate rounds of affinity screening, wherein a first round consists of screening a scFv library expressed in a high valency display system, selecting scFv clones which bind the predetermined epitope, optionally conducting a mutagenesis step to expand the sequence kernel of the selected scFv sequence(s), expressing the selected scFv clones in a lower valency display system, and selecting scFv clones which bind the predetermined epitope, can be performed, including various permutations and combinations of multiple screening cycles, wherein each cycle can be of a similar or different display valency. This improvement affords an overall screening program that employs systems which are compatible with switchable valency (i.e., one screening cycle can have a different display valency than the other(s), and can alternate in order).

Display valency can be controlled by a variety of methods, including but not limited to controlling the average number of nascent peptides per polysome in a polysome-display system, and controlling the average number of coat protein molecules which comprise a displayed scFv sequence per phage particle. The former can be controlled by any suitable method, including: (1) altering the length of the encoding mRNA sequence to reduce or increase the frequency of translation termination (a longer mRNA will typically display more nascent peptides per polysome than a shorter MRNA encoding sequence), (2) incorporating stalling (i.e., infrequently used) codons in the encoding mRNA, typically distal (downstream, 3' of) of the scFv-encoding portion(s), (3) incorporating RNA secondary structure-forming sequences (e.g., hairpin, cruciform, etc.) distal to the scFv-encoding portion and proximal to (upstream, 5' to) the translation termination site, if any, and/or (4) including an antisense polynucleotide (e.g., DNA, RNA, polyamide nucleic acid) that hybridizes to the mRNA distal to the scFv-encoding portion and proximal to (and possibly spanning) the translation termination site, if any. The length of the mRNA may be increased to increase display valency, such as by adding additional reading frame sequences downstream of the scFv-encoding sequence(s); such additional reading frame sequences can, for example, encode the sequence (—AAVP—)$_n$, where n is typically at least 1, frequently at least 5 to 10, often at least 15 to 25, and may be at least 50–100, up to approximately 150 to 500 or more, although infrequently a longer stall sequence can be used. Stalling codons (i.e., codons which are slowly translated relative to other codons in a given translation system) can be determined empirically for any translation system, such as by measuring translation efficiency of mRNA templates which differ only in the presence or relative abundance of particular codons. For example, a set of scfv clones can be evaluated in the chosen translation system; each scfv species or the set has a stalling pblypeptide sequence of 25 amino acids, but each stalling polypeptide sequence consists of a repeating series of one codon, such that all translatable codons are represented in the set. When translated under equivalent conditions, the scFv species which produce polysomes having the highest valency (e.g., as determined by sedimentation rate, buoyancy, electron microscopic examination, and other diagnostic methods) thereby identify stalling codons as the codon(s) in the stalling polypeptide sequence.

In one embodiment, a stalling polypeptide sequence is distal (3' to) the scFv-encoding sequence, and comprises -(Gly-Gly-Gly-Gly-Ser)$_4$-A-A-V-P-(SEQ ID NO:16), or repeats thereof. A -(Gly-Gly-Gly-Gly-Ser)$_4$-A-A-V-P-(SEQ ID NO:16) is an example of a "Gly-Ser spacer".

Alternatively, or in combination with the noted variations, the valency of the target epitope may be varied to control the average binding affinity of selected scFv library members. The target epitope can be bound to a surface or substrate at varying densities, such as by including a competitor epitope, by dilution, or by other method known to those in the art. A high density (valency) of predetermined epitope can be used to enrich for scFv library members which have relatively low affinity, whereas a low density (valency) can preferentially enrich for higher affinity scfv library members.

Each of the improvements to the methods of affinity screening may be combined with other compatible improvements. For example, an in vitro transcription/translation system can be used in conjunction with a library of DNA templates synthesized in vitro (i.e. without cloning in a host cell). The resultant polysomes can be purified by one or more rounds of high-speed and/or low-speed centrifugation. The purified polysomes can be contacted with an immobilized receptor that is preblocked (e.g., with nonfat milk), and a non-ionic detergent may also be present to further reduce nonspecific binding. The selected polysomes may then be used as templates for synthesizing CDNA which is then cloned into a bacteriophage display vector, such that the variable segments of the nascent peptides are now displayed on bacteriophage. The improved methods can also be used in conjunction with the tethered nascent peptide methods (infra).

Methods for Tethered Nascent Peptide Polysomes

In one aspect, the present invention relates to an improved method for using in vitro translation to produce peptide and single-chain antibody libraries; the improvement relates to the elimination of the polysome from the screening (receptor binding step or epitope binding step).

A basis of the present invention is the physical linkage of a nascent peptide to a polynucleotide sequence complementary to or corresponding to the mRNA that served as the template for the nascent peptide's or single-chain antibody as synthesis. In this improved aspect of the invention, this physical linkage is accomplished without reliance on isolation and stability of polyribosomes (polysomes), which are problematic for a variety of reasons, including stability issues. The improved methods of the present invention avoid the need to isolate polysomes for screening nascent peptides and nascent antibodies, and thereby provide several advantages, such as affording the use of structural complexes which are more stable than polysomes and removing the ribosomes as a source of steric hindrance and nonspecific binding during subsequent screening steps.

The peptide library is generated by in vitro synthesis in a cell-free system, wherein individual library members comprise a nascent polypeptide. The nascent polypeptide (including single-chain antibody) is synthesized as a fusion protein comprising (1) a first polypeptide portion, termed the "tether segment", comprising a polypeptide sequence that binds to the encoding mRNA molecule serving as the translation template for the synthesis of the nascent polypeptide, or to a bound DNA primer or cDNA copy of such encoding mRNA, either directly or through binding an intermediate molecule that is linked directly to the encoding mRNA, DNA primer, or cDNA copy thereof, and (2) a second polypeptide portion, termed the "variable segment" or single-chain antibody portion, comprising one of a variety of possible amino acid sequence combinations represented in the library. The variable segment may be of various lengths as well as sequences, and typically peptide variable segments comprise from 2 to about 50, typically about 5 to 20, amino acid residues, although they may range from up to 50–500 residues or more for polypeptide variable segments. (See, U.S. Pat. No. 5,223,409, incorporated herein by reference.) The translation conditions selected are suitable for permitting the tether segment of the nascent polypeptide to bind to its encoding polynucleotide before significant dissociation and diffusion of the nascent peptide from the translation complex occurs, and also to reduce binding between translation complexes. It may be desirable to stall or slow the elongation cycle of ribosomal translocation to increase the probability of forming the linkage between the tether segment and the polynucleotide containing the nascent peptide coding sequence. Several strategies are available to slow or stall ribosome translocation, including but not limited to: engineering secondary structure into the mRNA species to stall translation at a predetermined site carboxy-terminal to the tether segment (and preferably carboxy-terminal to the variable segment), annealing a polynucleotide (e.g., DNA) primer to the 3' portion of the mRNA to inhibit complete translation, using rare codons at the 3' end of the coding sequence (and/or altering ratios of selected amino-acyl tRNA species in the translation reaction), and including a low concentration of translational inhibitor(s), including a translation stall sequence (e.g., may be selected from a library by selecting for stalled polysomes), among others.

Various strategies may be used to link the tether segment to the polynucleotide containing the encoding information of the nascent peptide or single-chain antibody.

Various strategies may be used to link the tether segment to the polynucleotide containing the encoding information of the nascent peptide. In a basic method of the invention, a population of messenger RNA molecules which individually encode a fusion protein comprising a common tether segment sequence and one of a variety of variable segment sequences represented in the random, pseudorandom, or defined sequence framework peptide sequence library is generated. The mRMA population can be generated by any of various methods known in the art, but in vitro transcription of synthetic DNA templates is a convenient method. For example, a plasmid containing an promoter (e.g., a T7 promoter) capable of driving in vitro transcription of an operably linked polynucleotide sequence encoding a tether segment and possessing a restriction site for insertion of a variable segment sequence(s) or single-chain antibody encoding cassette may be prepared in large scale. The plasmid can be digested with the appropriate restriction enzyme to open the site for insertion of the variable segment sequence(s) or single-chain antibody cassette(s). For generating diverse variable segments, a collection of synthetic oligonucleotides encoding random, pseudorandom, or a defined sequence kernel set of peptide sequences can be inserted by ligation into the opened site. Similarly, the sequence diversity of one or more CDRs of the single-chain antibody cassette(s) can be expanded by mutating the CDR(s) with site-directed mutagenesis, CDR-replacement, and the like. The resultant DNA molecules can be propagated in a host for cloning and amplification or can be used directly (i.e., may avoid loss of diversity which may occur upon propagation in a host cell); in either case, purified DNA is transcribed in vitro with the appropriate RNA polymerase (e.g., T7 polymerase) to form the population of mRMA molecules encoding the nascent peptide library or nascent single-chain antibody library.

The population of mRNA molecules are translated, typically in an in vitro translation system, such as a reticulocyte lysate system, wheat germ extract system, or other suitable in vitro transcription system. The cell-free continuous-flow (CFCF) translation system of Spirin et al. (1988) Science 242: 1162 may be used to increase total yield of library members, or for convenience of use, if desired. A static in vitro protein synthesis system can be used. In this system, protein synthesis generally ceases after 1 h and thus limits the time interval for creation of the library. The advantage of CFCF technology is that high level and long-term synthesis of protein should result in a much larger and more diverse library of protein-RNA complexes. The CFCF technology has been described by Spirin and co-workers as a method for the high-level synthesis of protein over an extended period of time, 24 h or longer. In addition, CFCF technology results in fractionation of the newly-synthesized protein from the translational apparatus, and thus makes it feasible to quickly sequester the protein-nucleic acid complexes from polysome-associated nucleases and proteases. Other applications of CFCF technology include an efficient method for synthesizing peptides. For example, following the identification of a peptide-fusion which binds to a target with high-affinity, the free peptide can be synthesized directly using CFCF technology and used in a binding assay.

Nascent peptide/polynucleotide complexes (library members) which encode a variable segment peptide sequence of interest or a single-chain antibody of interest are selected from the library by an affinity enrichment technique. This is accomplished by means of a immobilized macromolecule or epitope specific for the peptide sequence of interest, such as a receptor, other macromolecule, or other epitope species. Repeating the affinity selection procedure provides an enrichment of library members encoding the desired sequences, which may then be isolated for sequencing, further propagation and affinity enrichment.

The library members without the desired specificity are removed by washing. The degree and stringency of washing required will be determined for each peptide sequence or single-chain antibody of interest and the immobilized predetermined macromolecule or epitope. A certain degree of control can be exerted over the binding characteristics of the nascent peptide/DNA complexes recovered by adjusting the conditions of the binding incubation and the subsequent washing. The temperature, pH, ionic strength, divalent cations concentration, and the volume and duration of the washing will select for nascent peptide/DNA complexes within particular ranges of affinity for the immobilized macromolecule. Selection based on slow dissociation rate, which is usually predictive of high affinity, is often the most practical route. This may be done either by continued incubation in the presence of a saturating amount of free predetermined macromolecule, or by increasing the volume, number, and length of the washes. In each case, the rebinding of dissociated nascent peptide/DNA or peptide/RNA complex is prevented, and with increasing time, nascent peptide/DNA or peptide/RNA complexes of higher and higher affinity are recovered.

Additional modifications of the binding and washing procedures may be applied to find peptides with special characteristics. The affinities of some peptides are dependent on ionic strength or cation concentration. This is a useful characteristic for peptides that will be used in affinity purification of various proteins when gentle conditions for removing the protein from the peptides are required.

One variation involves the use of multiple binding targets (multiple epitope species, multiple receptor species), such that a polysome scFv library can be simultaneously screened for a multiplicity of scFv which have different binding specificities. Given that the size of a scfv library often limits the diversity of potential scFv sequences, it is typically desirable to use scFv libraries of as large a size as possible. The time and economic considerations of generating a number of very large polysome scFv-display libraries can become prohibitive. To avoid this substantial problem, multiple predetermined epitope species (receptor species) can be concomitantly screened in a single library, or sequential screening against a number of epitope species can be used. In one variation, multiple target epitope species, each encoded on a separate bead (or subset of beads), can be mixed and incubated with a polysome-display scFv library under suitable binding conditions. The collection of beads, comprising multiple epitope species, can then be used to isolate, by affinity selection, scfv library members. Generally, subsequent affinity screening rounds can include the same mixture of beads, subsets thereof, or beads containing only one or two individual epitope species. This approach affords efficient screening, and is compatible with laboratory automation, batch processing, and high throughput screening methods.

A variety of techniques can be used in the present invention to diversify a peptide library or single-chain antibody library, or to diversify around variable segment peptides or $V_H$, $V_L$, or CDRs found in early rounds of panning to have sufficient binding activity to the predetermined macromolecule or epitope. In one approach, the positive nascent peptide/polynucleotide complexes (those identified in an early round of affinity enrichment) are sequenced to determine the identity of the active peptides. Oligonucleotides are then synthesized based on these active peptide sequences, employing a low level of all bases incorporated at each step to produce slight variations of the primary oligonucleotide sequences. This mixture of (slightly) degenerate oligonucleotides is then cloned into the variable segment sequences at the appropriate locations. This method produces systematic, controlled variations of the starting peptide sequences. It requires, however, that individual positive nascent peptide/polynucleotide complexes be sequenced before mutagenesis, and thus is useful for expanding the diversity of small numbers of recovered complexes and selecting variants having higher binding affinity and/or higher binding specificity. In a variation, mutagenic PCR amplification of positive nascent peptide/polynucleotide complexes (especially of the variable region sequences, the amplification products of which may be ligated to tether sequences and operably linked to an in vitro promoter) is performed and one or more additional rounds of screening is done prior to sequencing. The same general approach can be employed with single-chain antibodies in order to expand the diversity and enhance the binding affinity/specificity, typically by diversifying CDRs or adjacent framework regions.

In a method of the invention, a peptide library is generated by in vitro synthesis in a cell-free system, wherein individual library members comprise a nascent polypeptide comprising a first polypeptide portion linked to a polynucleotide encoding said nascent polypeptide (or a polynucleotide complementary to the encoding polynucleotide sequence) and a second polypeptide portion having a variable amino acid sequence, at least in part, in peptide linkage to said first polypeptide portion. The nascent polypeptide is synthesized as a fusion protein comprising (1) a first polypeptide portion, termed the "tether segment", comprising a polypeptide sequence which binds to the encoding mRNA molecule serving as the translation template for the synthesis of the nascent polypeptide, or to a cDNA copy of such encoding mRNA, either directly or through binding an intermediate molecule that is linked directly to the encoding mRNA or cDNA copy thereof, and (2) a second polypeptide portion, termed the "variable segment", comprising one of a variety of possible amino acid sequence combinations represented in the library. The tether segment serves to link the variable segment of an individual library peptide to the polynucleotide comprising the sequence information encoding the amino acid sequence of the individual library peptide's variable segment. The linked polynucleotide of a library member provides the basis for replication of the library member after a screening or selection procedure, and also provides the basis for the determination, by nucleotide sequencing, of the identity of the variable segment amino acid sequence.

Tether-Binding Antibody Linked to Polynucleotide

An antibody known to bind with high affinity to a particular peptide sequence is attached to the 5' or 3'-end of the RNA molecules or to the 50 end of a DNA primer annealed to the mNA molecules. This can be done through an avidin-biotin bridge or via homo-or heterobifunctional cross-linkers of amine, carboxyl, or thiol on the antibody to amine or thiol on the RNA or DNA primer. The sequence encoding the peptide epitope for this antibody is encoded by all the RNA molecules in the library as the tether segment; this tether segment sequence is placed either to the 5' or the 3' side of the variable segment sequence. During in vitro translation, the nascent epitope (tether segment) can bind to the attached antibody with an affinity high enough to allow dissociation of the polysome (by EDTA treatment, for example) and isolation of the intact mRNA-antibody-epitope-variable peptide complex ready for screening.

A modification of this strategy comprises the attachment by any of the means described above of the antibody to a segment of DNA that can hybridize to the 3' end of the RNA. The attractive features of this scheme are: first, the hybrid may serve to block the dissociation of the ribosome, allowing more time for the more stable complex to form; second, the DNA segment is a generic reagent that can be prepared in large amount (with or without the attached antibody) independent of the construction of a particular library; third, the DNA can be extended after translation to provide a more stable form of the sequence information (DNA is generally less vulnerable to degradation than is RNA).

The general steps are as follows:

(1) A complementary DNA fragment of 10 to several hundred bases is hybridized to the RNA library (e.g., a primer comprising a specific sequence complementary to the known 3' end of the mRNA species or oligo(dT) if the RNA comprises a poly(A) tail. In some embodiments, the RNA may comprise a polyadenylated tail, which may stabilize the RNA template in some in vitro translation reactions (e.g., reticulocyte lysate). The complementary DNA primer may be attached to the antibody prior to hybridization, or it may simply be modified so as to bind the antibody after translation of the RNA has been performed. In either case, the mode of attachment may be one of those proposed above. By way of example, a 5'-biotin is attached to the DNA; an excess of streptavidin is added to occupy all the biotins, and the unbound streptavidin is removed; a biotinylated antibody is added to bind to the DNA-streptavidin complexes, and the excess antibody is removed. Note that a monovalent form of the complex can be formed using Fab', a bivalent complex can be formed with IgG, or a multivalent complex formed by adding a string of biotins to the DNA to bind several streptavidin molecules and consequently several antibodies;

(2) The epitope sequence (tether segment) encoded by the mRNA is expressed and binds to the antibody. A variable segment peptide can be displayed with a free C-terminus if fused to the C-terminus of the attachment epitope (tether segment) or with a free N-terminus if fused to the N terminus of the tether segment (note that in the latter case, the N-terminal F-met is preferably removed by aminopeptidase or by treatment with a specific protease);

(3) The ribosome is dissociated with EDTA;

(4) The DNA primer is extended with reverse transcription (AMV reverse transcriptase under standard conditions) of the RNA template;

(5) At this point the RNA may be removed with RNAse treatment, but this is not necessary. The library member consists of the displayed peptide-antibody-cDNA (and hybridized RNA) complex.

It is generally preferable to include an inhibitor of RNase activity (e.g., vanadyl ribonucleoside complexes, RNAsin) in the in vitro translation reaction and all steps prior to the synthesis of the first-strand CDNA.

Biotinylated Tether Segment

A variation on the theme that avoids the use of an antibody substitutes a "biotinylation substrate" (BS) for the epitope as the tether segment, and streptavidin for the antibody. The biotinylation substrate is a sequence that is recognized by a prokaryotic enzyme, biotin holoenzyme synthetase (BirA) which attaches a biotin to a lysine in the recognition sequence. Inclusion of the enzyme in the translation mix, or treatment of the polysomes with the enzyme following translation biotinylates the nascent peptide, which can then bind to a streptavidin molecule attached to either end of the mRNA or to the small DNA primer hybridized to the RNA. Streptavidin may be attached to the mRNA or DNA primer by direct covalent linkage or via biotin moieties incorporated into the polynucleotides or covalently attached to the 5' end of the polynucleotide; however, the biotinylation of the mRNA (or DNA primer) preferably does not adversely affect translational efficiency of the mRNA template for translation of the tether segment or variable segment.

Streptavidin is a bacterial protein which binds the water soluble vitamin, biotin, with high affinity. It is possible to attach biotin to RNA (or DNA), and thus convert streptavidin to an RNA-binding protein through a biotin linkage. It is also possible to fuse heterologous proteins to the C-terminus of streptavidin without affecting functional binding to biotin. Thus, for the purpose of peptide libraries, it will be possible to fuse a variable segment to a tether segment comprising the C-terminus of streptavidin. Biotin can be attached to the 5° end of mRNA using chemical modification, or incorporated into the mRNA by in vitro transcription using biotinylated nucleotide analogs.

RNA-Binding Protein Sequence as Tether Segment

Another variation of the invention involves the use of an RNA-binding protein such as Tat fused to the variable segment peptide sequence to provide a linkage between the peptide and the encoding polynucleotide or at least increase the residence time of the peptide on the mRNA and thereby improve the efficiency with which the high affinity epitope-antibody or biotin-streptavidin complex can form. Tat or small peptide derivatives of Tat can be used to produce nascent peptide-polynucleotide complexes.

The human immunodeficiency virus (HIV) protein Tat is a strong activator of viral gene transcription. The Tat protein stimulates transcription by binding to a specific RNA sequence (Tar) located at the 5° end of the Tat mRNA. There are several features of the Tat/Tar complex that are useful for the method described. For example, Tat binds Tar with relatively high affinity. The dissociation constant (Kd) for the Tat/Tar complex is 5 nM, but the inclusion of a non-ionic detergent reduces the Kd to approximately 100 pM. Peptides that bind to Tar with higher affinity may be selected by panning phage display peptide libraries against immobilized RNA comprising a Tar sequence. Further, the minimum size of Tat protein and Tar RNA required for binding are small and defined. Tat is a 86 residue protein, but only the last 24 residues of the carboxy terminus are required for high-affinity binding. The Tar stem-loop structure includes only 57 nucleotides but can be shortened to 27 nucleotides without affecting binding. Also, the conformation of the Tar RNA has been solved by NMR spectroscopy. Moreover, Tat binds to Tar as a fusion protein. There are at least two examples of functional fusions to the carboxy-terminus of Tat. The first is a fusion to the viral Rev protein, and the second is a fusion to the coat protein of bacteriophage MS2. Thus, a random peptide library based on peptides fused to the C-terminus of Tat will function properly, as such fusions do not significantly adversely affect RNA binding. Finally, Tat binds to Tar as a monomer. This feature may prove useful in controlling the valency of peptide display by varying the number of Tar binding sites. Thus, libraries that are either monovalent or multivalent can be generated.

Thus, as an example of these variations of the invention, a Tar sequence, such as a 57 base to 27 base binding sequence (Weeks KM and Crothers DM (1991) *Cell* 66:577, incorporated herein by reference), can be included in the mRNA sequence, preferably near the translation start site, to allow attachment of a Tat tether segment of the nascent peptide to the mRNA. The RNA-binding tether (e.g., Tat segment) will inhibit further translational starts on the RNA templates Another suitable RNA-binding protein for use as a tether in fusions is the iron response element binding protein (IREBP), which interacts specifically with the iron response element (IRE) located at the 51 of the ferritin mRNA and 3' untranslated region of the transferrin receptor mRNA. The protein binds as a monomer with a dissociation constant of 20–50 pM (Swenson et al. (1991) *Biol Met.* 4:48). The IREBP (98.4 kDal) is active in binding to the IRE after being translated in vitro (Hirling et al (1992) *Nucleic Acids Res.* 20: 33). Thus, a RNA-binding tether can comprise a IREBP and the mRNA can comprise an IRE; the RNA-binding IREBP tether segment bind to an IRE sequence in each MRNA and inhibits further translational activity of the bound mRNA.

Polysome Stalling

Peptide display on polysomes requires efficient stalling of ribosomes prior to screening the nascent peptides. A method is to allow the in vitro translation reaction to incubate for about 30 minutes prior to adding the antibiotic chloramphenicol which binds irreversibly to the polysome complexes and arrests translation elongation. Under these conditions, the rate of protein synthesis reaches steady state and the polysome complexes after chloramphenicol addition are likely to be comprised of a mixture of ribosomes that are either still initiating or have translated varying lengths of the nascent peptide. For screening libraries, it is desirable to have a large fraction of ribosomes stalled at a distal site on the mRNA prior to chloramphenicol addition. In addition to stalling strategies based on the use of rare codons or antisense oligonucleotides to sequester a short stretch of the mRNA and prevent it from being translated, an additional method relies on a short nascent peptide sequence acting in cis to stall ribosomal elongation by inhibiting the peptidyl transferase activity of the 50S subunit.

Peptide coding sequences within the leader regions of two attenuation regulated chloramphenicol genes, cat and cmLA can be used to accomplish polysome stalling by incorporation of the sequence(s) in the nascent polypeptide encoded by the polysome mRNA. Each peptide is a potent inhibitor of peptidyl transferase and acts in cis to stall the ribosome at a specific site on the leader that is essential for induction by chloramphenicol. The peptide sequences encoded by the cat and cmLA leaders are MVKTD (SEQ ID NO:11) and MSTSKNAD (SEQ ID NO:12) respectively. The cmlA 8-mer peptide is about 50% as inhibitory as chloramphenicol and about 5-fold more inhibitory than the cat 5-mer on peptidyl transferase activity of 50S ribosomal subunits. A free N-terminus is not required for the peptide's activity.

The coding sequence for the 8-mer peptide MSTSKNAD can be placed at the 3' end of the constant Gly-Ser spacer region. Inhibitor peptides which are efficient in stalling ribosomes at the 3' end of the spacer region, typically produce a larger fraction of the total polysome pool which bind to the target molecule as compared to a nascent peptide polysomes lacking, the encoded inhibitor peptide. Efficient ribosome stalling at the distal 3' site can also result in additional ribosomes translating each MRNA and providing multivalent display of the nascent peptides. This can be determined by measuring the polysome binding efficiency or enrichment of a low affinity peptide ligand.

Examples of such inhibitory polypeptide sequences include, but are not limited to, —MVKTD— (SEQ ID NO:11) and —MSTSKNAD—(SEQ ID NO:12) Typically, such elongation inhibitory polypeptide segments are present in the amino-terminal half of the nascent polypeptide, often within about 50 amino acids or less of the amino-terminus, or can be amino-terminal. A nascent polypeptide can comprise one or a plurality of elongation inhibitory polypeptide segments, which may comprise identical sequences or different sequences. In an embodiment, the elongation inhibitory polypeptide segment(s) are located within 5 residues amino-terminal of a Gly-Ser spacer region; typically immediately amino-terminal to the Gly-Ser spacer region, or other spacer region, if present. It is believed to be unnecessary for a spacer sequence to be present.

Amplification, Affinity Enrichment, and Screening

A basic method is described for synthesizing a nascent peptide-polysome library and nascent single-chain antibody-polysome library in vitro, screening and enrichment of the library for species having desired specific receptor-binding or epitope-binding properties, and recovery of the nucleotide sequences that encode those peptides or antibodies of sufficient binding affinity for receptor or epitope (e.g., immobilized receptor or epitope) sufficient for selection by affinity selection (e.g, panning, affinity chromatography). Although the method is described with reference to nascent peptide libraries, the method is also applicable to synthesizing and screening nascent single-chain antibody libraries.

The library consists of a population of nascent peptide library members comprising nascent peptides, with the peptides comprising a variable sequence segment (such as a random peptide sequence), fused to a specific tether segment to permit binding of the variable sequence to its own encoding mRNA or a cDNA copy thereof. These RNA-protein complexes (or DNA-protein complexes) are screened for high affinity binding to a particular receptor (e.g., a peptide hormone receptor). After selecting those nascent peptide library members that bind to the ligand with high affinity, the selected complexes are disrupted and the mRNA (or DNA) is recovered and amplified to create DNA copies of the message, typically each copy comprises an operably linked in vitro transcription promoter (e.g., T7 or SP6 promoter) The DNA copies are transcribed in vitro to produce mRNA, and the process is repeated to enrich for peptides that bind with sufficient affinity. Unlike the other in vitro methods that rely on intact polysomes for screening, the present method's screening of desired peptides in vitro is accomplished without the necessity of maintaining intact polysomes. Thus, many of the problems inherent to immunopurification of polysomes are avoided, and conditions which disrupt intact polysomes may be used for screening conditions, if desired.

The following general steps are frequently followed in the method: (1) generate a DNA template which is suitable for in vitro synthesis of mRNA, (2) synthesize mRNA in vitro by transcription of the DNA template(s) and add to an in vitro translation system, (3) bind the nascent peptide tether to its own mRNA or a DNA primer which will hybridize to the encoding mRNA (and preferably prime cDNA synthesis of it), (4) screen the resultant nascent peptide library members for receptor-binding, (5) recover and amplify nascent peptide library members which bind the receptor and produce DNA templates from the selected library members competent for in vitro transcription.

Each generated DNA template preferably contains a promoter (e.g., T7 or SP6) which is active in an in vitro transcription system. A DNA template generally comprises (1) a promoter which is functional for in vitro transcription and operably linked to (2) a polynucleotide sequence encoding an mRNA period. Said encoded mRNA comprises a polynucleotide sequence which: (1) encodes a polypeptide comprising a tether segment and a variable segment (in either spatial order from amino- to carboxy-terminal), (2) a polynucleotide sequence to which the tether can bind and/or to which a DNA primer suitable for priming first-strand cDNA synthesis of the mRNA can bind, and (3) a ribosome-binding site and other elements necessary for in vitro translatability of the mRNA, and optionally, for MRNA stability and translatable secondary structure, if any.

In embodiments where the tether is a peptide which binds to a particular RNA sequence (e.g, Tar or a biotinylation sequence), the polynucleotide sequence to which the tether binds is referred to as a "target site".

The target site for the tether segment is frequently near the 5' end of the MRNA non-coding sequence, but may be located anywhere on the mRNA to facilitate binding to the nascent peptide tether segment. If the target site is located near the ribosome binding site, binding of the tether segment will preferably prevent reinitiation of translation and thus enhance the probability that only one protein per unit mRNA is synthesized in the system. The DNA templates of the library are transcribed, typically in vitro, to produce a population of translatable mRNA molecules encoding distinct variable segment sequences (i.e, a library). Frequently, the DNA templates comprise a T7 or SP6 promoter operably linked to the sequence encoding the tether and variable segments. The mRNA library members produced as transcription products of the DNA templates are then translated in vitro using an efficient in vitro translation system (e.g., using an E. coli S30 coupled transcription-translation system). The translation products are fusion proteins and may be non-terminated translation products (i.e., nascent peptides) attached to the encoding mRNA -via the translating ribosome.

The encoded fusion protein (nascent peptide) generally comprises of a tether segment fused to a variable segment that is frequently one member of a random library of peptide sequences from about 5 to 20 amino acids in length, but may be longer or shorter as discussed (supra). The fusion junction between the tether and variable region may be at the N-terminus or C-terminus of the tether segment, depending on the conditions necessary for optimal binding to the mRNA or DNA. The tether segment and the variable segment may be separated by a polypeptide spacer if desired; generally, such a spacer is less than 500 amino acids. A single fusion protein (nascent peptide) may comprise multiple tether segments and/or variable segments, and/or spacer segments.

For tethered nascent peptides that bind the encoding mRNA, it is generally important that the nascent peptide fold properly and bind to its own XRNA before release from the ribosome, or shortly thereafter in dilute conditions. This may be accomplished by slowing or arresting the elongation cycle of translation by including at the 3' end of the mRNA a series of rare codons or a hybridization sequence for an antisense primer (e.g., DNA, RNA, PNA) and secondary structure sequences.

Following translation, polysomes are isolated and ribosomes released by the addition of EDTA sufficient to chelate the $Mg^{+2}$ present in the buffer. Ribosomes are removed by high-speed centrifugation, and the RNA/protein complexes are screened for high-affinity receptor-binding using standard procedures and as described herein.

After selecting those nascent peptide/polynucleotide complexes that bind with sufficient affinity, the RNA component is released by phenol extraction, or by changing the ionic strength, temperature or pH of the binding buffer so as to denature the nascent peptide. A cDNA copy of the mRNA is made using reverse transcriptase, and the CDNA copy is amplified by the polymerase chain reaction (PCR). The amplified CDNA is added to the in vitro transcription system and the process is repeated to enrich for those peptides that bind with high affinity.

Alternatively, where the nascent peptide is linked to a DNA primer, the primer is extended by reverse transcription to form nascent peptide/DNA complexes prior to affinity screening. The residual mRNA sequences, if any, may be removed (e.g., by RNAse H or base hydrolysis), if desired, prior to or after affinity screening.

Use of Error-Prone Polynucleotide Amplification

Error-prone polynucleotide amplification can be included in the present method. Typically, one or more rounds of error-prone PCR is used to introduce mutations into the pool(s) of selected library members of a polysome display library. The idea is to mutagenize pools of clones using error-prone PCR rather than requiring isolation of one or more individual clones to base the construction of a mutagenesis library. The method employs a suitable error-prone amplification methodology; an error-prone PCR protocol has been shown to make possible the control of the mutagenesis rate of the error-prone PCR process through serial dilution and repeated mutagenesis (Bartel and Szostak Science 261: 1411, incorporated herein by reference).

One of the potential advantages to screening peptide libraries with polysomes is the ability to incorporate mutagenesis between rounds of panning. This can be accomplished by substituting error prone PCR for normal PCR during one or more amplification steps of one or more amplification rounds.

For polysome libraries, normal PCR is typically used first to amplify the peptide regions of the entire pool of phage isolated from a round of panning, found to contain positive library members. Alternatively, pools from different rounds containing positive clones could be amplified separately and the products mixed. A portion of the mixture is then reamplified using error-prone PCR and the mutagenized fragments are cloned back into a suitable polysome expression vector and screened by one or more additional rounds of affinity selection fof high affinity library members. By comparing the sequences and affinities of the selected high affinity clones, it can be possible to determine the optimal mutagenic frequencies.

A round of amplification can comprise one or more cycles of error-prone PCR, often in combination with one or more cycles of conventional PCR. The method can comprise serial dilution and subsequent rounds of error-prone PCR amplification of error-prone PCR products, and may include the further variation of pooling aliquots from each serial dilution round to form a final mutated pool comprising mutated variants representing varying degrees of mutation. In this variation, a selected library member or a selected subpopulation of library members is subjected to a first error-prone amplification round comprising at least one cycle of error-prone PCR; an aliquot of the amplification product is removed and subjected to at least one subsequent error-prone amplification round comprising at least one cycle of error-prone PCR prior to selection. Amplification products from at least one, preferably all, error-prone amplification round(s) are pooled, typically in approximately equimolar ratios, forming a pool of mutated variants representating a spectrum of mutational frequencies. Following error-prone PCR amplification, alone or in combination with conventional amplification methods, the mutated amplification products are subjected to at least one round of selection according to the method of the invention.

In a variation of the invention, the method can be used in conjunction with a selection target which comprises or consists of a small molecule (e.g., an organic compound less than about 2,500 Daltons), such as a pharmacophore, enzyme substrate, receptor ligand, and the like. Typically, the small molecule is immobilized on a support, typically a solid support such as beads, affinity chromatography matrix, or other suitable substrate such that it retains selective binding affinity for polypeptides which are predetermined to bind to it. The immobilized small molecule, or collection thereof, is used to selectively enrich for library members which bind to the immobilized small molecule, thereby facilitating removal, typically by washing, of unbound library members and consequently producing selective enrichment for library members which are retained by binding to the immobilized small molecule(s).

Single-Chain Antibodies

The single-chain antibodies produced and isolated by the method of the invention are selected to bind a predetermined epitope. Typically, the predetermined epitope will be selected in view of its applicability as a diagnostic and/or therapeutic target. Several reports of the diagnostic and therapeutic utility of scFv have been published (Gruber et al (1994) op.cit.; Lilley et al. (1994) op.cit.; Huston et al. (1993) Int. Rev. Immunol 10:a 195,Sandhu JS (1992) Crit. Rev. Biotechnol. 12: 437).

Such single-chain antibodies generally bind to a predetermined antigen (e.g., the immunogen) with an affinity of about at least $1\times10^7$ $M^{-1}$, preferably with an affinity of about at least $5\times10^7$ $M^{-1}$ more preferably with an affinity of at least $1\times10^8$ $M^{-1}$ to $1\times10^9$ M-1 or more, sometimes up to $1\times10^{10}M^{-1}$ or more.. Frequently, the predetermined antigen is a human protein, such as for example a human cell surface antigen (e.g., CD4, CD8, IL-2 receptor, EGF receptor, PDGF receptor), other human biological macromolecule (e.g., thrombomodulin, protein C, carbohydrate antigen, sialyl Lewis antigen, L-selectin), or nonhuman disease associated macromolecule (e.g., bacterial LPS, virion capsid protein or envelope glycoprotein) and the like.

High affinity single-chain antibodies of the desired specificity can be engineered and expressed in a variety of systems. For example, scFv have been produced in plants (Firek et al. (1993) Plant Mol. Biol. 23: 861) and can be readily made in prokaryotic systems (Owens RJ and Young RJ (1994) J. Immunol. Meth. 168: 149; Johnson S and Bird RE (1991) Methods Enzymol. 203: 88). Furthermore, the single-chain antibodies can be used as a basis for constructing whole antibodies or various fragments thereof (Kettleborough et al. (1994) Euro J. Immunol. 24: 952). The variable region encoding sequence may be isolated (e.g., by PCR amplification or subcloning) and spliced to a sequence encoding a desired human constant region to encode a human sequence antibody more suitable for human therapeutic uses where immunogenicity is preferably minimized. The polynucleotide(s) having the resultant fully human encoding sequence(s) can be expressed in a host cell (e.g., from an expression vector in a mammalian cell) and purified for pharmaceutical formulation.

The DNA expression constructs will typically include an expression control DNA sequence operably linked to the coding sequences, including naturally-associated or heterologous promoter regions. Preferably, the expression control sequences will be eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the mutant "engineered" antibodies.

As stated previously, the DNA sequences will be expressed in hosts after the sequences have been operably linked to an expression control sequence (i.e., positioned to ensure the transcription and translation of the structural gene). These expression vectors are typically replicable in the host organisms either as episomes or as an integral part of the host chromosomal DNA. Commonly, expression vectors will contain selection markers, e.g., tetracycline or neomycin, to permit detection of those cells transformed with the desired DNA sequences (see, e.g., U.S. Pat. No. 4,704,362, which is incorporated herein by reference).

In addition to eukaryotic microorganisms such as yeast, mammalian tissue cell culture may also be used to produce the polypeptides of the present invention (see, Winnacker, "From Genes to Clones," VCH Publishers, N.Y., N.Y. (1987), which is incorporated herein by reference). Eukaryotic cells are actually preferred, because a number of suitable host cell lines capable of secreting intact immunoglobulins have been developed in the art, and include the CHO cell lines, various COS cell lines, HeLa cells, myeloma cell lines, etc, but preferably transformed B-cells or hybridomas. Expression vectors for these cells can include expression control sequences, such as an origin of replication, a promoter, an enhancer (Queen et al. (1986) *Immunol. Rev.* 89: 49), and necessary processing information sites, such as ribosome binding sites, RNA splice sites, polyadenylation sites, and transcriptional terminator sequences. Preferred expression control sequences are promoters derived from immunoglobulin genes, cytomegalovirus, SV40, Adenovirus, Bovine Papilloma Virus, and the like.

Eukaryotic DNA transcription can be increased by inserting an enhancer sequence into the vector. Enhancers are cis-acting sequences of between 10 to 30 obp that increase transcription by a promoter. Enhancers can effectively increase transcription when either 5' or 3' to the transcription unit. They are also effective if located within an intron or within the coding sequence itself. Typically, viral enhancers are used, including SV40 enhancers, cytomegalovirus enhancers, polyoma enhancers, and adenovirus enhancers. Enhancer sequences from mammalian systems are also commonly used, such as the mouse immunoglobulin heavy chain enhancer.

Mammalian expression vector systems will also typically include a selectable marker gene. Examples of suitable markers include, the dihydrofolate reductase gene (DHFR), the thymidine kinase gene (TK), or prokaryotic genes conferring drug resistance. The first two marker genes prefer the use of mutant cell lines that lack the ability to grow without the addition of thymidine to the growth medium. Transformed cells can then be identified by their ability to grow on non-supplemented media. Examples of prokaryotic drug resistance genes useful as markers include genes conferring resistance to G418, mycophenolic acid and hygromycin.

The vectors containing the DNA segments of interest can be transferred into the host cell by well-known methods, depending on the type of cellular host. For example, calcium chloride transfection is commonly utilized for prokaryotic cells, whereas calcium phosphate treatment. lipofection, or electroporation may be used for other cellular hosts. Other methods used to transform mammalian cells include the use of Polybrene, protoplast fusion, liposomes, electroporation, and microinjection (see, generally, Sambrook et al., supra).

Once expressed, the antibodies, individual mutated immunoglobulin chains, mutated antibody fragments, and other immunoglobulin polypeptides of the invention can be purified according to standard procedures of the art, including ammonium sulfate precipitation, fraction column chromatography, gel electrophoresis and the like (see, generally, Scopes, R., *Protein Purification,* Springer-Verlag, N.Y. (1982)). Once purified, partially or to homogeneity as desired, the polypeptides may then be used therapeutically or in developing and performing assay procedures, immunofluorescent stainings, and the like (see, generally, *Immunological Methods,* Vols. I and II, Eds. Lefkovits and Pernis, Academic Press, N.Y. N.Y. (1979 and 1981))

The antibodies of the present invention can be used for diagnosis and therapy. By way of illustration and not limitation, they can be used to treat cancer, autoimmune diseases, or viral infections. For treatment of cancer, the antibodies will typically bind to an antigen expressed preferentially on cancer cells, such as erbB-2, CEA, CD33, and many other antigens well known to those skilled in the art. For treatment of autoimmune disease, the antibodies will typically bind to an antigen expressed on T-cells, such as CD4, the IL-2 receptor, the various T-cell antigen receptors and many other antigens well known to those skilled in the art (e.g., see *Fundamental Immunology,* 2nd ed., W. E. Paul, ed., Raven Press: New York, N.Y., which is incorporated herein by reference). For treatment of viral infections, the antibodies will typically bind to an antigen expressed on cells infected by a particular virus such as the various glycoproteins (e.g., gB, gD, gE) of herpes simplex virus and cytomegalovirus, and many other antigens well known to those skilled in the art (e.g., see Virology, 2nd ed., B. N. Fields et al., eds., (1990), Raven Press: New York, N.Y.).

Pharmaceutical compositions comprising antibodies of the present invention are useful for parenteral administration, i.e., subcutaneously, intramuscularly or intravenously. The compositions for parenteral administration will commonly comprise a solution of the antibody or a cocktail thereof dissolved in an acceptable carrier, preferably an aqueous carrier. A variety of aqueous carriers can be used, e.g., water, buffered water, 0.4% saline, 0.3% glycine and the like. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. The concentration of the mutant antibodies in these formulations can vary widely, i.e., from less than about 0.01%, usually at least about 0.1% to as much as 5% by weight and will be selected primarily based on fluid volumes, viscosities, etc., in accordance with the particular mode of administration selected.

Thus, a typical pharmaceutical composition for intramuscular injection could be made up to contain 1 ml sterile buffered water, and about 1 mg of mutant antibody. A typical composition for intravenous infusion can be made up to contain 250 ml of sterile Ringer's solution, and 10 mg of mutant antibody. Actual methods for preparing parenterally administrable compositions will be known or apparent to those skilled in the art and are described in more detail in, for example, *Remington's Pharmaceutical Science*, 15th Ed., Mack Publishing Company, Easton, Pa. (1980), which is incorporated herein by reference.

CDR Diversification

The present invention enables the generation of a vast library of CDR-variant single-chain antibodies. One way to generate such antibodies is to insert synthetic CDRs into the single-chain antibody and/or CDR randomization. The sequences of the synthetic CDR cassettes are selected by referring to known sequence data of human CDR and are selected in the discretion of the practitioner according to the following guidelines: synthetic CDRs will have at least 40 percent positional sequence identity to known CDR sequences, and preferably will have at least 50 to 70 percent positional sequence identity to known CDR sequences. For example, a collection of synthetic CDR sequences can be generated by synthesizing a collection of oligonucleotide sequences on the basis of naturally-occurring human CDR sequences listed in Kabat et al. (1991) op cit.; the pool(s) of synthetic CDR sequences are calculated to encode CDR peptide sequences having at least 40 percent sequence identity to at least one known naturally-occurring human CDR sequence. Alternatively, a collection of naturally-occurring CDR sequences may be compared to generate consensus sequences so that amino acids used at a residue position frequently (i.e., in at least 5 percent of known CDR sequences) are incorporated into the synthetic CDRs at the corresponding position(s). Typically, several (e.g., 3 to about 50) known CDR sequences are compared and observed natural sequence variations between the known CDRs are tabulated, and a collection of oligonucleotides encoding CDR peptide sequences encompassing all or most permutations of the observed natural sequence variations is synthesized. For example but not for limitation, if a collection of human $V_H$ CDR sequences have carboxy-terminal amino acids which are either Tyr, Val, Phe, or Asp, then the pool(s) of synthetic CDR oligonucleotide sequences are designed to allow the carboxy-terminal CDR residue to be any of these amino acids. In some embodiments, residues other than those which naturally-occur at a residue position in the collection of CDR sequences are incorporated: conservative amino acid substitutions are frequently incorporated and up to 5 residue positions may be varied to incorporate non-conservative amino acid substitutions as compared to known naturally-occurring CDR sequences. In general, the number of unique oligonucleotide sequences included should not exceed the number of primary transformants expected in the bacteriophage-display or polysome-display library by more than about ten-fold. Construction of such pools of defined and/or degenerate sequences will be readily accomplished by those of ordinary skill in the art.

The collection of synthetic CDR sequences comprises at least one member that is not known to be a naturally-occurring CDR sequence. It is within the discretion of the practitioner to include or not include a portion of random or pseudorandom sequence corresponding to N region addition in the heavy chain CDR; the N region sequence ranges from 1 nucleotide to about 4 nucleotides occurring at V-D and D-J junctions. A collection of synthetic heavy chain CDR sequences comprises at least about 100 unique CDR sequences, typically at least about 1,000 unique CDR sequences, preferably at least about 10,000 unique CDR sequences, frequently more than 50,000 unique CDR sequences; however, usually not more than about $1 \times 10^6$ unique CDR sequences are included in the collection, although occasionally $1 \times 10^7$ to $1 \times 10^8$ unique CDR sequences are present, especially if conservative amino acid substitutions are permitted at positions where the conservative amino acid substituent is not present or is rare (i.e., less than 0.1 percent) in that position in naturally-occurring human CDRs. In general, the number of unique CDR sequences included in a library should not exceed the expected number of primary transformants in the library by more than a factor of 10.

The broad scope of this invention is best understood with reference to the following examples, which are not intended to limit the invention in any manner. The following examples are offered by way of illustration, not by way of limitation.

EXPERIMENTAL EXAMPLES

Oligonucleotide Sequences

M represents A or C; K represents G or T; and N represents A, C, T, or G)

ON1747:

5'd (AAATTTCCAACGCCCTGGGTACC (MNN)$_{10}$ GCTAGCCATATGTATATCTCCTTCTT)3' or in alternative notation:

5'd (AAATTTCCAACGCCCTGGGTACCMNMNM- NHNNNNMNNNNMNNNMNHNGCTAGC CATATG- TATATCTCCTTCTT)30'SEQ ID NO:17

ON3150:

5'd(ACCTGGGCCATGGCCGGCTGGGCCGCAT)3' SEQ ID NO:18

ON3149:

5'd(TCTCCGGGAGCTGCATGTGTC)30' SEQ ID NO:19

ON3147:

5'd(ATGCGGCCCAGCCGGCCATGGCCCAGGT)3' SEQ ID NO:20

ON3148:

5'd(CAGTTTCTGCGGCCGCACGTTTGAT)3' SEQ ID NO:21

ON3193:

5'd (ATCAAACGTGCGGCCGCAGAAACTGTTGA- ATTC)3' SEQ ID NO:22

ON2970:

5'd (AATTGGAGGATCGTGCATGTGAC)3' SEQ ID NO: 23

ON1543:

5'd (ACTTCGAAATTAATACGACTCACTATAGGGA- GACCACAACGGTTTCCCTC TAGAAATAATTT- TGTTTAACTTTAAGAAGGAGATATACAT)3' SEQ ID NO: 24

EXAMPLE 1

Overview

A DNA library encoding approximately $10^{12}$ different decapeptide sequences was synthesized and incubated in an *Escherichia coli* S30 coupled transcription/translation system. Polysomes were isolated by centrifugation and added to microtiter wells containing an immobilized monoclonal antibody specific for the peptide dynorphin B as a model receptor. Following affinity selection of nascent peptides, the enriched pool of polysomal mRNA was recovered, reverse transcribed to cDNA and amplified by the polymerase chain reaction (PCR) to produce template for the next round of in vitro synthesis and selection. A portion of the amplified template pool following each round was cloned and the random region sequenced. After four rounds of affinity selection, the majority of clones contained a consensus sequence that was similar to the known high-affinity epitope for the antibody. Peptides corresponding to several of these sequences were synthesized and found to have binding affinities ranging from 7 to 140 nM. The in vitro polysome system described here is capable of screening peptide libraries that are three to six orders of magnitude larger than current biological peptide expression systems.

The primary determinant of the library size and diversity is the transformation frequency of the bacterial host which for *E. coli* is between $10^7$ to $10^9$ total transformants. Depending on the length of the peptide, this may result in a small fraction of the total combinatorial possibilities that can be screened. For example, the number of possible peptide sequences for a ten residue peptide is $(20)^{10}$ or $1.0 \times 10^{13}$, and the number of possible decacodon sequences (i.e., encoding nucleotide sequences) is $8.2 \times 10^{14}$. Thus, for a library of $10^9$ independent transformants, only a small fraction (0.01%) of the possible sequences typically can be screened for binding In addition, other factors such as proteolysis and defective secretion could potentially affect the diversity of peptide sequences that are expressed in vivo.

To create a recombinant peptide library that was not limited by the transformation frequency of cells, an in vitro polysome system was developed (described infra). A monoclonal antibody (mAb) (D32.39) which binds dynorphin B, a 13-residue optoid peptide was selected as a model receptor. Previous studies had shown that a six amino acid fragment of dynorphin B, Arg-Gln-Phe-Lys-Val-Val (RQFKVV) defines the linear epitope for the D32.39 mAb. A polysome library was generated containing $10^{12}$ random decapeptide (decacodon) sequences and screened for binding to D32.39. Following affinity selection, the enriched pool of polysomal mRNA was recovered, reverse transcribed to CDNA and amplified for a subsequent round of in vitro synthesis and selection. After just four rounds of selection, the majority of peptides contained within the pool shared a consensus sequence which was similar to the epitope sequence. All of these peptides bound specifically and with high-affinity to the antibody.

Construction of a Synthetic Gene for Expression of Nascent Peptides in vitro

A gene for expressing nascent peptides in vitro was constructed. The *E. coli* S30 system was used for in vitro expression of the construct genes; it translates mRNA with high-efficiency, is well-characterized, and is a coupled system that supports both transcription and translation.

Figure 3A:
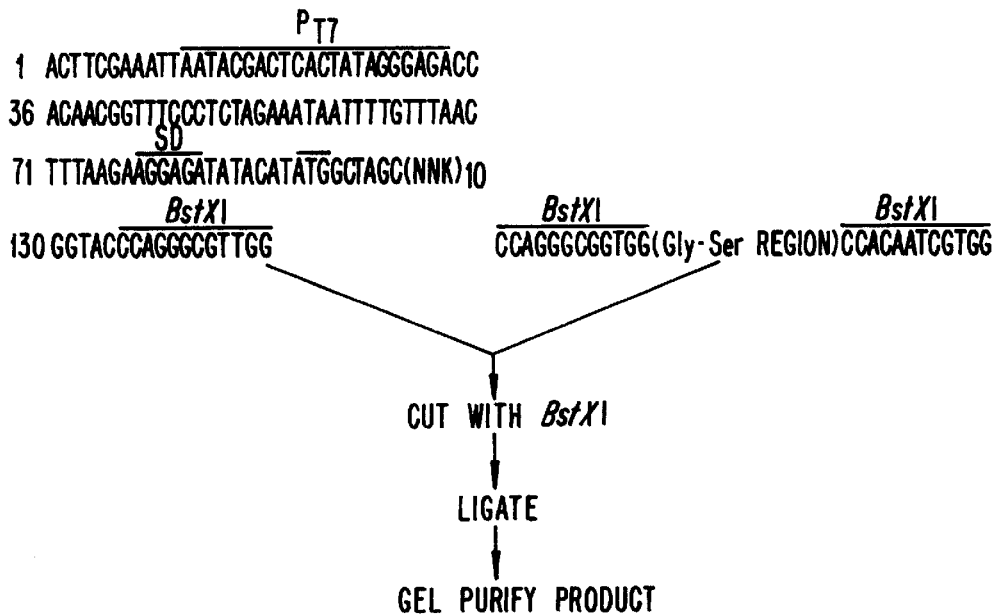
FIG. 3. (SEQ ID NO:44 & 45) Construction of a DNA library containing a random population of decacodon sequences. Panel (a): The nucleotide sequence of the degenerate region is shown on the left with the numbers indicating the nucleotide positions. The degenerate region was constructed by annealing 100 pmoles each of oligonucleotides ON1543 (positions 1–90) and ON1747 (complementary to positions 74–146) and extending in a reaction containing 104 units Sequenase (US Biochemical)/1 mH dNTP/10 mM DTT for 30 min at 37° C. The extended product was cleaved with BstXI, ethanol precipitated, and resuspended in water. The Gly-Ser coding region of plasmid pLH142 was modified by inserting noncomplementary BstXI site linkers between the HindIII/ClaI sites and NdeI/EcoRI sites resulting in plasmid pLM144. Plasmid pLM144 was cleaved with BstXI and the 277 bp fragment containing the Gly-Ser coding region shown on the right was gel purified, quantitated, and 4 μg were ligated to an equivalent amount of the degenerate region in a reaction containing 400 units T4 ligase/50 mM Tris-Cl pH 8/10 mM HgCl$_2$/10 mM DTT/1 mH ATP/25 μg/ml BSA for 16 hrs at 15° C. The 323 bp ligated product was gel purified and quantitated. The overlined sequences indicate the T7 promoter, gene 10 ribosome binding site (SD) and the initiator methionine (ATG). Panel (b): A schematic overview of the procedure used to produce the library members.
Figure 3B:
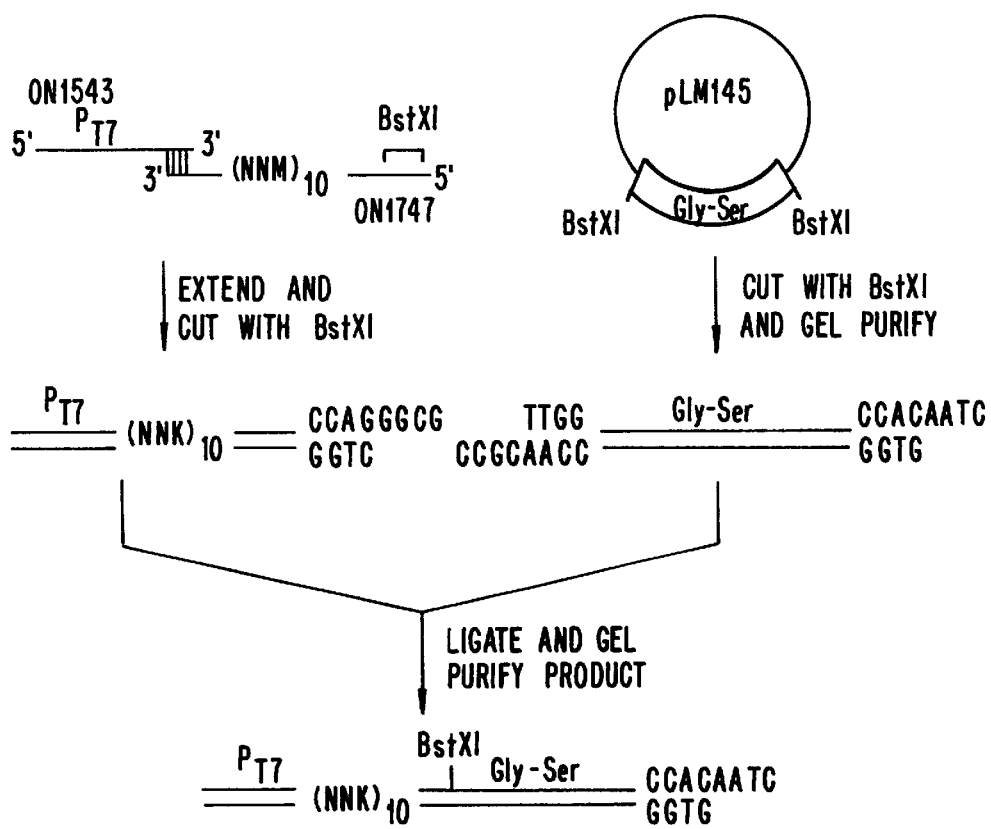

A synthetic gene for expressing N-terminal peptides under the transcriptional control of the bacteriophage T7 promoter was constructed. Oligonucleotide cassettes were synthesized and ligated to unique restriction sites of the T7 expression plasmid, pT7-7 (FIG. 1). Cassettes encoding the D32.39 epitope sequence (MARQFKVVT (SEQ ID NO:26), epitope sequence underlined) or a scrambled, non-binding control sequence (MAVFKRTVQ)(SEQ ID NO:27) were ligated in-frame to a repeating Gly-Ser coding region (FIG. 1. When these plasmids are linearized with HindIII prior to in vitro synthesis, the predicted gene product is a protein of 93 residues with either the epitope or control sequences beginning at amino acid position 3 (FIG. 1). There are no stop codons in any of the three possible reading frames. FIG. 3, panels (a) and (b), shows construction of a DNA library containing a random population of decacodon sequences.

The degenerate region was constructed by annealing 100 pmoles of oligonucleotides ON1543 (containing the T7 promoter ($P_{T7}$) and ON 1747 and extending in a reaction containing 104 units Sequenase (United States Biochemical), 1 mM dNTP, and 10 mM DTT for 30 minutes at 37° C. The extended product was cleaved with BstXI, ethanol precipitated, and resuspended in water. The BstXI fragment containing the Gly-Ser coding region shown on the right (FIG. 3) was prepared by digesting pLM145 with BstXI and gel-purifying the 277 bp fragment. Plasmid pLM145 was constructed by inserting BstXI site linkers between the HindIII/ClaI sites and the NdeI/EcoRI sites of pLM142. Approximately 4 μg of the Gly-Ser fragment was ligated to an equivalent amount of the degenerate region in a reaction containing 400 units T4 ligase, 50 mN Tris, pH 8,0, 10 mM DTT, 1 mM ATP, and 25 μg/ml BSA for 16 hours at 15° C. The 4111 bp ligated product (Mr, 267 kDa or $2.5 \times 10^{12}$ molecules/mg) was gel purified and ligated.

Alternatively, the 89 bp region flanked by BamHI and SalI restriction sites (FIG. 1) was replaced with a 155 bp segment from the gene pIII sequence and the resulting spacer sequence was shown to be a superior template for PCR amplification. Plasmid pLM182 appears to contain a superior Gly-Ser region for PCR amplification than pLM145 which is shown in FIG. 3. Plasmid pLM182 is identical to pLM145 except that the BamHI/Sal fragment shown in FIG. 1 is replaced with the 155 bp sequence from pIII. The BstXI sites of both plasmids are encoded by linkers that were cloned between the NdeI/EcoRI sites and HindIII/ClaI sites (see FIG. 1). The sequence of the NdeI/EcoRI linker is: CATATGGGTACCCAGGGCGTTGGTGAATTC (SEQ ID NO:28) (NdeI, BstXI, and EcoRI sites are underlined). The 155bp polynucleotide sequence is shown below with the Bam HI and SalI sites underlined:

GGATCCCAGTCGGTTGAATGTCGCCCT-TATGTCTTTGGCGCTGGTAAACCATATGAATT TTCTATTGATTGTGACAAAATAAACT-TATTCCGTGGTGTCTTTGCGTTCTTTTATATGT TGCCACCTTTATGTATGTATTTTC-GACGTTTCGACGTTTGCTAACATACTGTCGAC (SEQ ID NO:29)

To generate this fragment by PCR, we used ON2453 (5'-TATGGGTACCCAGGGCGTTGGTG-3') (SEQ ID NO:30) as the 5' primer which overlaps the BstXI site and ON1230 (5?-GGCGCCTGCTGCCTGCGTGTCGCCTG-TCGT-31) (SEQ ID NO:31) as the 3' primer which hybridizes to a region between the SalI ans HindIII sites as shown in FIG. 1.

Efficient spacer sequences are provided by various means. For example, the Gly-Ser segment can be mutagenized (e.g., randomly or pseudorandomly) to generate mutagenized sequence between the EcoRI and BamHI sites. In one aspect, a population of library members having a displayed peptide (or displayed antibody) having low-to-medium affinity ($K_D$ approximately 1 μM) for a target macromolecule (receptor or epitope) and a mutagenized spacer sequence are screened by binding to the target macromolecule and library members bound to the target are isolated. The population of isolated library members are enriched for those library members having enhanced binding affinity for the target, and are enriched for spacer sequences which are compatible with the higher binding affinity and/or which are efficiently amplified by Taq polymerase (or other PCR-compatible polymerase) and/or because a sequence in the mutagenized portion was efficient in stalling ribosomes (perhaps resulting in multivalent display) and causing an increase in recovery of the polysomal mRNA. Generally, after one or more rounds of such affinity selection, the sequence(s) of the selected spacer sequence(s) is/are determined.

In Vitro Synthesis and Isolation of Polysomes.

The *E. coli* S30 extract (Promega) was prepared from the B strain SL119 as described (Zubay G (1973) *Ann. Rev. Genet.* 7: 267). Synthesis reactions were contained in a final volume of 50 µl and included 20 µl of complete premix or premix lacking methionine for radiolabeling protein (Lesley et al. (1991) *J. Biol. Chem.* 266: 2632), 15 µl of extract, 1 µl of rifampycin (1 mg/ml), 100 units of T7 RNA polymerase (Ambion), 20 units of RNasin (Promega) and DNA as indicated. Reactions were incubated for 30 min at 37° C. and synthesis was stopped by placing on ice and diluting four-fold with polysome buffer (20 mm Hepes-OH pE 7.5/10 mM $MgCl_2$/1.5 µg/ml chloramphenicol/100 µg/ml acetylated bovine serum albumin (BSA)/1 mM dithiothreitol (DTT)/20 units/ml RNasin/0.1% Triton X-100). An alternative polysome buffer comprises 10 mN sodium phosphate, pH 7.4, 5 mM $MgCl_2$, 1 mM DTT, 0.85% Tween, 1.5 µg/ml chloramphenicol, 0.1% BSA, and 20 units/ml RNasin. To radiolabel mRNA or protein, 5 µCi of α-[$^{32}$P]UTP (Amersham, 3000 Ci/mmole) or [$^{35}$S]methionine (Amersham, 617 Ci/mmole) was included in the reaction and the incorporation of label was quantitated by precipitating duplicate samples with trichloroacetic acid (TCA), counting in a liquid scintillation counter and averaging the values. To isolate polysomes, the diluted reactions were centrifuged at 288,000×g for 36 min at 4° C. and the pellets were resuspended in polysome buffer and centrifuged a second time at 10,000×g for 5 min to remove any insoluble material. To measure the incorporation of mRNA into polysomes, equal amounts of $^{32}$P-labelled mRNA from a reaction were diluted in polysome buffer or elution buffer (polysome buffer plus 20 mM EDTA) and centrifuged as described above. The fraction of total mRNA which was specifically released from polysomes by EDTA was determined by TCA precipitation. FIG. 5 shows the effect of DNA library concentration on protein synthesis in vitro.

Affinity selection of polysomes.

Dynal beads were prepared according to the manufacturer. Microtiter wells were prepared for polysome binding by incubating each well with mAb D32.39 (5 µg per well) in PBS (10 mM sodium phosphate pH 7.4/120 mM NaCl/2.7 mM KCl) for 1 hr at 37° C., washing with PBS, blocking with PBS/1% nonfat milk for 1 hr at 37° C. and washing again with polysome buffer. Polysomes, as indicated, were incubated with the antibody for 2 hr at 4° C. Each well was washed five times with 100 µl of polysome buffer and the mRNA was recovered in 100 µl of elution buffer after incubating for 30 min at 4° C.

Figure 2B:
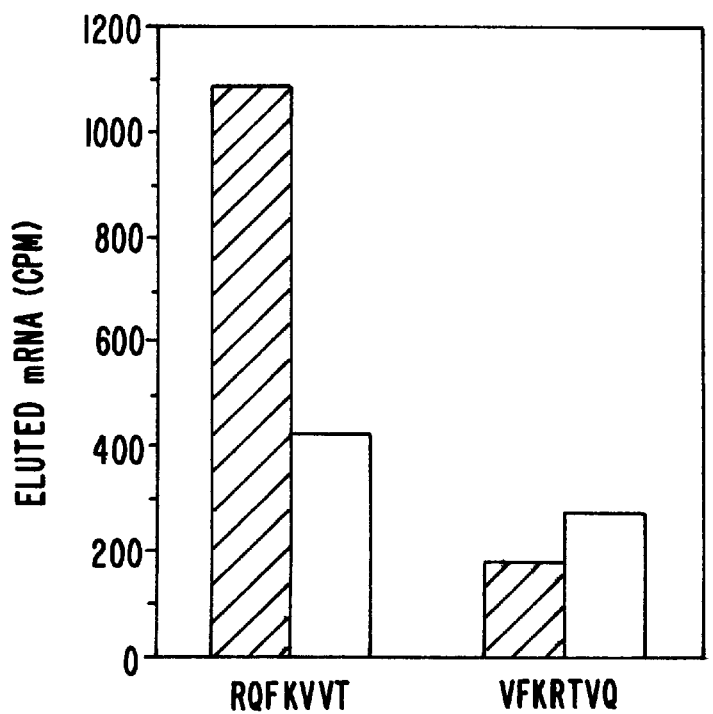

Specific Binding of Polysomes to mAb D32.39. The fraction of polysomes capable of binding specifically to mAb D32.39 via the nascent peptide was determined. Plasmids encoding the epitope (pLM138) or control sequences (pLM142) were linearized with HindIII, and incubated in separate S30 reactions containing α[$^{32}$P]UTP to label the newly-synthesized mRNA. Translation elongation was stopped by adding chloramphenicol and the reactions were centrifuged at high-speed to pellet polysomes and free ribosomal subunits. Radiolabelled polysomes containing the epitope or control coding sequences were added to separate microtiter wells containing the immobilized D32.39 mAb. Following binding and washing to remove unbound polysomes, EDTA was added to dissociate the complexes and the labelled mRNA was recovered. The amount of mRNA recovered from the wells was linear with increasing polysome input (FIG. 2A). Polysomes containing mRNA encoding the epitope bound at approximately 10-fold higher levels than control polysomes and binding was blocked by the prior addition of free dynorphin B peptide to the wells (FIG. 2B). Binding of polysomes to mAb D32.39 is peptide-specific.

The binding study demonstrates that 1–2% of polysomal mRNA encoding the epitope is recovered from the antibody. This low recovery is not caused by inefficient release of mRNA from the antibody since equal amounts of mRNA were recovered with phenol extraction or EDTA addition. The possibility that poor binding is caused by inefficient capture of polysomes by D32.39 immobilized in the microtiter well was evaluated. Unbound polysomes were removed from the microtiter well following the binding step and added to a fresh well containing immobilized D32.39. This was repeated with identical conditions for a third well. From all three wells, approximately the same percentage of input polysomal mRNA (1%) was recovered. Thus at least 3% and probably a much greater percentages of polysomes containing the epitope are capable of binding the maximum percentage of binding was not determined. Alternative immobilization matrices such as beads or mini columns for improving the efficiency of polysome capture can be used.

Screening of a polysome library.

Polysomes were isolated from a reaction programmed with 440 ng of DNA library and equal portions were added to six microtiter wells containing the immobilized mAb D32.39. Following affinity selection, the recovered mRNA samples were combined and treated with 6 units of DNase I (Ambion) for 15 min at 37° C. after raising the $MgCl_2$ concentration to 40 mM. The mRNA was phenol extracted, ethanol precipitated in the presence of glycogen and the pellet was resuspended in 20 µl of RNase-free water. A portion of the mRNA (8.5 µl) was heated for 3 min at 80° C., chilled on ice and 50 pmoles of primer ON1914 (5' GAT-TGTGGAAGCTTGGCGCCTGCT 3') (SEQ ID NO:32) were added to synthesize cDNA using the AMV reverse transcription system (Promega). The cDNA was amplified by PCR in a reaction consisting of 50 mM KCl, 10 mM Tris-Cl pH 9, 0.1% Triton X-100, 2.5 mM $MgCl_2$, 0.5 mM of dNTP (dATP, dCTP, dGTP, dTTP), 5 units of Taq polymerase (Promega), and 0.5 µH each of primer ON1415 containing the T7 promoter (5' ACTTCGAAATTAATAC-GACTCACTATAGGGAGACCACAACGGTTTCCCTCT 3') (SEQ ID NO:33)and primer ON1230 (5' GGCGCCT-GCTGCCTGCGTGTCGCCTGTCGT 3') (SEQ ID NO:34). Amplification consisted of 30 cycles of denaturation at 95° C. for 45 sec, and annealing/extension at 72° C. for 1 min. The amplified product was gel purified and quantitated by measuring the $A_{260}$.

DNA sequencing.

Subcloning of the DNA pool to the phagemid vector, pAFF6, for sequencing and ELISA is shown schematically in FIG. 4. Single stranded phagemid DNA was isolated by Prep-A-Gene (Biorad) and the random region was sequenced using the Sequenase system (United States Biochemical).

ELISA.

To measure phage binding by ELISA, the microtiter wells were prepared as described above except that 1 µg of mAB D32.39 per well was used and the blocking buffer consisted of PBS/1% BSA. Duplicate portions of phage supernatant (50 µl) were added to wells and incubated for 2 hr at 40° C. Wells were washed with 50 volumes of PBS, and 100 µl of horseradish peroxidase conjugated to sheep anti-M13 IgG (1:2000 dilution, Pharmacia) was added and incubated for 1 hr at 4° C. Wells were washed with PBS and binding was detected by adding substrate (0.2 mg/ml 2',2'-azino-bis(3-ethylbenzthiazoline-6-sulphonic acid) diammonium/50 mM citric acid pH 4/0.05% hydrogen peroxide) and measuring the $A_{405}$. The positive and negative controls were phage expressing the D32.39 epitope and control peptides, respectively. Phage clones were scored as positive if the average $A_{405}$ value was at least two-fold greater than that obtained for binding to wells not coated with the mAb or to wells preincubated with 10 μM dynorphin B peptide prior to adding phage.

Determination of peptide binding affinities.

Peptides were synthesized with an Applied Biosystems model 431A peptide synthesizer using Fmoc-protected amino acids. The peptides were purified to greater than 90% purity by HPLC and confirmed by mass spectroscopy. The competition binding assay was performed and included a low concentration (50 pM) of the tracer peptide containing the D32.39 epitope sequence.

RESULTS

Screening of a Polysome Library.

Polysomes expressing a library of peptides were screened for binding to the D32.39 mAb. An in vitro system was programmed with DNA containing $10^{12}$ different decacodons, incubated and polysomes were isolated and added to microtiter wells containing the immobilized mAb D32.39. Following affinity selection, the bound mRNA was recovered and copied to CDNA using reverse transcriptase and amplified by PCR using primers that included the sequences for the promoter and leader regions of T7 RNA polymerase. A portion of the amplified DNA product was then added to the S30 system for a subsequent round of in vitro synthesis and affinity selection.

After each round of selection, a portion of the amplified DNA template was subcloned to pAFF6 and the random region was sequenced. The sequences of selected clones isolated from rounds 2, 3, 4, and 5 all bear similarity to the known six-residue epitope and related sequences identified in previous studies (FIG. 6). The most highly-conserved residues are an invariant arginine at position one and phenylalanine at position three. The majority of the clones (52%) contain the positively charged residues lysine, arginine or histidine at position 4. The aliphatic residues valine, isoleucine, leucine and alanine are the most frequent group of amino acids found at positions 5 (76%) and 6 (71%) with valine the preferred residue. No strong bias was evident for residues in the second position.

The binding specificity of these peptides for the target mAb D32.39 was determined by ELISA. Each of the phage clones express on their surface the polysome-derived peptides as N-terminal fusions to the capsid protein pIII. The N-terminal sequence of the processed recombinant pIII is identical to the polysome-derived sequence for the first 14 residues. Each of the 21 unique peptide clones was tested for binding to D32.39 using a phage ELISA. All of the clones were positive in the ELISA test except for sequences HNE-GIRMFRVV (SEQ ID NO:35), GMYETRLFHVG (SEQ ID NO:36) and FSERRFSVCW (SEQ ID NO: 37) (epitope-like sequence underlined) These three contain 29 nucleotides in the random nucleotide region instead of 30 resulting in a frameshift mutation of the pIII fusion; the frameshifts are an artifact of subsequent cloning manipulations.

Binding Affinities of Enriched Peptides for mAb D32.39.

Peptides corresponding to some of the enriched sequences were chemically synthesized, purified and their identity confirmed by mass spectrometry. A competition binding assay was used to estimate their affinity for the mAb D32.39 and under the conditions of the assays the $IC_{50}$ value should approximate the $K_d$. Six peptides were assayed and the binding affinities range from 7.2 to 140 nM (FIG. 6). For comparison, the authentic dynorphin B peptide had an $IC_{50}$ of 0.29 nM in this assay.

The immense size of the polysome library reported here, $10^{12}$ members, is a direct result of the complete in vitro synthesis of DNA template, mRNA, and nascent peptide. By avoiding bacterial transformation, the typical size of a conventional, recombinant library ($10^7$–$10^9$ members) is exceeded by several orders of magnitude. For certain random peptides such as octapeptides or nonapeptides comprising $2.6 \times 10^{10}$ and $5.1 \times 10^{11}$ possible sequences, respectively, screening by polysomes may be the only currently available system for sampling the complete repertoire of combinatorial possibilities, or at least a substantial portion thereof. With appropriate modifications, it is possible to further increase the size of the library by increasing the translational capacity of the cell-free system. Such modifications include increasing the reaction volume 100-fold, or supplementing the system with a S30 component which may be limiting the formation of polysomes, such as free ribosomes or initiation factors.

In addition to larger libraries, the potential diversity of peptides expressed in vitro is also greater than conventional systems. Many cellular processes which limit in vivo expression such as defective secretion and proteolysis are absent or diminished in a cell-free system Further diversity is possible by including additional building blocks and incorporating non-naturally occuring amino acids into peptides using methods already established for the *E. coli* 530 system. Finally, diversity is not affected by the translational reading frame of the N-terminal nascent peptide. Three of the enriched sequences (HNEGIRMFRVV (SEQ ID NO:38), GMYETRLFHVG (SEQ ID NO:39), FSERRFS-VCW (SEQ ID NO:40)) contain 29 nucleotides in the random region instead of 30 resulting in a frameshift of the downstream coding region. We confirmed that one of these peptides (FSERRFSVCW) is capable of binding to the mob D32.39 with high affinity (110 nM). Thus, it is possible to enrich for peptide sequences of varying lengths despite changes in the reading frame of the synthetic gene which were constructed.

All of the peptides isolated by the polysome system bound to the D32.39 mAb with high affinity (7–140 nM), despite the existence of low affinity peptides for this mAb. One possible explanation for this is that polysome display is monovalent and only one initiation event occurs per mRNA molecule. This may explain why certain peptides such as clone 505 (PIMRSFKVVL) (SEQ ID NO: 41) which had the highest affinity of the peptides tested (7 nM) was overrepresented in clones sequenced from the later rounds of enrichment. Selective enrichment of high affinity peptides synthesized in vitro has important consequences. It is possible to include mutagenesis with each round of template amplification and achieve directed evolution of peptide ligands in a manner similar to that applied to ribozymes.

The in vitro polysome system can also be used for studying the role of mRNA sequence on translational pausing. The antibiotic chloramphenicol was used to arrest translation elongation and stabilize the polysome complex. By omitting the antibiotic, it is possible to screen a random coding region fused to the D32.39 epitope sequence and enrich for polysomes containing efficient pausing sequences.

EXAMPLE 2
Screening Single-Chain Antibodies with Nascent Polysome Method

In this example, nascent single-chain antibodies on polysomes are constructed and expressed in a polysome system The displayed scFv fragments exhibit binding specificity and affinity for antigen. Compared to bacteriophage antibody-display systems, the present polysome scFv display technology enables the construction and screening of libraries that are about 3 to 6 orders of magnitude larger than current antibody display techniques in the art. Furthermore, many problems associated with in vivo prokaryotic display systems (e.g., proteolysis, insoluble inclusion bodies, defective secretion) are avoided.

Construction of Plasmids Encoding scFv for DT or Antibody 179

Two single-chain antibody genes (scFv) specific for diphtheria toxin (DT) and antibody 179 were isolated from human spleen and mouse hybridoma, respectively, using the Pharmacia Recombinant Phage Antibody System (Pharmacia Biotech, Alameda, Calif.). The antibody genes are carried by the plasmid vector pCANTAB5E (Pharmacia) and are flanked by unique SfiI/NotI restriction sites. Each antibody coding sequence is also fused at the carboxy terminus to a 13-amino acid E-tag epitope sequence. To measure the specificity of antibody binding by ELISA, a 2 kb SfiI/EcoRI fragment from the CANTAB5E clone carrying the DT antibody gene was ligated to the same sites of a derivative of pLM139 resulting in plasmid pLM169. This plasmid contains the DT antibody gene under the transcriptional control of the bacteriophage T7 promoter. Plasmid pLM169 was linearized with EcoRI prior to adding to the in vitro transcription/translation system. To measure binding of antibodies displayed on polysomes, the 750 bp SfiI/NotI fragments from the pCANTAB5E clones carrying the DT antibody and Antibody 179 genes were ligated to the same site of a derivative of pLM138, resulting in plasmids pLM166 and pLM153, respectively. Both plasmids were linearized with HindIII prior to adding to the in vitro system. FIG. 7 schematically portrays the plasmid constructs.

In vitro expression of antibodies

The *E. coli* S30 extract (Promega) was prepared from the B strain SL119. Synthesis reactions were contained in a final volume of 50 µl and included 20 µl of complete premix, 15 µl of extract, 1 µl of rifampicin (1 mg/ml), 100 units of T7 RNA polymerase (Ambion), and 1.5 Ml of template DNA as indicated. Reactions were incubated at 37° C. for either 30 min to isolate polysomes or 60 min to synthesize soluble antibody. To radiolabel mRNA, 10 µCi of α-[$^{33}$P]UTP (Amersham, 3000 Ci/mmole) was included in the reaction and the incorporation of radioisotope was quantitated by precipitating duplicate samples with 10% trichloroacetic acid (TCA), counting in a liquid scintillation counter and averaging the values.

Determination of soluble antibody binding by ELISA

Figure 8:
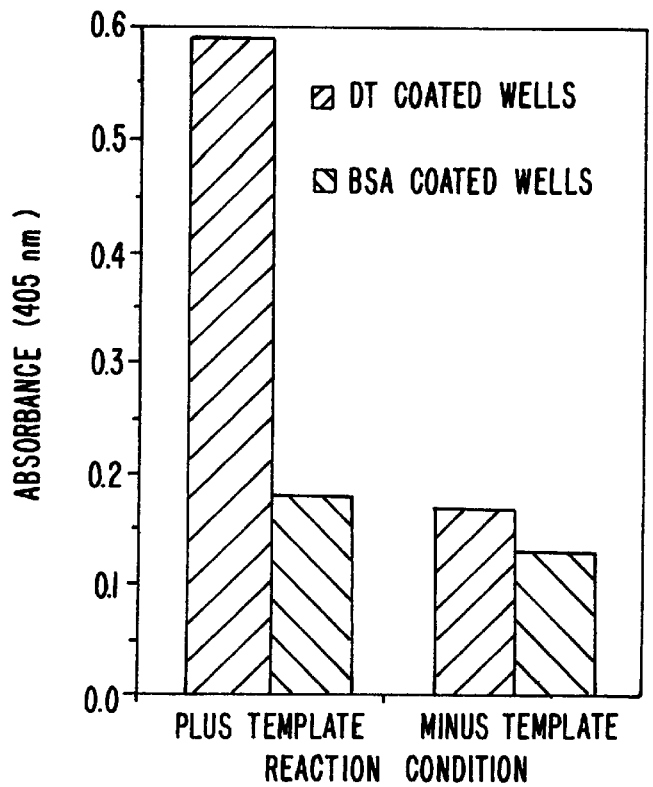
FIG. 8. Determination of soluble antibody binding by ELISA.

The binding specificity of a soluble antibody synthesized in vitro was determined by ELISA. In vitro reactions were incubated in the presence or absence of pLM169 for 60 min, and then diluted ten-fold with cold PBS (10 mM sodium phosphate pH 7.4, 140 mM NaCl, 2.7 mM KCl)/0.05% Tween-20 and placed on ice. Microtiter wells (Corning) were prepared by incubating each well with a 1 µg of diphtheria toxin (Calbiochem) or bovine serum albumin (BSA) in PBS for 1 hr at 37° C., washing with PBS, blocking with PBS/1% BSA for 1 hr at 37° C. and washing again with PBS. Duplicate portions of the diluted in vitro reactions (100 µl) were added to the wells and incubated for 1 hr at 4° C. Wells were washed 5 times with 250 µl of PBS, and the primary antibody (anti E-tag (Pharmacia)), 100 µl at 1 µg/ml in PBS/0.1% BSA/0.1% Tween) was added and incubated for 1 hr at 4° C. and washed as before. The plate was developed by adding 100 µl of alkaline phosphatase-conjugated goat anti-mouse antibody (Gibco, 1:1000 dilution in PBS/0.01% BSA), incubating for 1 hr at 4° C., washed as before, and treated with p-nitrophenol phosphate (5 mg/ml) in 1M diethanolamine hydrochloride, pH 9.8/0.24 mM MgCl$_2$ (100 µl per well). The A$_{405}$ was measured on a plate reader and the duplicate values were averaged. FIG. 8 graphically depicts the results.

Figure 9:
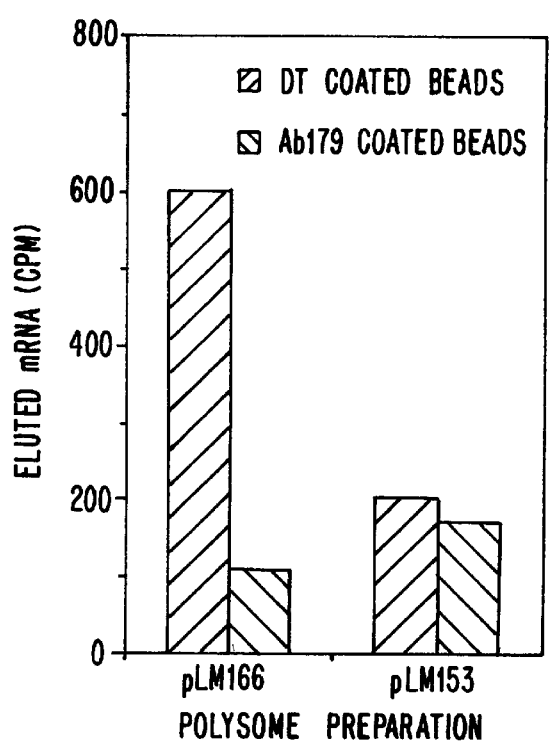
FIG. 9. Polysome isolation and binding of antibodies displayed on polysomes.
Figure 10:
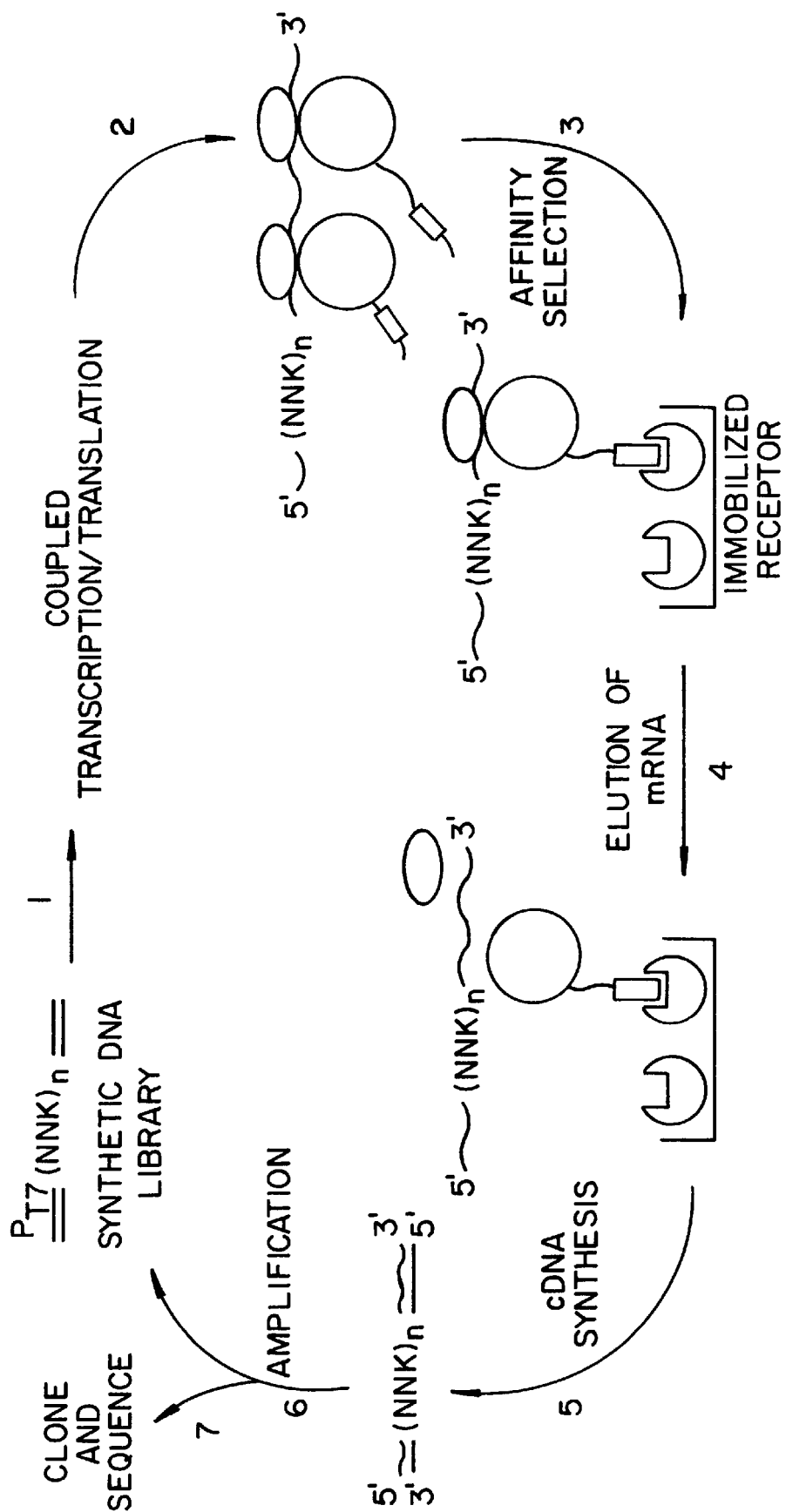
FIG. 10. Schematic overview of a representative nascent peptide display method of the invention. The defined sequence kernel (NNK)$_n$ represents the variable peptide portion of the nascent polypeptide. Step 7 represents the recovery and/or identification of the variable peptide portion (s) of selected library members, and may be performed after any number of cycles of the basic scheme (steps 1–6).

Polysome isolation and binding of antibodies displayed on polysomes (FIG. 3). To isolate polysomes, the in vitro reactions were incubated with either pLM166 or pLM153 and the reactions were stopped by placing on ice and diluting four-fold with polysome buffer (20 mM Hepes-OH pH 7.5, 10 mM MgCl$_2$ 1.5 µg/ml chloramphenicol, 100 µg/ml acetylated bovine serum albumin (BSA), 0.1% Tween-20). The diluted reactions were centrifuged at 288,00×g for 36 min at 4° C. and the pellets were resuspended in polysome buffer and centrifuged a second time at 10,000×g for 5 min to remove any insoluble material The labeled polysomes were quantitated by TCA precipitation and 46,000 cpm of each polysome preparation was added to 150 µg of magnetic beads (tosyl activated, Dynal) that had been coated with either 0.75 µg of diphtheria toxin (Calbiochem) or Ab179 (kindly provided by Bruce Mortensen) as the negative control. After binding for 1 hr at 4° C. with end over end turning, the beads were washed five times with polysome buffer and the mRNA was eluted in 100 µl of elution buffer (Polysome buffer containing 20 mM EDTA). The recovered mRNA was TCA precipitated and the radioactive counts determined, as shown in FIG. 9.

To facilitate correct folding of single-chain antibodies on polysomes, it is frequently desirable to incubate the polysomes in the presence of chaperones (e.g., GroEL or DnaK) prior to the binding (panning) step. To facilitate formation of disulfide bonds which are required for proper folding of a single-chain antibody, it is often desirable to incubate the polysome preparation in the presence of 0.2 mM glutathione (GSSG), 2 mM reduced glutathione (GSH), and 1 µM protein disulfide isomerase (PDI) for 15 minutes at 25°–30° C. prior to adding the target macromolecule (or small molecule epitope), and conducting the binding step at approximately 4° C.

Figure 11:
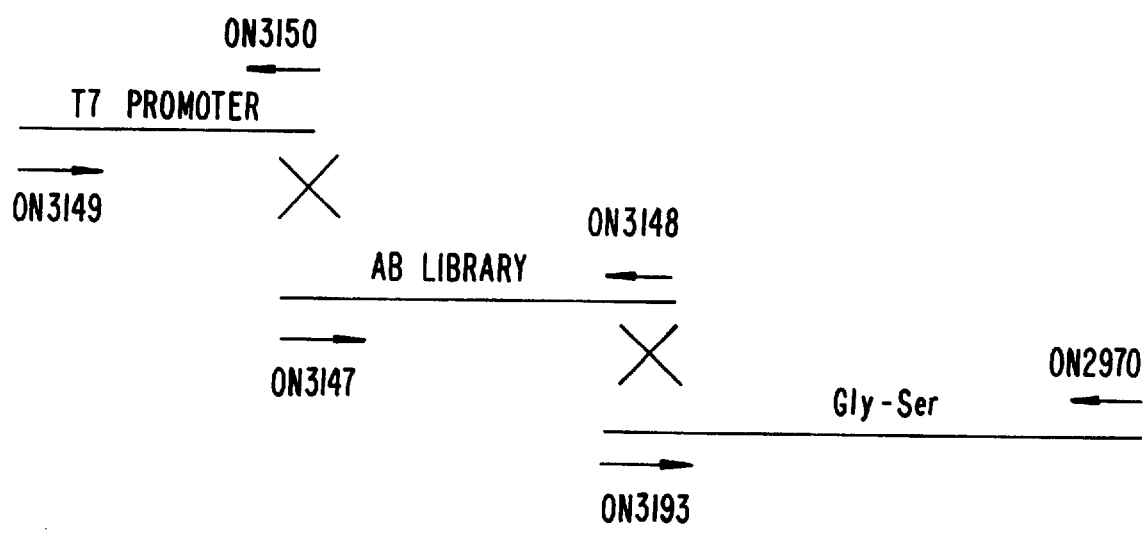
FIG. 11. Schematic overview of construction of a scFv display library by PCR overlap. Sequences of the oligonucleotides ON3149, 03150, 0N3147, ON3148, ON3193, and ON2970 are shown hereinbelow.

FIG. 11 shows construction of a single-chain antibody display polysome library made with PCR overlap (see Marks et al. (1991) *J. Mol. Biol.* 222: 581). DNA fragments encoding the T7 promoter, a naive antibody library, and the Gly-Ser region were amplified separately by PCR using the indicated primer sets. Equimolar portions were mixed and joined by PCR overlap in the absence of primers. The full length segment was then amplified using primers ON3149 and ON2970.

EXAMPLE 3
Use of Error-Prone PCR with Nascent Polysome Method

One of the potential advantages to screening peptide libraries with polysomes is the ability to incorporate mutagenesis between rounds of panning. This can be accomplished by substituting error prone PCR for normal PCR during the amplification step of each round.

The mutagenesis rate of error prone PCR, as described by Cadwell and Joyce (PCR Methods Appl. 2, 28 (1992)), can be increased from 0.66% to 2.7% using the modifications described by Bartel and Szostak (Science, 261, 1411–1418 (1993)). The method relies on serial dilution of the error prone PCR reaction products. A 100 ng DNA fragment containing the complete peptide expression gene, including the T7 promoter, peptide coding sequence, and spacer region, is subjected to three cycles of error prone PCR using the same primers (ON2856 and ON1230) used for normal PCR amplification. Approximately 13% of this reaction is added to a fresh reaction and subjected to another 3 cycles of error prone PCR- The serial dilution and PCR steps are repeated a total of 10 times. Afterwards, the products from each reaction are amplified 20 cycles using normal PCR and a portion is run on a gel to estimate yield. The 10 reactions are then pooled such that equimolar proportions from each dilution are present in the pool. The pooled DNA is gel purified and added to the in vitro system for the next round of screening.

The mutagenesis and serial dilution of the DNA results in a mutagenesis rate which is additive for each dilution. The pooling of reaction products assures that DNA subjected to low or high frequencies of mutagenesis is represented equally in the final product. Finally, the ability to mutagenize the entire gene, including the spacer region is advantageous. The spacer region can accommodate many point mutations without affecting translation. The generation of stop codons within the spacer region could eliminate display of some peptides, but this depends on the distance the ribosome has traveled before the addition of chloramphenicol to stop the reaction.

To demonstrate the method on polysome screening, we used the DNA pools generated from a previous panning experiment against the TPO receptor. These studies had identified 3 different high-affinity sequences, all specific for TPO, after 5 rounds of screening. Starting from the third round pool, a portion of the DNA was subjected to either normal PCR or error prone PCR (2.7% mutagenesis rate) and then panned for an additional 3 rounds using normal PCR. Afterwards the pool was cloned into the phage display vector, pAFF6, and the ELISA positive clones were sequenced.

The sequencing results showed that all of the ELISA positive sequences from the unmutagenized pool were comprised of the same three sequences identified previously, at both the amino acid and nucleotide level. For the mutagenized pool, however, all of the ELISA positive sequences were comprised of the same three amino acid sequences, but 4 out of 20 clones sequenced contained nucleotide changes resulting in silent amino acid changes. Three of the four clones contained single mutations, and one clone contained a double mutation. All of the nucleotide changes occurred at the third base of the codon, and none were K (G or T). This is consistent with the changes occurring as a result of the error prone PCR, and not originating from the starting library in which only NNK codons were used.

These results show that it is possible to generate and select for new mutations using the polysome system with error-prone amplification. The lack of amino acid changes present in the error-prone population could have several explanations. First error prone PCR was used just once on the third round pool, and not on the subsequent rounds of screening. Second, the diversity of sequences present in the third round pool may have been too low for generating sequences of higher affinity than the preexisting sequences. Third, although the mutagenesis rate we used (2.7%) is higher than the standard error prone rate (0.66%), it may only be possible to generate single or double amino acid changes after each round of screening due to the degeneracy of the genetic code. It is interesting to note, however, that the probability of obtaining 7 nucleotide changes in a 60 bp DNA fragment with an error frequency of 2.7% is only 0.001. A 2% rate of mutagenesis will not typically result in the elimination of desirable sequences, and error prone PCR may be used continuously following the initial round of selection.

Experimental

The error prone PCR was prepared by adding in the following order: 10 μl of 10× mutagenic PCR buffer (70 KM MgCl2, 500 mM KCl, 100 mM Tris-HCl, pH 8.3, 001% gelatin), 10 μl of 10× mutagenic dNTP mix (2 mM dGTP, 2 mM dATP, 10 mM dTTP, 10 mM dCTP), 1.2 μl each of primers ON2856 and ON1230 (50 μM) 52.6 μl of water, 11 μl of 5 mM MnCl2, 13 μl (100 ng) of DNA, and 1 μl (5 units) of Taq polymerase enzyme. The error prone PCR program consists of 1 min at 94° C., 1 min at 45° C., and 4 min at 72° C. for 3 cycles. After amplification, 13 μl were removed and added to a second error-prone PCR tube lacking DNA, and the amplification was repeated, The process was repeated a total of ten times.

Because the error prone PCR typically does not generate enough DNA for in vitro translation, normal PCR was used to amplify the reaction products from each serial dilution. Normal PCR conditions were 20 mM Tris-HCl (pH 8.4), 50 mM KCl, 1 mH MgCl2, 0.5 μM each of primers ON2856 and ON1230, 10% glycerol, 0.2 mM of each dNTP, 2.5 units of Taq polymerase, and 20 μl of the error prone PCR for a final volume of 100 μl. Amplification consisted of 30 sec at 94° C., 30 sec at 50° C., and 45 sec at 72° C. for 20 cycles. To estimate yield, 10 gl of each reaction were run on a 3% NuSieve, (FMC Corp.) agarose gel. Based on the intensities of the ethidium bromide stained bands, equal amounts of each amplification product were pooled. The mixture was purified by gel electrophoresis and saved for the next round of polysome screening.

The foregoing description of the preferred embodiments of the present invention has been presented for purposes of illustration and description. They are not intended to be exhaustive or to limit the invention to the precise form disclosed, and many modifications and variations are possible in light of the above teaching.

Such modifications and variations which may be apparent to a person skilled in the art are intended to be within the scope of this invention.

We claim:

1. A method for identifying multiple binding specificities of single chain antibodies, said method comprising:
   contacting under suitable binding conditions a multiplicity of antigen species with a polysome library displaying nascent peptides having a single chain antibody segment; and
   separating polysomes bound to the antigen species from polysomes not bound to the antigen species;
   synthesizing cDNA from the separated bound polysomes, thereby identifying single chain antibodies which bind to at least one of the antigen species present in the multiplicity of antigens.

2. A method of claim 1, wherein the multiplicity of antigen species comprises a library of beads or pins, each bead or pin having a single species of predetermined antigen.

3. A method of claim 2, wherein the antigen species comprise polypeptides synthesized on the beads or pins.

4. A method of claim 3, wherein the beads or pins individually comprise a discrete tag capable of reporting a sequence identity of the single species of polypeptide present on the bead or pin.

* * * * *